US012256915B2

(12) United States Patent
Menshes et al.

(10) Patent No.: US 12,256,915 B2
(45) Date of Patent: Mar. 25, 2025

(54) NON-PENETRATING TISSUE SEPARATOR

(71) Applicant: CARDIOVIA LTD., Nazareth (IL)

(72) Inventors: Ziv Menshes, Moshav Kidron (IL); Or Hazan, Yehud (IL); Maor Rosenberg, Haifa (IL); Ran Eliaz, Tsur Hadasa (IL); Yonatan Avraham Demma, Jerusalem (IL); Yair Elitzur, Jerusalem (IL)

(73) Assignee: CARDIOVIA LTD, Nazareth (IL)

( * ) Notice: Subject to any disclaimer, the term of this patent is extended or adjusted under 35 U.S.C. 154(b) by 545 days.

(21) Appl. No.: 17/610,336

(22) PCT Filed: May 13, 2020

(86) PCT No.: PCT/IL2020/050520
§ 371 (c)(1),
(2) Date: Nov. 10, 2021

(87) PCT Pub. No.: WO2020/230131
PCT Pub. Date: Nov. 19, 2020

(65) Prior Publication Data
US 2022/0192649 A1    Jun. 23, 2022

(30) Foreign Application Priority Data

May 15, 2019   (IL) .......................................... 266653

(51) Int. Cl.
*A61B 17/02*    (2006.01)
*A61B 17/00*    (2006.01)
(Continued)

(52) U.S. Cl.
CPC .... *A61B 17/0218* (2013.01); *A61B 17/00234* (2013.01); *A61B 17/22031* (2013.01);
(Continued)

(58) Field of Classification Search
CPC ........ A61B 17/0218; A61B 2017/0237; A61B 2017/0243; A61B 17/0281; A61B 2017/3425; A61B 2017/0212
See application file for complete search history.

(56) References Cited

U.S. PATENT DOCUMENTS

| 4,762,120 A | 8/1988 | Hussein |
| 5,531,780 A * | 7/1996 | Vachon ................ A61N 1/0575 |
| | | 607/120 |

(Continued)

FOREIGN PATENT DOCUMENTS

| CN | 1897868 A | 1/2007 |
| CN | 207384562 U | 5/2018 |

(Continued)

OTHER PUBLICATIONS

PCT International Search Report Report for International Application No. PCT/IL2020/050520, mailed Aug. 5, 2020, 5pp.
(Continued)

*Primary Examiner* — Julianna N Harvey
*Assistant Examiner* — Anna V. Little
(74) *Attorney, Agent, or Firm* — The Roy Gross Law Firm, LLC; Roy Gross

(57) ABSTRACT

The present invention relates to devices and methods for separating tissues to create an anatomical access space in the body, in particular, for providing an access to the space between the pericardium and the epicardium.

20 Claims, 38 Drawing Sheets

(51) Int. Cl.
 *A61B 17/22* (2006.01)
 *A61B 17/221* (2006.01)
 *A61B 17/34* (2006.01)
(52) U.S. Cl.
 CPC ........ *A61B 17/221* (2013.01); *A61B 17/3478* (2013.01); *A61B 2017/00247* (2013.01); *A61B 2017/00349* (2013.01); *A61B 2017/00353* (2013.01); *A61B 2017/3488* (2013.01); *A61B 2017/349* (2013.01)

(56) References Cited

U.S. PATENT DOCUMENTS

| | | | |
|---|---|---|---|
| 5,591,191 | A | 1/1997 | Kieturakis |
| 5,630,805 | A | 5/1997 | Ternamian |
| 5,658,307 | A | 8/1997 | Exconde |
| 5,676,636 | A * | 10/1997 | Chin .................. A61B 17/3417 600/209 |
| 5,782,823 | A * | 7/1998 | Mueller .................. A61B 18/22 606/7 |
| 5,935,141 | A * | 8/1999 | Weldon .......... A61B 17/320758 606/167 |
| 6,994,677 | B1 | 2/2006 | Buehlmann et al. |
| 8,986,278 | B2 | 3/2015 | Fung et al. |
| 9,149,276 | B2 | 10/2015 | Voss |
| 9,339,292 | B2 | 5/2016 | Poore et al. |
| 9,339,293 | B2 | 5/2016 | Morgan |
| 9,572,581 | B2 | 2/2017 | Vaughan et al. |
| 2002/0058956 | A1 | 5/2002 | Honeycutt et al. |
| 2002/0138091 | A1 | 9/2002 | Pflueger |
| 2003/0060685 | A1 * | 3/2003 | Houser .............. A61B 17/0218 600/206 |
| 2004/0087914 | A1 | 5/2004 | Bryan et al. |
| 2007/0088203 | A1 * | 4/2007 | Lau .................... A61B 17/0218 600/205 |
| 2007/0135686 | A1 * | 6/2007 | Pruitt, Jr. ........... A61B 17/0218 600/214 |
| 2008/0243164 | A1 | 10/2008 | Stefanchik |
| 2009/0248055 | A1 | 10/2009 | Spivey et al. |
| 2010/0274129 | A1 | 10/2010 | Hooven |
| 2011/0098531 | A1 | 4/2011 | To |
| 2012/0116418 | A1 | 5/2012 | Belson et al. |
| 2012/0136200 | A1 * | 5/2012 | Miraki .................. A61F 2/2427 600/37 |
| 2012/0172889 | A1 | 7/2012 | Chin et al. |
| 2012/0209306 | A1 | 8/2012 | Okoniewski |
| 2012/0238968 | A1 * | 9/2012 | Toy ..................... A61M 5/3286 604/272 |
| 2013/0274782 | A1 | 10/2013 | Morgan |
| 2014/0277056 | A1 | 9/2014 | Poore et al. |
| 2015/0290370 | A1 * | 10/2015 | Crunkleton ......... A61M 60/422 600/16 |
| 2016/0235973 | A1 | 8/2016 | Asleson et al. |
| 2017/0056043 | A1 * | 3/2017 | Jenkins ............. A61B 17/1688 |
| 2017/0119435 | A1 | 5/2017 | Gross et al. |
| 2017/0207467 | A1 | 7/2017 | Shelton, IV et al. |

FOREIGN PATENT DOCUMENTS

| | | | |
|---|---|---|---|
| EP | 3181071 A1 | 6/2017 | |
| WO | WO-2010042807 A2 * | 4/2010 | ............. A61B 10/04 |
| WO | 2015065898 A1 | 5/2015 | |
| WO | 2015123700 A1 | 8/2015 | |
| WO | WO-2017091812 A1 * | 6/2017 | ....... A61B 17/00234 |
| WO | 2018235072 A1 | 12/2018 | |
| WO | 2019072412 A1 | 4/2019 | |

OTHER PUBLICATIONS

PCT Written Opinion for International Application No. PCT/IL2020/050520, mailed Aug. 5, 2020, 5pp.

PCT International Preliminary Report on Patentability for International Application No. PCT/IL2020/050520, issued Nov. 16, 2021, 6pp.

* cited by examiner

NON-PENETRATING TISSUE SEPARATOR

This application is a National Phase of PCT Patent Application No. PCT/IL2020/050520 having International filing date of May 13, 2020, which claims the benefit of priority of Israeli Patent Application No. IL 266653, filed May 15, 2019, the contents of which are all incorporated herein by reference in their entirety.

FIELD OF THE INVENTION

The present invention relates to devices and methods for separating tissues to create an anatomical access space in the body, in particular, for providing an access to the space between the pericardium and the epicardium.

BACKGROUND OF THE INVENTION

Access to internal and external structures of the heart may be desirable for the treatment of cardiovascular disease. One way in which a heart may be accessed for device delivery is by an intravascular approach. However, intravascular access to the heart may not be applicable for delivery of larger devices, nor if external structures of the heart are targeted. In such circumstances, the heart may be accessed through an opening or puncture in the pericardium, which may provide direct access to the external (epicardial) surface of the heart. For that end, it is desirable to provide a sufficient and safer access to the space between the pericardium and the epicardium (known as the pericardial space), through which surgical tools, drugs and other medical devices can be passed, for example over a guidewire, to perform surgical procedures or standalone without the need of a guide wire. Such surgical procedures can include device delivery (such as coronary artery bypass grafts), drug delivery, left atrial appendage treatment, ablation of fibrillating tissue, treating arrhythmias, placement of ECG leads or other sensors, bleeding reduction by pressure application, pericardial drainage (pericardiocentesis), gene therapy and the like.

The space between the pericardial tissue and the epicardial tissue, referred to as the pericardial space, is in most cases only a potential space filled with pericardial fluid. US application publication no. 2012/238968 discloses a device configured to engage and penetrate a pericardial sac, via a helical tissue spring rotatable about its axis and having a distal tip configured to screw into the pericardial sac. US application publication no. 2015/065898 discloses an instrument for differentially dissecting complex tissue, which is provided with a dissecting wheel having projections configured to tear individual fibrous components, so as to dissect and penetrate through the tissue into the pericardial sac. There is therefore a need in the art for safe and easy to use devices and methods that enable separation between the pericardial and epicardial layers to create an access space with sufficient volume and a secure pathway, preferably without cutting or penetrating the epicardium or the myocardium, thereby avoiding potential damage to the heart.

SUMMARY OF THE INVENTION

The following embodiments and aspects thereof are described and illustrated in conjunction with systems, devices and methods which are meant to be exemplary and illustrative, not limiting in scope. In various embodiments, one or more of the above-described problems have been reduced or eliminated, while other embodiments are directed to other advantages or improvements.

According to some embodiments, there are provided devices and methods for separating between tissue layers, such as the pericardium and the epicardium, to provide an access space there between. The device generally includes an outer shaft and an inner shaft, axially movable relative to each other, wherein the inner shaft is attached to a grabbing element at its distal edge.

The grabbing element is equipped with surface features configured to contact and engage a tissue, such as the pericardium, promoting wrapping of the engaged tissue around the grabbing element when rotated around its central axis. The device can then be maneuvered to retract the grabbing element along with the wrapped tissue, thereby forming an access space between the grabbed pericardial tissue and the epicardium.

Advantageously, the grabbing element, provided as an atraumatic element, engages, wraps and retracts the pericardium without cutting or penetrating it. For example, the surface features and all edges of the grabbing element can be blunt so as to avoid undesired damage to the pericardial tissue during wrapping or retracting it to create the working space.

According to one aspect, there is provided non-penetrating tissue separator comprising an outer shaft, an inner shaft having an inner shaft lumen, and a grabbing element attached to a distal edge of the inner shaft.

The outer shaft comprises an outer shaft lumen, an outer shaft distal portion, and an outer shaft distal lip.

The grabbing element comprises a grabbing element distal surface, a grabbing element circumferential surface, a grabbing element inner opening, and surface features disposed along at least one of the grabbing element distal surface and the grabbing element circumferential surface.

At least a portion of the outer shaft is disposed around at least a portion of the inner shaft, so as to enable relative axial movement between the inner shaft and the outer shaft, thereby facilitating positioning of the grabbing element between a first state or a second state.

The grabbing element is rotatable about a central axis thereof, wherein the central axis of the grabbing element is directed in a distally oriented direction, orthogonal to the grabbing element distal surface.

The surface features are atraumatic surface features, configured to releasably engage and grasp a tissue via the surface features, without cutting, dissecting or penetrating it, during rotational movement of the grabbing element around its central axis, and to retain the tissue engaged therewith after rotational movement is halted.

According to another aspect, there is provided non-penetrating tissue separator comprising an outer shaft, an inner shaft having an inner shaft lumen, and a grabbing element attached to a distal edge of the inner shaft.

The outer shaft comprises an outer shaft lumen, an outer shaft distal portion, and an outer shaft distal lip.

The grabbing element comprises a grabbing element distal surface, a grabbing element proximal surface, a grabbing element circumferential surface, a grabbing element inner opening, and surface features disposed along at least one of the grabbing element distal surface, the grabbing element proximal surface, or the grabbing element circumferential surface.

At least a portion of the outer shaft is disposed around at least a portion of the inner shaft, so as to enable relative axial movement between the inner shaft and the outer shaft, thereby facilitating positioning of the grabbing element between a first state or a second state.

The grabbing element is rotatable about a central axis thereof, wherein the central axis of the grabbing element is directed in a distally oriented direction, orthogonal to the grabbing element distal surface.

The surface features are atraumatic surface features, configured to releasably engage and grasp a tissue via the surface features, without cutting, dissecting or penetrating it, during rotational movement of the grabbing element around its central axis, and to retain the tissue engaged therewith after rotational movement is halted.

According to some embodiments, the non-penetrating tissue separator further comprises a handle attached to at least one of the inner shaft and the outer shaft, wherein the handle is configured to facilitate relative axial movement between the inner shaft and the outer shaft, and wherein the handle is configured to facilitate rotation of the grabbing element.

According to some embodiments, the handle further comprises a steering knob engaged with the inner shaft and configured to facilitate at least one of axial movement or rotational movement of the inner shaft.

According to some embodiments, the steering knob is configured to rotate about a central axis thereof, and wherein the inner shaft is threadedly engaged with the steering knob.

According to some embodiments, the handle further comprises a first handle niche, wherein the steering knob is disposed within the first handle niche.

According to some embodiments, the steering knob comprises a steering knob internal bore, configured to accommodate the inner shaft extending there-along, such that the inner shaft is configured to axially move there through.

According to some embodiments, the inner shaft is configured to axially role within the steering knob internal bore via roller bearings attached thereto.

According to some embodiments, the handle further comprises a second handle niche, configured to enable visual exposure of at least a portion of the inner shaft extending there-through.

According to some embodiments, the non-penetrating tissue separator further comprises a first shaft spring disposed between the inner shaft and the handle, configured to provide resistance to a proximal displacement of the inner shaft.

According to some embodiments, the non-penetrating tissue separator further comprises a second shaft spring disposed between the inner shaft and the handle, configured to provide resistance to a distal displacement of the inner shaft.

According to some embodiments, the non-penetrating tissue separator further comprises indicia for indicating at least one of: the position of the grabbing element, the force applied by the grabbing element when pressed against an external surface, whether the tissue provides resistance to a proximal pull of the grabbing element, or whether the tissue has been grabbed by the grabbing element.

According to some embodiments, the inner shaft comprises a structural feature or a marking that can be compared against the indicia.

According to some embodiments, the non-penetrating tissue separator further comprises a cover configured to cover at least the second handle niche.

According to some embodiments, the non-penetrating tissue separator further comprises a latching mechanism comprising a lever pivotably movable about a pivot of a lever support body, and a grooved element comprising at least two axially spaced grooves, wherein the lever support body fixedly attached to the outer shaft, and wherein each groove is configured to accommodate an end portion of the lever, and wherein the grooved element is fixedly attached to the handle.

According to some embodiments, the latching mechanism further comprises a knob connected to an end of the lever, and a knob spring disposed between the knob and the lever support body.

According to some embodiments, the relative axial movement between the inner shaft and the outer shaft is facilitated by threaded engagement there between.

According to some embodiments, the relative axial movement between the inner shaft and the outer shaft is facilitated by threaded engagement between the inner shaft and the handle.

According to some embodiments, an outer diameter of the grabbing element is smaller than a diameter of the outer shaft lumen, such that the grabbing element is configured to be inserted into the outer shaft lumen.

According to some embodiments, the non-penetrating tissue separator further comprises an inner shaft retraction limiting mechanism, configured to limit the maximal retraction of the grabbing element in a proximal direction.

According to some embodiments, the outer shaft lumen comprises an outer shaft distal conical portion, tapering radially inwards from the outer shaft distal lip in a proximal direction.

According to some embodiments, the outer shaft lumen comprises an outer shaft distal socket, extending between the outer shaft distal lip and an outer shaft distal socket shoulder.

According to some embodiments, the non-penetrating tissue separator further comprises a cone head attached to the outer shaft distal portion and having a cone head distal lip defining a cone head opening.

According to some embodiments, the cone head further comprises a plurality of wings, configured to switch between a non-expanded state and an expanded state.

According to some embodiments, the wings are spring-biased radially inwards, and wherein the wings are configured to expand radially outwards due to an internal push force exerted on the cone inner surface during the grabbing element's axial movement there along.

According to some embodiments, the cone head is threadedly engaged with the grabbing element, and wherein the plurality of wings are configured to expand radially outwards to an expanded state when the grabbing element threadedly propagates from the first state to the second state.

According to some embodiments, the cone head is formed as a rigid non-deformable structure.

According to some embodiments, the cone head is formed as at least one helical coil having a plurality of spaced windings.

According to some embodiments, the non-penetrating tissue separator further comprises a delivery shaft disposed around at least a portion of the outer shaft, so as to enable relative axial movement between the outer shaft and the delivery shaft.

According to some embodiments, the cone head is configured to tilt relative to the outer shaft, thereby transitioning between an un-tilted cone state and a tilted cone state.

According to some embodiments, the cone head is pivotably attached to the outer shaft.

According to some embodiments, at least a portion of the cone head comprises at least one of: a flexible material or a shape-memory material.

According to some embodiments, the grabbing element is disc shaped, such that its axial length is shorter than its outer diameter.

According to some embodiments, the grabbing element is elongated, such that its axial length is equal to or longer than its outer diameter.

According to some embodiments, the inner shaft comprises a bendable inner shaft portion and a rigid inner shaft portion, such that a distal end of the inner shaft is configured to bend relative to the outer shaft.

According to some embodiments, the bendable inner shaft portion comprises a material which is more flexible than the material of the rigid inner shaft portion.

According to some embodiments, the bendable inner shaft portion comprises a spring.

According to some embodiments, the bendable inner shaft portion comprises slots or bellows that impart flexibility thereof.

According to some embodiments, the inner shaft further comprises an inner shaft threaded portion, extending proximally from a connection interface thereof with the grabbing element.

According to some embodiments, the non-penetrating tissue separator further comprises at least one optical sensor According to some embodiments, the non-penetrating tissue separator further comprises at least one ECG electrode.

According to another aspect of the invention, there is provided a kit comprising the non-penetrating tissue separator according to any one of the aforementioned embodiments, and an access device passable through the inner shaft lumen and through the grabbing element inner opening, and configured to either puncture, cut or penetrate the pericardium.

According to some embodiments, the access device is a needle comprising a distal needle portion.

According to some embodiments, the needle further comprises a needle restraining element configured to limit the penetration depth of the needle.

According to some embodiments, the distal needle portion is curved.

According to some embodiments, the access device comprises a thread having a circumferentially oriented sharp end, configured to puncture or penetrate the pericardium from a lateral direction during rotation thereof.

According to some embodiments, the kit further comprises a guidewire.

According to another aspect of the invention, there is provided a kit comprising the non-penetrating tissue separator according to any one of the aforementioned embodiments, and a balloon catheter configured to inflate a balloon distal to the non-penetrating tissue separator.

According to yet another aspect of the invention, there is provided a method of using a non-penetrating tissue separator, comprising the steps of:
 (i) providing the non-penetrating tissue separator according to any one of the aforementioned embodiments,
 (ii) advancing a distal portion of the non-penetrating tissue separator in a distal direction, while the grabbing element is in the first state,
 (iii) maneuvering the non-penetrating tissue separator to deploy the grabbing element from the first state to the second state,
 (iv) maneuvering the non-penetrating tissue separator to rotate the grabbing element, and
 (v) maneuvering the non-penetrating tissue separator to pull the grabbing element in the proximal direction.

According to yet another aspect of the invention, there is provided a method of using a non-penetrating tissue separator, comprising the steps of:
 (i) providing the non-penetrating tissue separator according to any one of the aforementioned embodiments,
 (ii) advancing a distal portion of the non-penetrating tissue separator in a distal direction, while the grabbing element is in the second state,
 (iii) maneuvering the non-penetrating tissue separator to rotate the grabbing element, and
 (iv) maneuvering the non-penetrating tissue separator to pull the grabbing element in the proximal direction.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

Figure 1A:
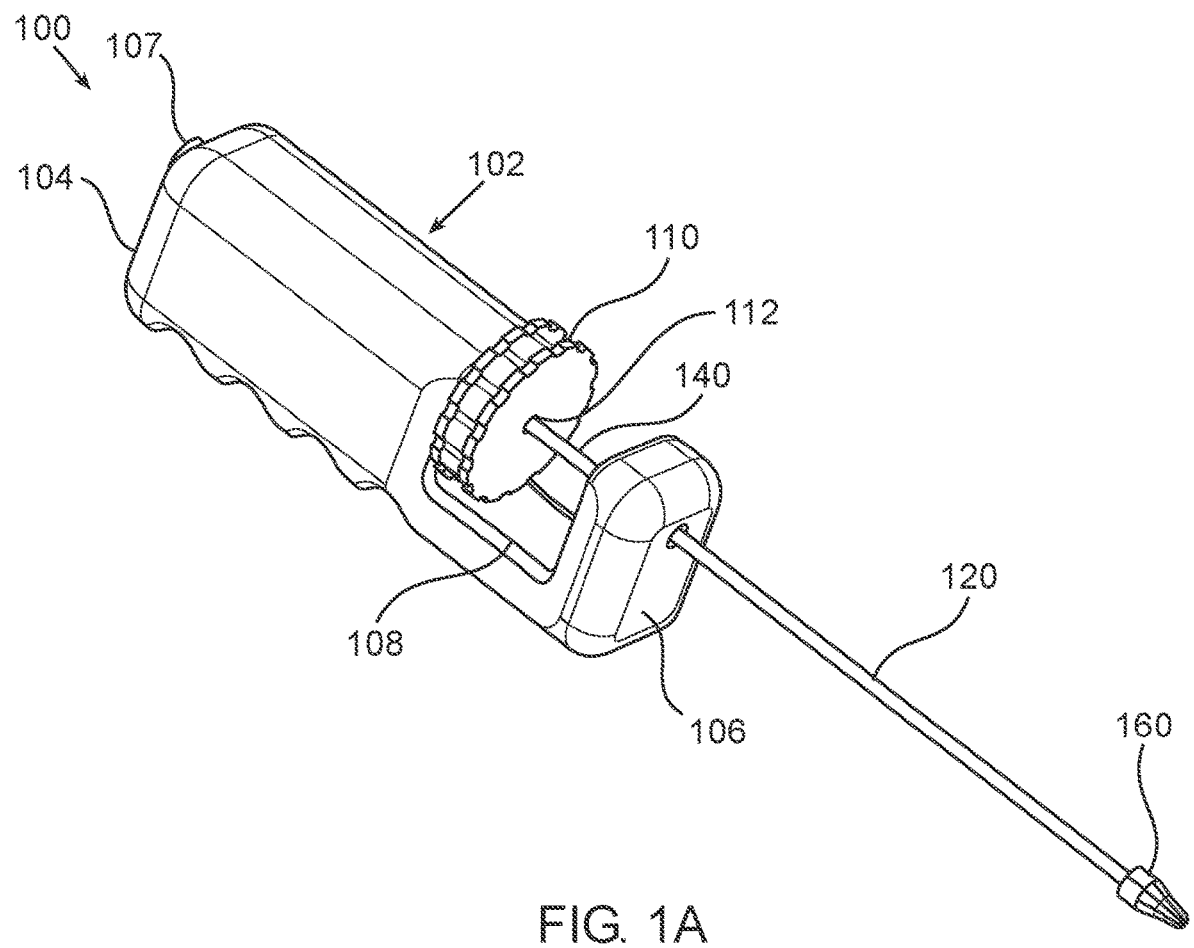
FIG. 1A constitutes a view in perspective of a non-penetrating tissue separator, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts throughout.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. In order to avoid undue clutter from having too many reference numbers and lead lines on a particular drawing, some components will be introduced via one or more drawings and not explicitly identified in every subsequent drawing that contains that component.

Figure 1B:
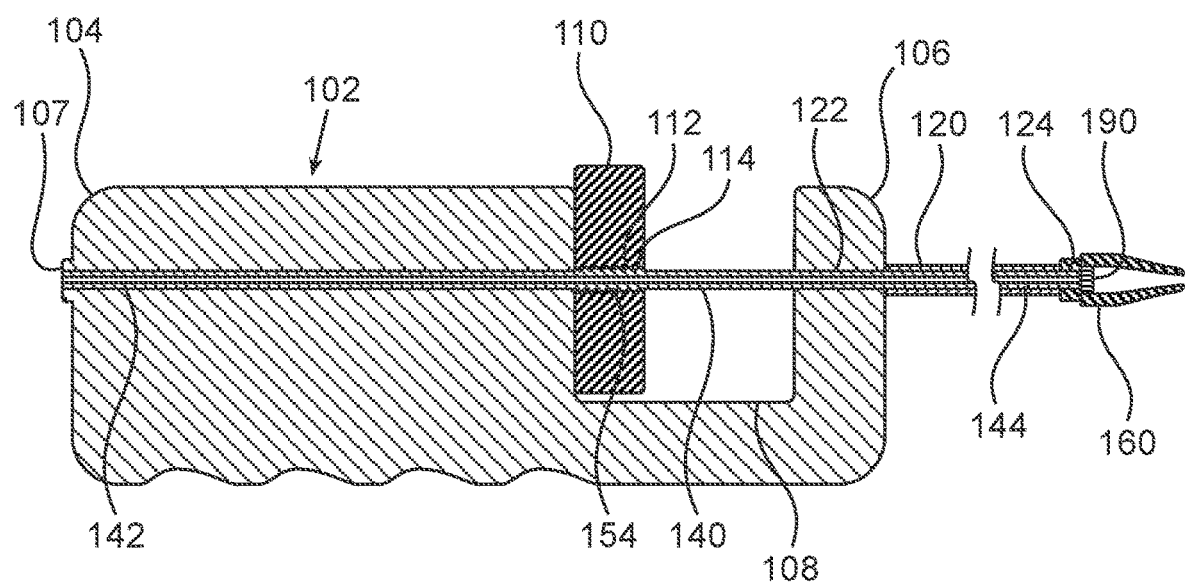
FIG. 1B constitutes a cross-sectional side view of the non-penetrating tissue separator of FIG. 1A.

Reference is now made to FIGS. 1A-F. FIGS. 1A and 1B constitute a view in perspective and a cross-sectional side view of a non-penetrating tissue separator 100 according to some embodiments. A non-penetrating tissue separator 100 comprises an outer shaft 120, an inner shaft 140 disposed within the lumen 132 of the outer shaft 120, and a grabbing element 190 attached to the distal edge of the inner shaft 140.

The outer shaft 120 comprises an outer shaft proximal portion 122, an outer shaft distal portion 124 having an outer shaft distal lip 126, an outer shaft external surface 128 and an outer shaft internal surface 130 defining the outer shaft lumen 132. The inner shaft 140 comprises an inner shaft proximal portion 142, an inner shaft distal portion 144, an inner shaft external surface 148 and an inner shaft internal surface 150 defining an inner shaft lumen 152.

At least a portion of the outer shaft 120 is concentrically disposed around at least a portion of the inner shaft 140, such that at least one of the inner shaft 140 or the outer shaft 120 is axially movable relative to the outer shaft 120 or the inner shaft 140, respectively, for example in a telescoping manner.

According to some embodiments, the inner shaft 140 can be moved distally while the outer shaft 120 is stationary, thereby causing the grabbing element 190 attached to its distal edge to move distally relative to the outer shaft distal lip 126. According to some embodiments, the outer shaft 120 can be moved proximally while the inner shaft 140 is stationary, thereby causing the outer shaft distal lip 126 to move proximally relative to the grabbing element 190.

According to some embodiments, the inner shaft 140 can slide freely within the outer shaft lumen 132. According to some embodiments, the outer shaft 120 can slide freely over the inner shaft external surface 148.

Within the context of this application the term "distal" generally refers to the side or end of any device or a component of a device, which is closer to the heart tissue when in use. More particularly, a distal end of the non-penetrating tissue separator 100 is the end closer to the pericardial surface 14, for example along the grabbing element 190.

Within the context of this application the term "proximal" generally refers to the side or end of any device or a component of a device, which is opposite the "distal end", and is farther from the heart tissue when in use, or closer to an operator of the non-penetrating tissue separator 100.

The grabbing element 190 is rotatable about a central axis thereof, wherein the central axis of the grabbing element 190 is directed in a distally oriented direction, orthogonal to the grabbing element distal surface 196. According to some embodiments, the inner shaft 140 is configured to rotate about its central axis within the lumen outer shaft lumen 132. According to some embodiments, the grabbing element 190 is affixed to the distal end of the inner shaft 140, such that rotation of the inner shaft 140 results in rotation of the grabbing element 190 is the same direction.

According to some embodiments, the non-penetrating tissue separator 100 further comprises a handle 102. The handle 102 comprises a handle proximal portion 104 and a handle distal portion 106. At least one of the inner shaft 140 and the outer shaft 120 is attached to the handle 102, such that the handle 102 is configured to facilitate the relative axial movement between the inner shaft 140 and the outer shaft 120.

According to some embodiments, the inner shaft 140 is connected to the handle 102, such that the handle 102 is configured to facilitate the relative axial movement between the inner shaft 140 and the outer shaft 120. According to some embodiments, the outer shaft 120 is connected to the handle 102.

The handle is further configured to facilitate rotation of the grabbing element 190, for example by facilitation rotation of the inner shaft 140.

According to some embodiments, at least a portion of the inner shaft 140 extends through at least a portion of the handle 102. According to some embodiments, the inner shaft proximal portion 142 extends through at least a portion of the handle 102. According to some embodiments, the handle comprises a handle inlet 107. According to some embodiments, the handle proximal portion 106 comprises the handle inlet 107. According to some embodiments, the inner shaft proximal portion 142 is configured to extend through the handle inlet 107. According to some embodiments, the handle inlet 107 is configured to provide access into the inner shaft lumen 152.

According to some embodiments, the handle 102 further comprises a first handle niche 108, disposed between the proximal portion 104 and the handle distal portion 106 (see FIGS. 1A-1B). According to some embodiments, the handle 102 further comprises a steering knob 110. According to some embodiments, the steering knob 110 is attached to the inner shaft, configured to facilitate axial movement of the inner shaft 140 in the distal and proximal directions.

According to some embodiments, the steering knob 110 is disposed within the handle niche 108. According to some embodiments, the steering knob 110 is formed as a steering wheel, configured to rotate about a central axis thereof. According to some embodiments, the steering knob 110 comprises a steering knob internal bore 112, dimensioned to accept the inner shaft 140 extending there through.

According to some embodiments, the inner shaft 140 is engaged with the steering knob 110, such that it is either movably or fixedly connected to the steering knob 110, or alternatively is retained via direct or indirect contact with the steering knob 110.

According to some embodiments, the inner shaft 140 is connected to the steering knob internal bore 112. According to some embodiments, the steering knob internal bore 112 comprises a steering knob threading 114, and a portion of the inner shaft external surface 148 comprises a matching inner shaft threaded portion 154, such that the inner shaft 140 is threadedly engaged with the steering knob 110. In such embodiments, rotation of the steering knob 110 in one direction can cause the inner shaft 140 to translate axially in the distal direction 92 relative to the handle 102, thereby causing the position of the grabbing element 190 to translate distally in direction 92 (see FIG. 1E).

According to some embodiments, the number and spacing of the threads of the steering knob threading 114, and thus the mating threads of the inner shaft threaded portion 154, and the axial length of the steering knob threading 114 and/or the inner shaft threaded portion 154, can be selected to provide a desired degree of travel for the grabbing element 190.

According to some embodiments, the outer shaft 120 is connected to the handle 102. According to some embodiments, the outer shaft 120 is fixedly attached to the handle 102. According to some embodiments the outer shaft 120 is immovable or stationary relative to the handle 120. According to some embodiments, the outer shaft proximal portion 122 is fixedly attached to the handle distal portion 106, for example by gluing, welding and the like.

Reference is now made to FIGS. 1C-1F, constituting zoomed in views of the distal region of the non-penetrating tissue separator 100 at different states, according to some embodiments. According to some embodiments, the non-penetrating tissue separator 100 further comprises a cone head 160, attached to the outer shaft distal portion 124. The cone head 160 comprises a cone proximal portion 164 connected to the outer shaft distal portion 124, a cone distal portion 166 having a cone distal lip 174, and a cone inner surface 178. The cone distal lip 174 defines a cone opening 168. According to some embodiments, the cone head 160 is attached to the outer shaft 120 such that the cone distal lip 174 is positioned distal to the outer shaft distal portion 124.

An outer distal edge of the non-penetrating tissue separator 100 is defined as the most distal edge between the outer shaft distal lip 126 and the cone distal lip 174. For example, if the non-penetrating tissue separator 100 does not include a cone head 160, the outer shaft distal lip 126 can serve as the outer distal edge. Alternatively, for embodiments including a cone head 160 attached to the outer shaft distal portion 124, the cone distal lip 174 can serve as the outer distal edge.

According to some embodiments, the non-penetrating tissue separator 100 is movable between a first state and a second state. A first state of the non-penetrating tissue separator 100 is defined as a state in which the distal surface 196 of the grabbing element 190 is positioned proximal to or flush with the outer distal edge, while the second state of the non-penetrating tissue separator 100 is defined as a state in which the distal surface 196 of the grabbing element 190 is positioned distal to the outer distal edge. According to some embodiments, the second state is further defined as a state in which a proximal surface 194 of the grabbing element 190 is distally spaced from the plane defined by the outer distal edge.

Any reference throughout the specification to a non-penetrating tissue separator 100 being movable between a first state and a second state, is equivalent to the grabbing element 190 being movable between a first state and a second state.

At least a portion of the outer shaft 140 is disposed around at least a portion of the inner shaft 120, so as to enable relative axial movement between the inner shaft 120 and the outer shaft 140, thereby moving the grabbing element 190 in a distal or a proximal direction relative to the outer shaft distal lip 126.

At least a portion of the outer shaft 140 is disposed around at least a portion of the inner shaft 120, so as to enable relative axial movement between the inner shaft 120 and the outer shaft 140, thereby transitioning the grabbing element 190 between the first state and the second state, or any state in between.

According to some embodiments, at least a portion of the outer shaft 140 is concentrically disposed around at least a portion of the inner shaft 120. According to some embodiments, the outer shaft 140 and the inner shaft 120 are coaxial.

According to some embodiments, the inner shaft 120 and the outer shaft 140 are configured to slide axially relative to each other by pushing the inner shaft 120 in a distal direction relative to the outer shaft 140.

According to some embodiments, the inner shaft 120 and the outer shaft 140 are configured to slide axially relative to each other by pulling or retracting the outer shaft 140 in a proximal direction relative to the inner shaft 120.

According to some embodiments, the handle 102 can be maneuvered by an operator to transition the non-penetrating tissue separator 100 between the first state and the second state, including states in between. According to some embodiments, internal threads of the steering knob threading 114 are configured to engage with external threads of the inner shaft threaded portion 154, such that rotation of the steering knob 110 causes corresponding axial movement of the grabbing element 190 toward the first state or the second state, depending on the direction of rotation of the steering knob 110.

Figure 1C:
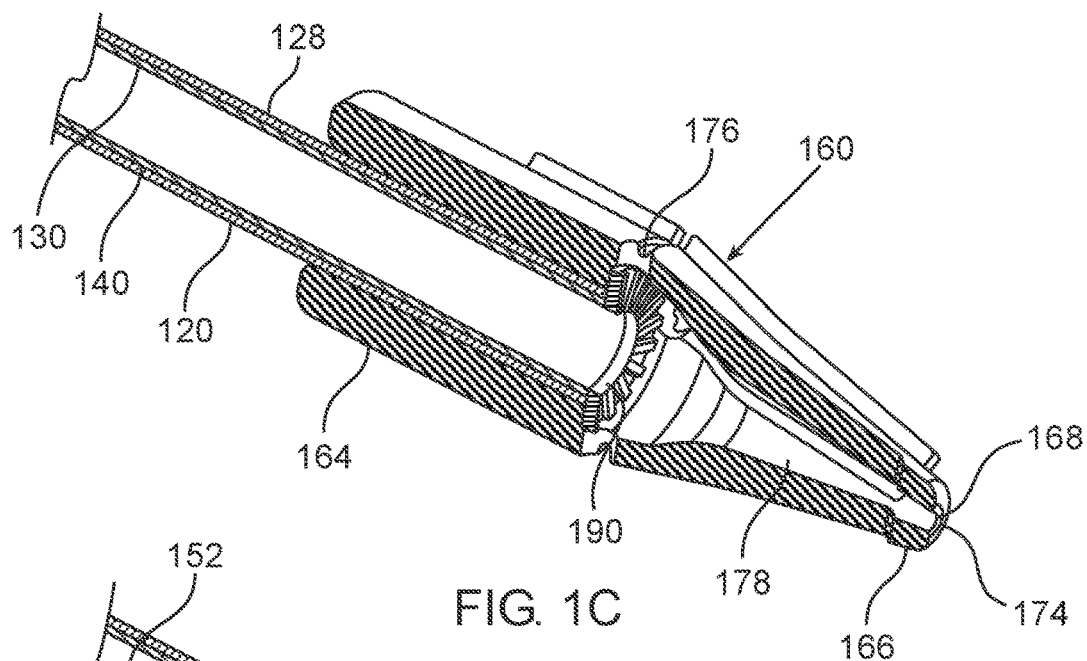
FIG. 1C constitutes a zoomed-in sectional view in perspective of the distal region of the non-penetrating tissue separator of FIG. 1A in a first state.
Figure 1D:
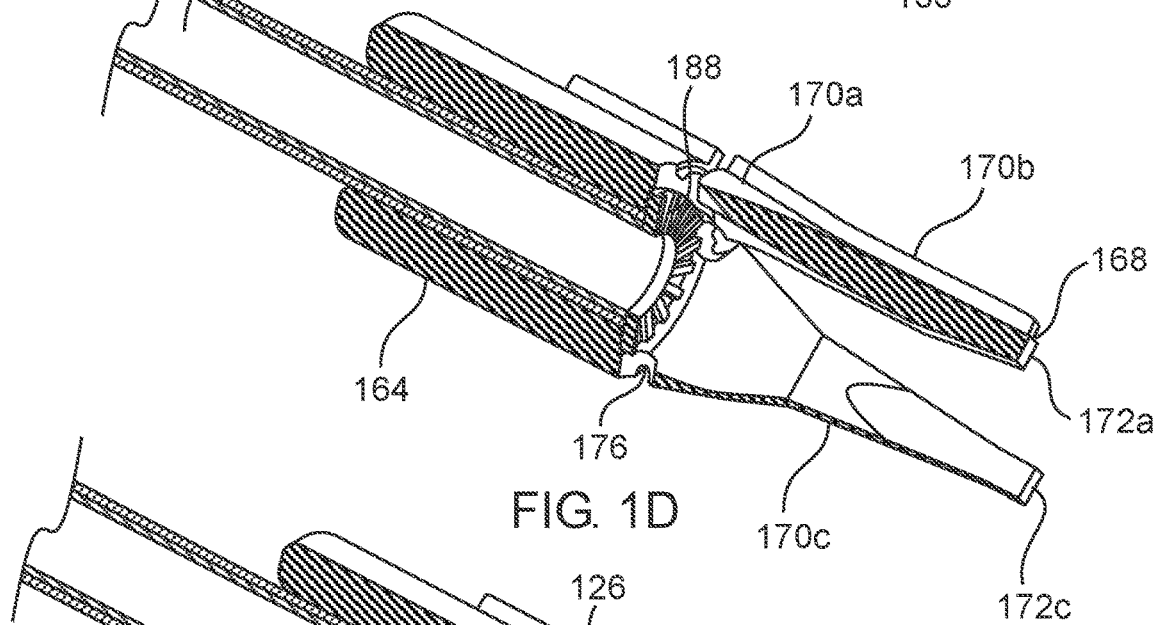
FIG. 1D constitutes a zoomed-in sectional view in perspective of the distal region of the non-penetrating tissue separator of FIG. 1A with expanded cone head wings.
Figure 1E:
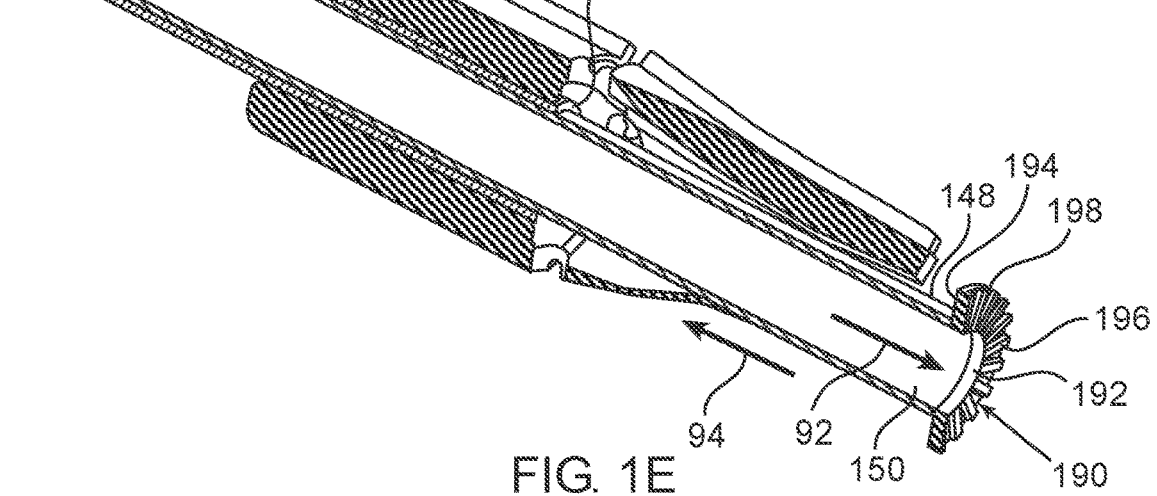
FIG. 1E constitutes a zoomed-in sectional view in perspective of the distal region of the non-penetrating tissue separator of FIG. 1A in a second state.
Figure 1F:
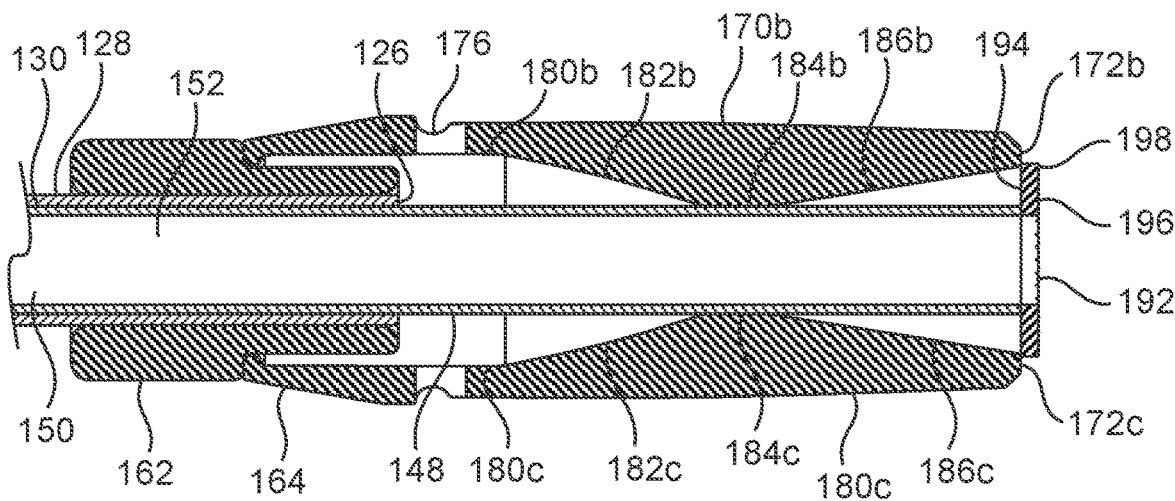
FIG. 1F constitutes a zoomed-in cross-sectional side view of the distal region of the non-penetrating tissue separator of FIG. 1A.

FIG. 1C shows a zoomed in view in perspective of the distal region of the non-penetrating tissue separator 100 in a first state, wherein the grabbing element 190 is positioned proximal to the cone distal lip 174. FIG. 1D shows the zoomed in view of FIG. 1C in a transitionary state between the first state and the second state. FIG. 1E shows the zoomed in view of FIG. 1C in a second state, wherein the grabbing element 190 is distally spaced from the cone distal lip 174. FIG. 1F shows a cross-sectional zoomed-in side view of the distal portion of the non-penetrating tissue separator 100, in a state prior to or post the state of FIG. 1E, such that the grabbing element 190 is positioned distal to the cone distal lip 174, but its proximal surface 194 is not spaced distally to the cone distal lip 174.

According to some embodiments, the cone head 160 is connected to the outer shaft 120 via an intermediate connector 162 (see FIG. 1F), wherein the intermediate connector 162 is fixedly attached to the outer shaft distal portion 124, and the cone proximal portion 164 is attached to the intermediate connector 162.

According to some embodiments, such as the embodiment illustrated in FIGS. 1A-1F, the cone head 160 comprises a plurality of wings 170, such as wings 170a, 170b, 170c, oriented in a distal axial direction, separated by notches there between. Each wing 170 comprises a wing distal lip 172, wherein the plurality wing distal lips 172, such as wing distal lips 172a, 172b, 172c, together form the cone distal lip 174. The cone head 160 and the wings 170 are configured to switch between a non-expanded state (see FIG. 1C) and an expanded state (see FIGS. 1D-E).

According to some embodiments, the wings 170 are provided with internal flexibility, such that they are spring-biased radially inwards (see FIG. 1C), and can be pushed radially outwards (see FIG. 1D) by a force exerted thereon, such that the wing distal lips 172 expand radially away from each other, to form a wider cone opening 168 relative to the non-expanded position of FIG. 1C.

According to some embodiments, the cone 160 further comprises wing flexion points 176 at the proximal ends of the notches between the wings, positioned between the cone proximal portion 164 and the cone distal portion 166. The wing flexion points 176 can be formed as notch grooves having a diameter which is slightly larger than the width of the notches, configured to provide additional flexibility to the wings.

According to some embodiments, each wing 170 further comprises a wing proximal straight surface 180 (see FIG. 1F) extending distally from the region of the flexion points 176, a wing first inclination 182 extending distally from the wing proximal straight surface 180 and inclined radially inwards, a wing medial shoulder 184 extending distally from the wing first inclination 182, and a wing second inclination 186 extending distally from the wing medial shoulder 184 and inclined radially outwards, terminating at the wing distal lip 172. The wing proximal straight surfaces 180, wing first inclinations 182, wing medial shoulders 184 and wing second inclinations 186, together form the cone inner surface 178.

FIG. 1C shows the grabbing element 190 in the first state, positioned proximal to the wing distal lips 172, and more specifically, in close proximity to or in contact with the outer shaft distal lip 126. The cone head 160 and the wings 170 are shown in a non-expanded state in FIG. 1C, wherein the wings 170 are biased radially inwards toward each other, such that the diameter of the cone opening 168 is smaller than the diameter of the grabbing element 190.

The cone head 160 and the wings 170 are shown in an expanded state in FIG. 1D, wherein the wings 170 are flexed radially outwards. According to some embodiments, the non-penetrating tissue separator 100 comprises a mechanism configured to expand the wings 170 radially outwards, such as a cable or wire attached to the external surface of the wings 170 or to the wing lips 172, which can be pulled in a proximal direction, for example by pulling the cable's or wire's proximal end at the handle 102, in order to expand the wings 170 (embodiments not shown).

According to some embodiment, the wings 170 are configured to expand radially outwards due to an internal push force exerted on the cone inner surface 178 during the grabbing element's 190 axial movement there along, for example toward the second state.

The wing proximal straight surfaces 180 are configured to enable axial translation of the grabbing element 190 there along, without expanding the wings 170. The axial length of the wing proximal straight surfaces 180 defines the path, extending from the outer shaft distal portion 126, along which axial movement of the grabbing element 190 does not exert any force on the wings 170.

When the grabbing element 190 is pushed distally further along the wing first inclinations 182, the wings slide over its circumferential surface 198 and expand radially outwards. The grabbing element 190 further slides over the wing medial shoulders 184 and wing second inclinations 186 as it continues to advance in a distal direction 92, until it exits the cone head 160 through the cone opening 168. FIG. 1E shows the grabbing element 190 positioned in the second state, distally spaced from the wing distal lips 172. The grabbing element 190 can be also be pulled back in the proximal direction 94.

According to some embodiments, the wing medial shoulders 184 are configured to abut or press against the inner shaft external surface 148 as the grabbing element 190 exits the cone head 160 through the cone opening 168, and the wing second inclinations 186 are inclined at an angle that defines an outer diameter of the cone opening 168, which is smaller than the outer diameter of the grabbing element 190. In this manner, when the grabbing element 190 is retracted in the proximal direction 94 from the second state, its proximal surface 194 is prevented from re-entering the cone head 160 (see FIG. 1F).

According to some embodiments, the wing second inclinations 186 are inclined at an angle that defines an outer diameter of the cone opening 168, which is larger than the outer diameter of the grabbing element 190 when the wing medial shoulders 184 abut the inner shaft external surface 148, so as to allow proximal retraction of the grabbing element 190 back into the cone head 160, potentially toward the first position.

According to some embodiments, the wings 170 are plastically deformable, such that when they are bent radially outwards, they remain in that position and do not strive to bend back toward each other.

According to some embodiments, the cone head 160 provides an atraumatic interface configured to avoid damaging the tissues. According to some embodiments, the cone distal lip 174 is blunt and not sharp, e.g. rounded.

According to some embodiments, the non-penetrating tissue separator 100 further comprises an atraumatic end-cap (not shown) configured to cover the distal end of the device 100 so as to provide an atraumatic distal interface mitigating tissue damage during advancement of the device 100 towards the patient's heart. According to some embodiments, the atraumatic end-cap is attached to or covers the outer distal edge.

According to some embodiments, the atraumatic end-cap comprises flaps that allow the grabbing element 190 or other instruments to be distally pushed and pass there through.

According to some embodiments, the process of transitioning the grabbing element 190 between the first state and the second state, is achieved by retracting the outer shaft 120 along with the cone head 160 in a proximal direction, instead of advancing the inner shaft 140 in a distal direction. The relative interaction between the grabbing element 190 and the cone head 160 in such embodiments, is identical to the relative interaction between the elements as described herein above, including optional radial displacement of the wings 170 that slide over the grabbing element 190.

Reference is now made to FIGS. 2A-F, showing different embodiments of the grabbing element 190. The grabbing element 190 comprises a grabbing element inner opening 192, a grabbing element proximal surface 194, a grabbing element distal surface 196, and a grabbing element circumferential surface 198.

According to some embodiments, the grabbing element inner opening 192 is substantially equal to the diameter of the inner shaft lumen 152. According to some embodiments, the grabbing element inner opening 192 and the inner shaft lumen 152 are coaxial.

The term "substantially", as used herein, refers to a maximal optional deviation of 10% from a referred value.

According to some embodiments, the grabbing element 190 further comprises surface features 188 disposed along at least one surface thereof. According to some embodiment, the surface features 188 are disposed along at least one of the grabbing element distal surface 196 and the grabbing element circumferential surface 198. According to some embodiment, the surface features 188 are disposed along the grabbing element proximal surface.

According to some embodiments, the grabbing element 190 is disk-shaped.

Figures 2A, 2B:
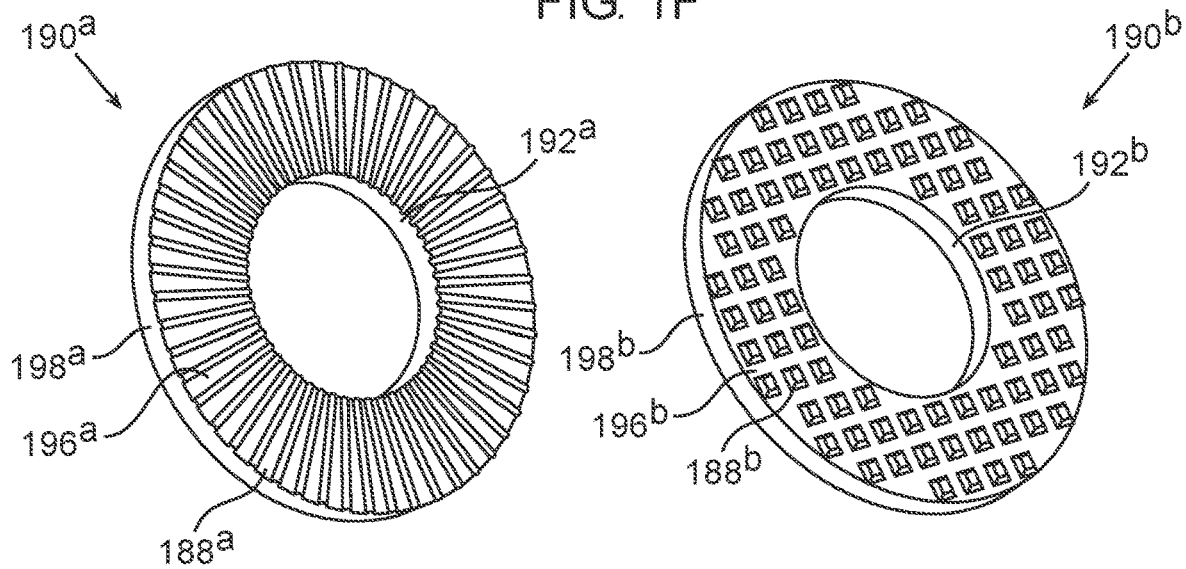
FIGS. 2A-2F constitute views in perspective of different embodiments of a grabbing element.

FIG. 2A illustrates an embodiments of a grabbing element $190^a$ provided with surface features $188^a$ in the form of radial ridges extending along the grabbing element distal surface $196^a$. FIG. 2B illustrates an embodiments of a grabbing element $190^b$ provided with surface features $188^b$ in the form of dimples protruding from grabbing element distal surface $196^b$.

Figures 2C, 2D:
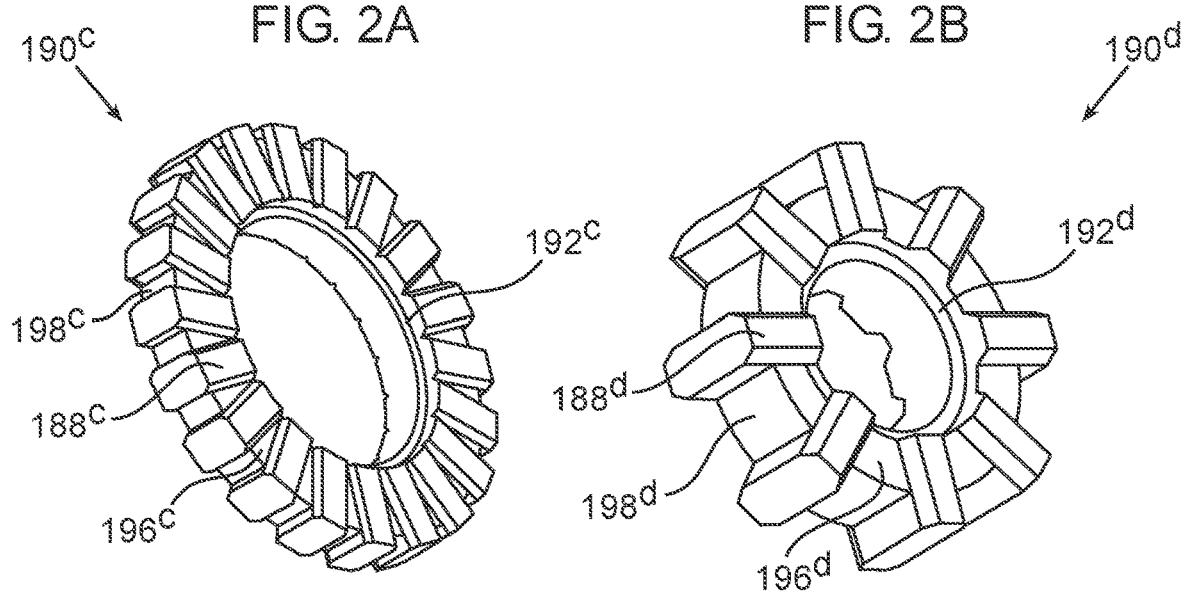

FIG. 2C illustrates an embodiments of a grabbing element $190^c$ provided with surface features $188^c$ in the form of radial extensions disposed along the grabbing element distal surface $196^c$, protruding distally therefrom, and disposed along the grabbing element circumferential surface $198^c$, protruding distally therefrom. FIG. 2D illustrates an embodiments of a grabbing element $190^d$ provided with surface features $188^d$ in the form of radial extensions that are spaced further apart from each other relative to surface features $188^c$, and that protrude further in the distal direction and the radial direction from grabbing element distal surface $196^d$ and from grabbing element circumferential surface $198^d$, respectively, relative to surface features $188^c$.

Figure 2E:
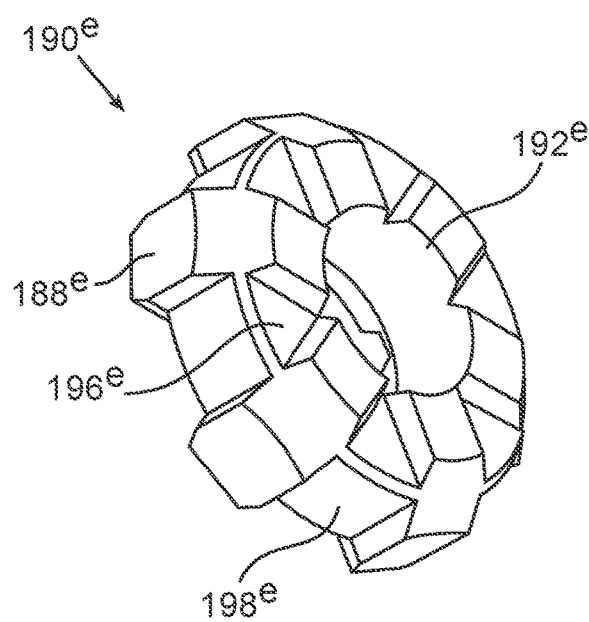

FIG. 2E illustrates an embodiments of a grabbing element $190^e$ provided with surface features $188^e$ in the form of radial extensions disposed along the grabbing element distal surface $196^e$, protruding distally therefrom, and disposed along the grabbing element circumferential surface $198^e$, protruding distally therefrom, chamfered along the transitional corners between the axial and radial protrusions.

Figure 2F:
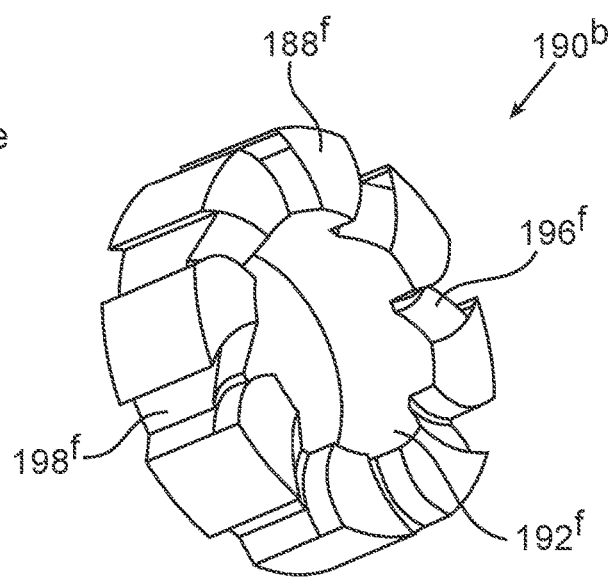

FIG. 2F illustrates an embodiments of a grabbing element $190^f$ provided with surface features $188^f$ in the form of circumferentially curved atraumatic saw-teeth disposed along the grabbing element distal surface $196^f$, protruding distally therefrom, and disposed along the grabbing element circumferential surface $198^f$, protruding distally therefrom.

The embodiments illustrated in FIGS. 2A-F show exemplary configurations. Alternative configuration will be apparent to those skilled in the art.

The surface features 188 are atraumatic surface features, configured to releasably engage a tissue without cutting it, dissecting it or penetrating it. For that end, the surface features 188 are formed as blunt and not sharp features. According to some embodiments, the grabbing element 190 is shaped as an atraumatic element, configured to engage a tissue without cutting, dissecting it or penetrating it. According to some embodiments, all of the edges of the grabbing element 190, including all of the edges of the surface features 188, are blunt and not sharp, e.g. rounded.

The term "releasably engage", with reference to the engagement between the atraumatic surface features 188 and the tissue they are in contact with, refers to the atraumatic surface features shaped so as to be able to grab and wrap the tissue when the grabbing element 190 is rotated around its central axis in one direction, yet the tissue may be released (i.e., disengaged or unwrapped) from the grabbing element 190 when the grabbing element 190 is rotated in the opposite direction, such that the tissue remains undamaged by the atraumatic surface features when released from engagement therefrom. The term "undamaged" refers to the tissue being uncut, without being dissected or penetrated through by the grabbing element 190.

The grabbing element 190 is configured to engage and grasp a tissue, without cutting or penetrating it, via the surface features 188, during rotation thereof. The surface features 188 are further configured to retain the tissue engaged with the grabbing element 190 once its rotational movement halts, that is to say that the tissue is prevented from slipping around the grabbing element 190 and disengaging therefrom after its rotation stops, unless the grabbing element is rotated in an opposite direction.

According to some embodiments, the surface features 188 comprise a rough surface, configured to engage and grasp a tissue by applying frictional forces during rotational movement of the grabbing element 190.

Advantageously, since the surface features 188 do not penetrate the tissue, rotation of the grabbing element 190 in an opposite direction to the direction of tissue engagement, enable easy, quick, convenient and safe tissue disengagement therefrom.

According to some embodiments, the grabbing element inner opening 192 is devoid of surface features 188, that is to say that the grabbing element inner opening 192 comprises a relatively smooth surface without extensions such as tabs, dimples, tines or the like, as the grabbing element inner opening 192 is not configured to grab tissue, but rather to provide access to other device that can pass there through towards and into tissue which is grabbed by surface features 188 along at least one of the grabbing element distal surface 196 or the grabbing element circumferential surface 198.

According to some embodiments, the surface features 188 are oriented either in an axial direction or radially outwards, but not radially inwards. That is to say that none of the surface features 188 are oriented towards each other.

According to some embodiments, at least one of the grabbing element distal surface 196 or the grabbing element proximal surface 194, is formed as a curved surface (embodiments not shown).

According to some embodiments, the grabbing element distal surface 196 is concave. According to some embodiments, both the grabbing element distal surface 196 and the grabbing element proximal surface 194 are concave. Such configurations advantageously form an atraumatic shape of the grabbing element 190.

According to some embodiments, both the grabbing element distal surface 196 and the grabbing element proximal surface 194 are convex.

Advantageously, curved surfaces, such as a convex or concave grabbing element distal surface 196, provide larger tissue grabbing area.

Figure 3A:
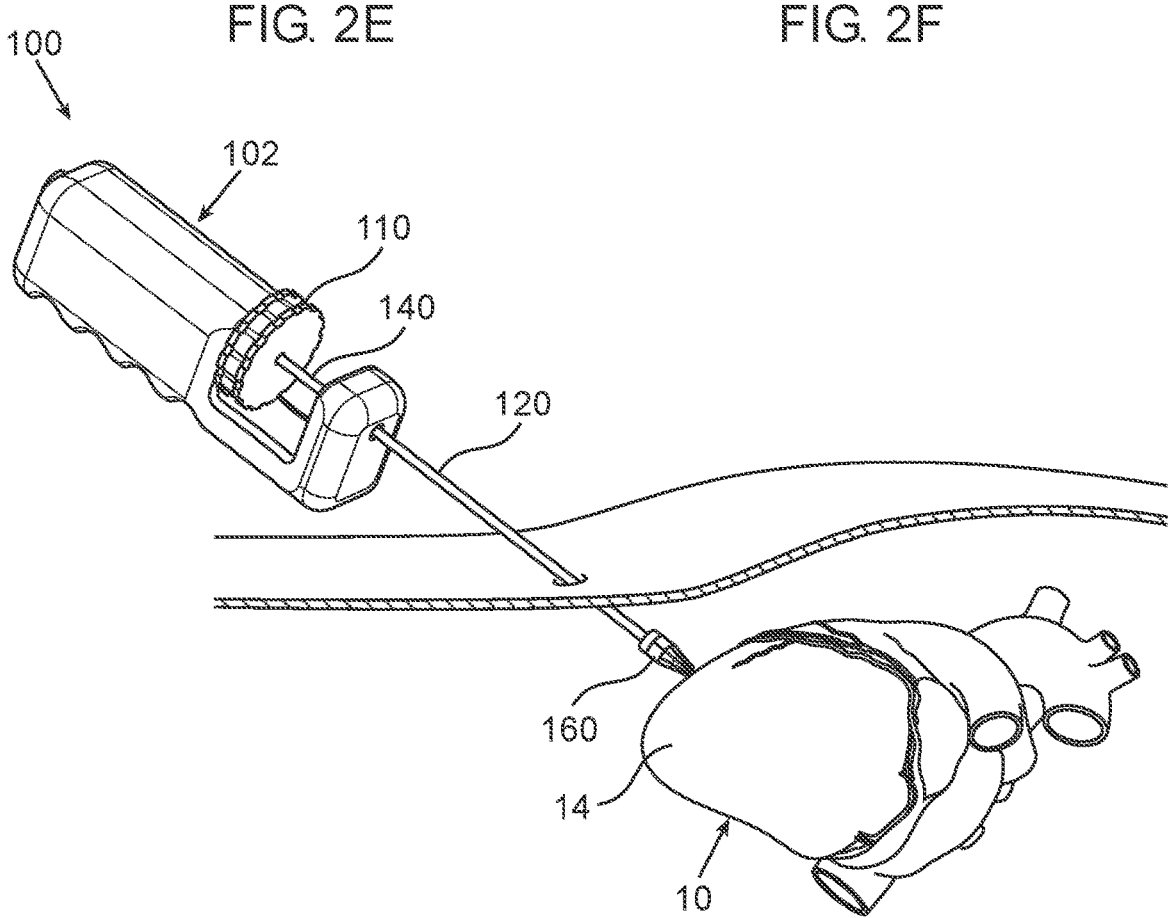
FIGS. 3A-3E illustrate different steps of a method of using the non-penetrating tissue separator, according to some embodiments.

Reference is now made to FIGS. 3A-3E, illustrating different steps of a method of using the non-penetrating tissue separator 100, according to some embodiments. FIG. 3A shows a first step of the method, wherein the distal region of the non-penetrating tissue separator 100, which includes at least a portion of the outer 120 and inner 140 shafts, the grabbing element 190 and the cone head 160, is inserted into a patient's body and advanced distally toward the heart 10 of the patient, while the non-penetrating tissue separator 100 is in a first state, that is to say while the grabbing element 190 is positioned proximal to the outer distal edge of the non-penetrating tissue separator 100.

When the outer distal edge approximates the heart 10, such that it is at or near the pericardium 14, the operator maneuvers the non-penetrating tissue separator 100 to deploy the grabbing element 190 from a first state to a second state. If the cone head 160 comprises a plurality of wings 170, they are expanded radially outwards during the displacement of the grabbing element 190 from the first state to the second state (see FIG. 3B). According to some embodiments, the grabbing element 190 is positioned in the second state such that it is distally spaced from the cone distal lip 174 (see FIG. 3B).

According to some embodiments, the grabbing element 190 is deployed from the first state to the second state by distally advancing the inner shaft 140 relative to the outer shaft 120, for example by rotating the steering knob 110. According to some embodiments, the grabbing element 190 is deployed from the first state to the second state by proximally retracting the outer shaft 120 relative to the inner shaft 140. According to some embodiments, the grabbing element 190 is deployed from the first state to the second state by pushing the inner shaft 140 in a distal direction, relative to the outer shaft 120.

If the grabbing element 190 is not yet in contact with the pericardium 14 after transitioning to the second state, it is advanced further in the distal direction to contact or press against the pericardium 14. When the grabbing element 190 is in contact with the pericardium 14, the operator maneuvers the non-penetrating tissue separator 100 to rotate the grabbing element 190 around its central axis. According to some embodiments, the rotation of grabbing element 190 is achieved by rotating the inner shaft 140.

According to some embodiments, the handle 102 further comprises a rotating knob (not shown), for example disposed within the first handle niche 108 or proximal to the handle proximal portion 106, fixedly attached to the inner shaft external surface 148, such that rotation of the rotating knob facilitates rotation of the inner shaft 140 and the grabbing element 190.

Figure 3B:
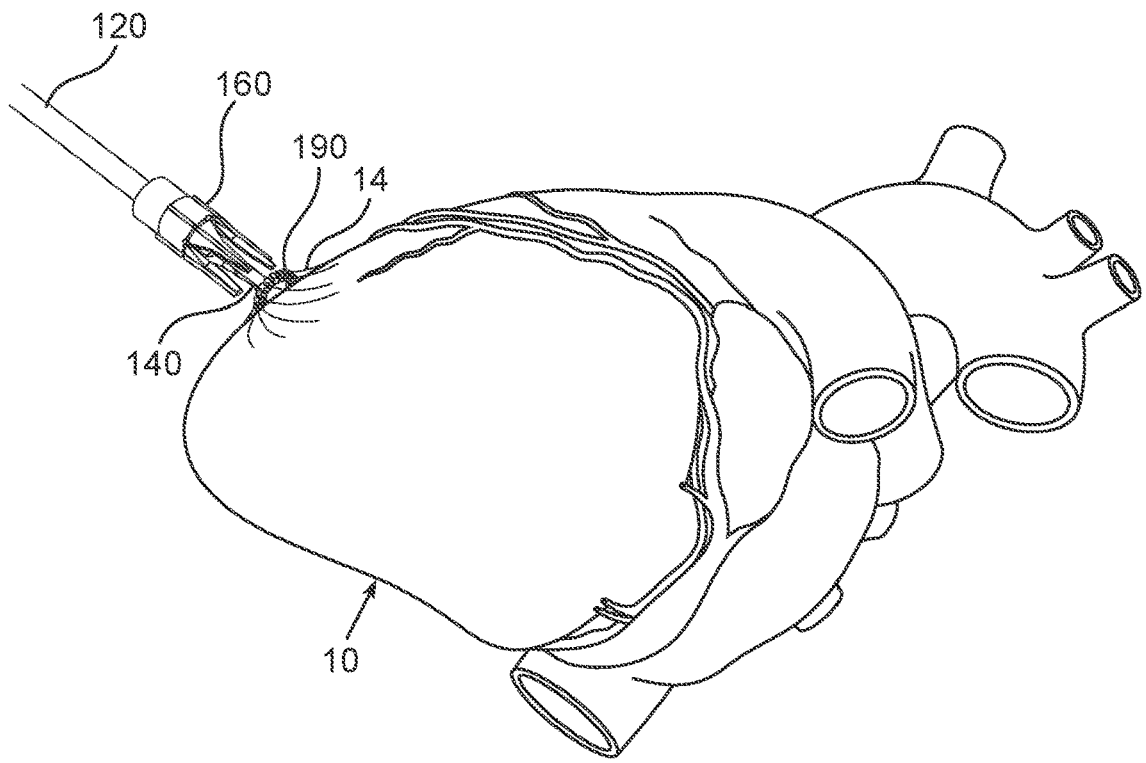

The tension applied to the pericardium 14 via the surface features 188 during the rotational movement of the grabbing element 190 causes the tissue to wrap around the grabbing element 190 as shown in FIG. 3B, without being cut or punctured thereby. The grabbing element 190 is rotated at least until the pericardium 14 is wrapped around at least a portion of the grabbing element circumferential surface 198. According to some embodiments, the grabbing element 190 is further rotated such that the pericardium 14 is wrapped around both the grabbing element circumferential surface 198 and the grabbing element proximal surface 194.

Once the tissue of the pericardium 14 is wrapped around the grabbing element 190, the operator maneuvers the non-penetrating tissue separator 100 to pull the grabbing element 190 in the proximal direction 94, thereby creating an access space or working space 16, formed between the proximal wrapped portion of the parietal pericardium 14 and the epicardial surface 12.

The terms "pericardium" and "parietal pericardium", as used herein, are interchangeable.

According to some embodiments, the entire non-penetrating tissue separator 100 is pulled in the proximal direction 94 in order to form the pericardial space 16, without relative movement between the inner shaft 140 and the outer shaft 120.

According to some embodiments, the pericardial space 16 is formed by pulling the inner shaft 140 in the proximal direction 94 relative to the outer shaft 120. According to some embodiments, the grabbing element 190 is pulled in a proximal direction 94 until the pericardium 14 wrapped there along is pressed between the grabbing element 190 and at least a portion of the cone head 160, thereby locking the wrapped pericardial tissue 14 there between.

Figure 3C:
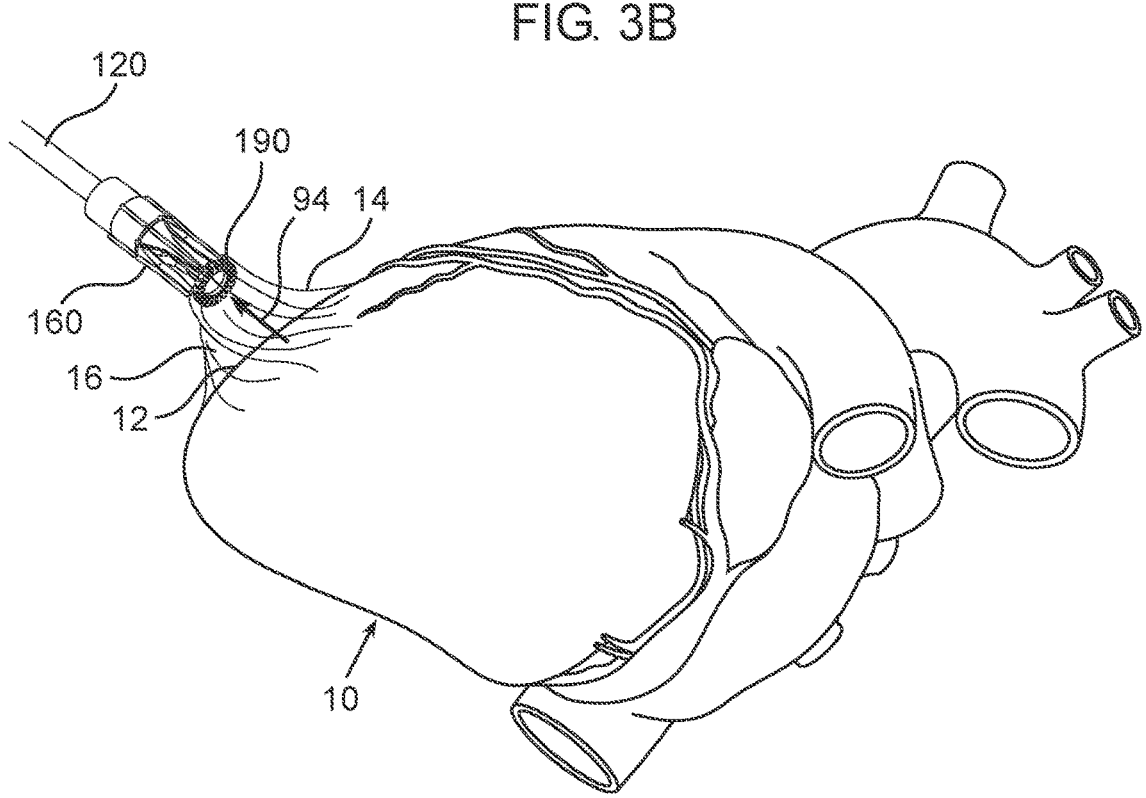

According to some embodiments, the wrapped pericardial tissue 14 is pressed between the grabbing element proximal surface 194 and the cone distal lip 174, as shown in FIG. 3C. According to some embodiments, the wrapped pericardial tissue 14 is pressed between the grabbing element circumferential surface 198 and the cone inner surface 178.

According to some embodiments, the grabbing element 190 is pulled in a proximal direction 94 until the pericardium 14 wrapped there along is pressed between the grabbing element 190 and at least a portion of the outer shaft 120, thereby locking the wrapped pericardial tissue 14 there between.

According to some embodiments, the wrapped pericardial tissue 14 is pressed between the grabbing element proximal surface 194 and the outer shaft distal lip 126. According to some embodiments, the wrapped pericardial tissue 14 is pressed between the grabbing element circumferential surface 198 and a portion of the outer shaft internal surface 130.

According to some embodiments, there is provided a kit comprising the non-penetrating tissue separator 100 and an access device, configured to either puncture, cut or penetrate the pericardium 14 in order to provide access to the working space 16. According to some embodiments, the access device is sized and shaped to be passable through the inner shaft lumen 152 and out of the grabbing element inner opening 192.

Figure 3D:
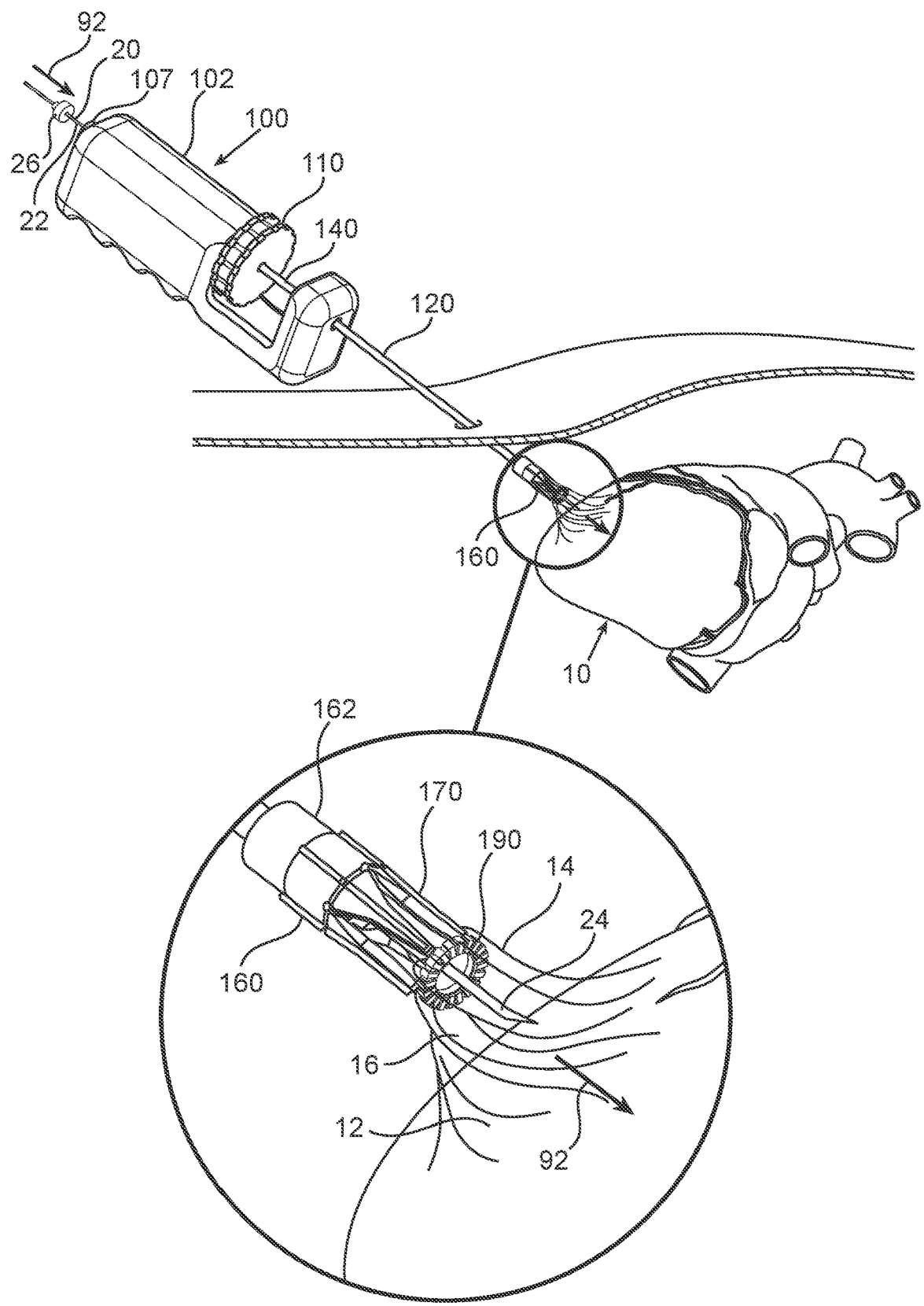

According to some embodiments, the access device comprises a needle 20, the needle comprising a needle shaft with a proximal needle portion 22, and a sharp distal needle portion 24. FIG. 3D shows a step of advancing the distal needle portion 24 in direction 92 to puncture the portion of the pericardium 14 extending along the grabbing element inner opening 192, thereby providing access to the working space 16.

According to some embodiments, the pericardium 14 is wrapped around the grabbing element 190 such that it is stretched against the grabbing element inner opening 192, thereby enabling easier puncturing thereof.

According to some embodiments, the proximal needle portion 22 comprises a needle restraining element 26, configured to abut against a portion of the handle proximal portion 104, such as the handle inlet 107. According to some embodiments, the needle restraining element 26 is provided with an external diameter larger than internal diameter of the handle inlet 107, thereby preventing further distal advancement of the needle 20 to limit its penetration depth and avoid puncturing the epicardial surface.

Figure 27A:
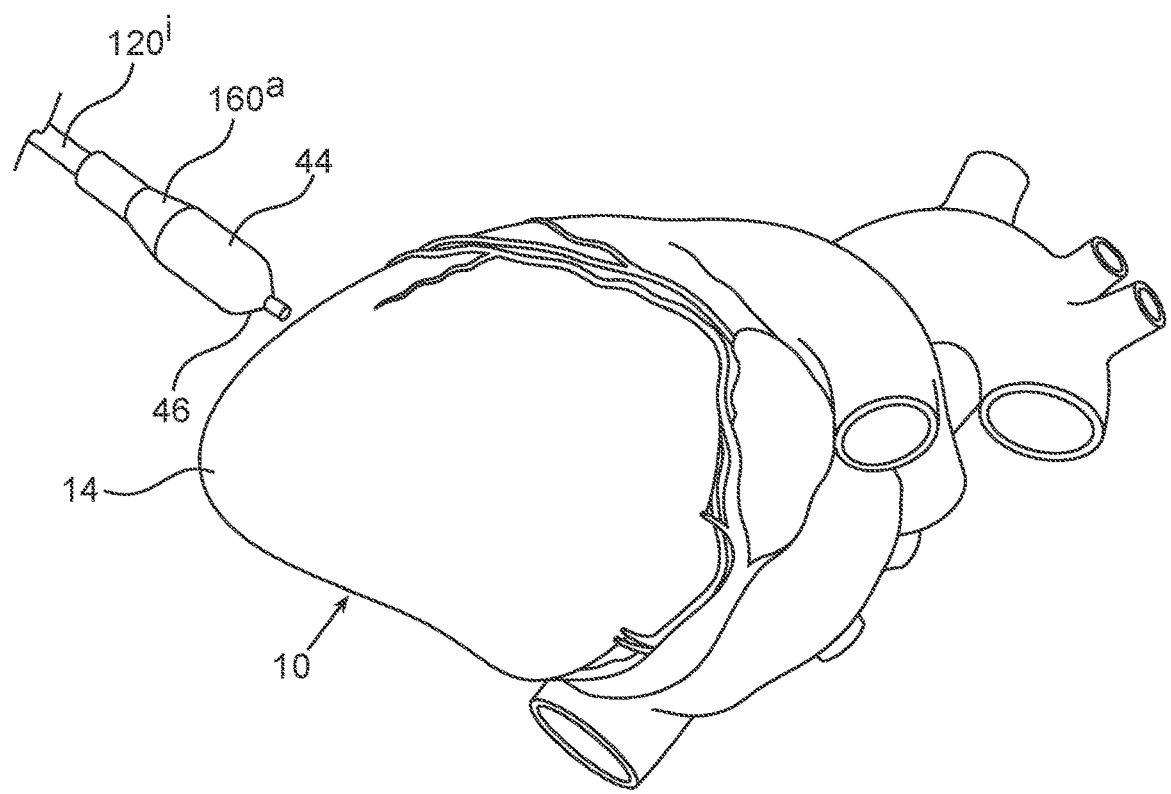
FIGS. 27A-27D illustrate different steps of a method of using the non-penetrating tissue separator, according to some embodiments.
Figure 27B:
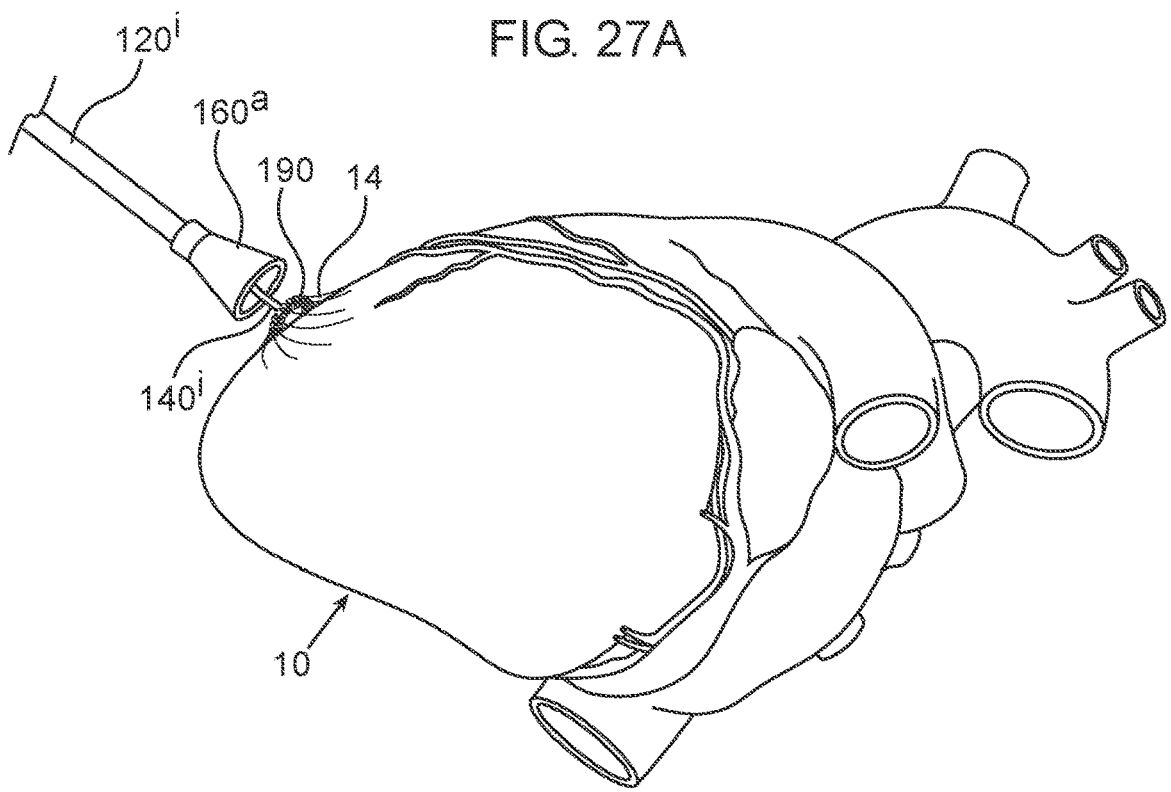
Figure 27C:
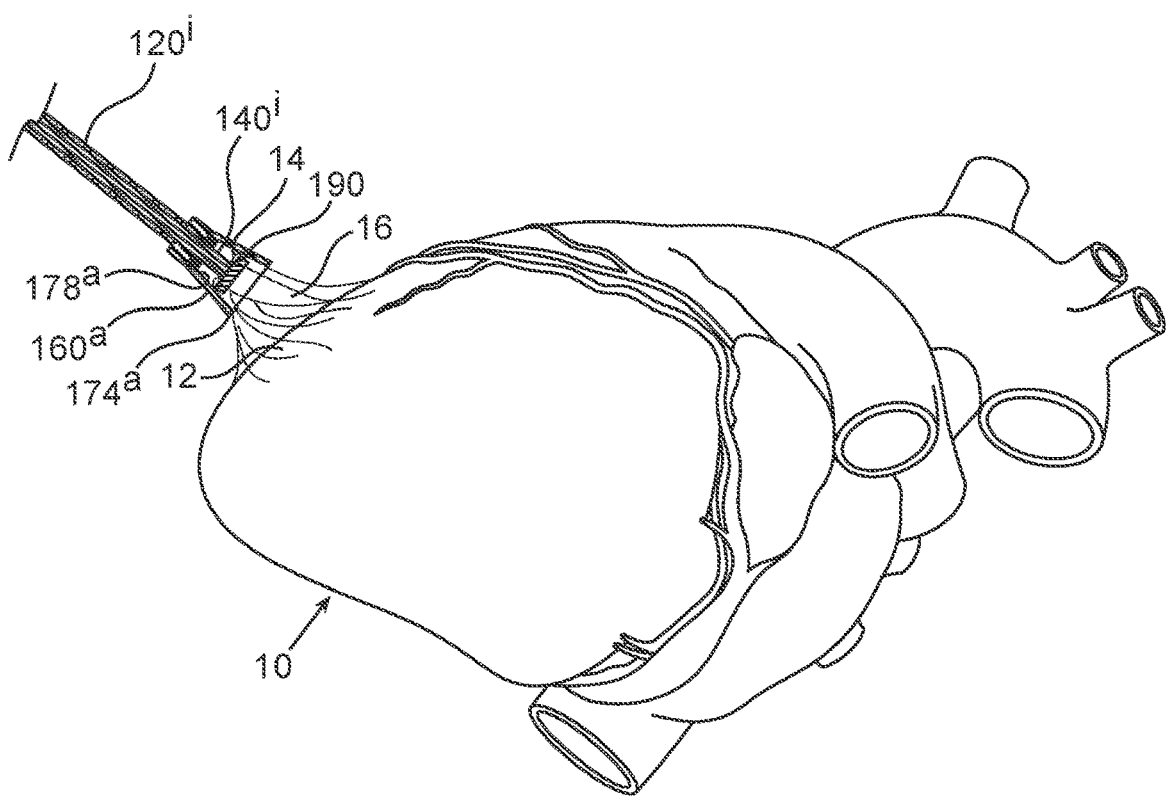
Figure 27D:
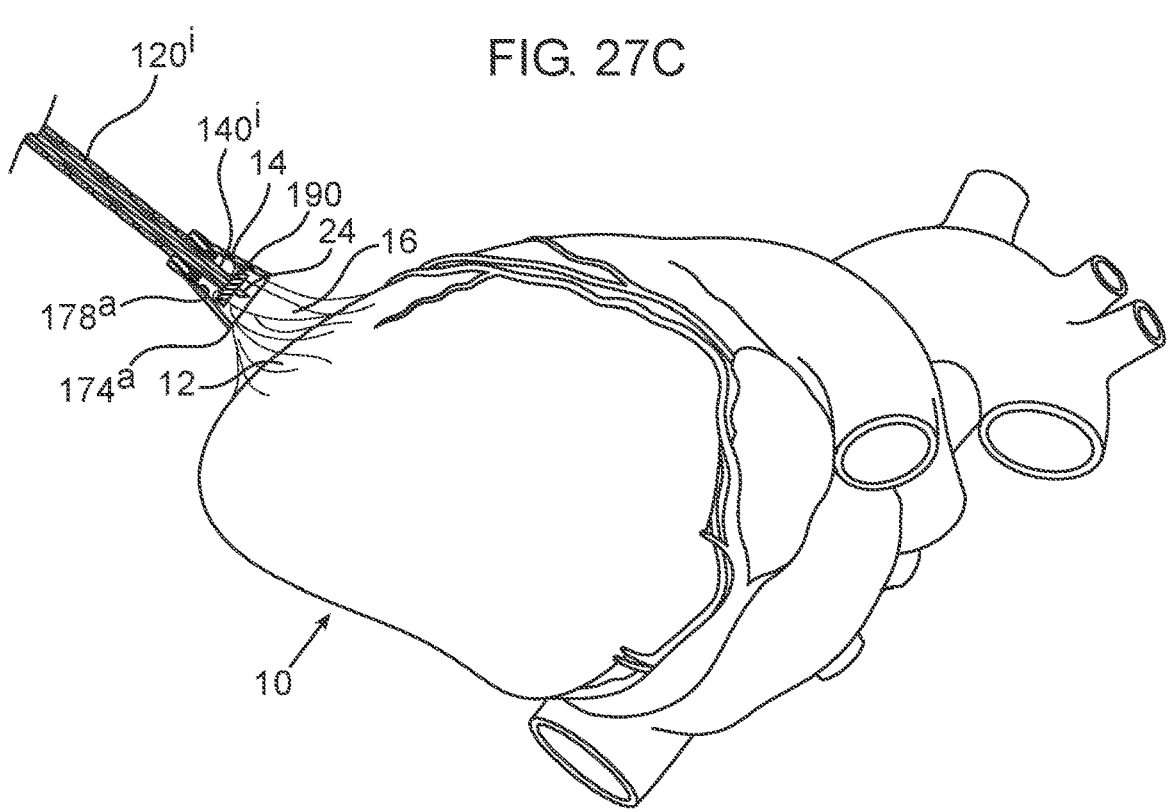

While the needle 20 in FIG. 3D is shown to penetrate the pericardial space 16, such that the distal tip of the needle 20 extends distally beyond the grabbing element 190, according to some embodiments, the needle is prevented from moving distally beyond the cone distal lip 174 (see FIG. 27D).

According to some embodiments, the distal needle portion 24 is bent or curved to a point that the direction of the sharp tip of the distal needle portion 24 is offset from the longitudinal axis or centerline of the needle shaft (see FIG. 3D). Such embodiments can advantageously provide perpendicular access of the distal needle portion 24 towards either the pericardium 14 or other tissues of interest, whenever the distal portion of the non-penetrating tissue separator 100 is angled relative thereto. Advantageously, a curved/bent distal needle portion 24 further supports either anterior or posterior approach thereof.

Other types of an access device can be provided in the kit. International application publication WO 2018/235072 to the inventors, discloses an accessing device comprising a thread having a circumferentially oriented sharp end, configured to puncture or penetrate the pericardium from a lateral direction during rotation thereof. Such an accessing device can be utilized instead of a needle. According to some embodiments, the access device provided in the kit along with the non-penetrating tissue separator 100 is in the form of the accessing device disclosed in WO 2018/235072.

According to some embodiments, an access device having a distal puncturing element, such as a distally oriented sharp tip formed at the distal end of a circumferential thread, can be provided in the kit. Such an access device can be delivered to the pericardium 14 through the inner shaft lumen 152, utilized to puncture the pericardium 14 retained by the non-penetrating tissue separator 100 for example by rotating it to promote puncturing thereof by the distally oriented sharp tip.

Figure 3E:
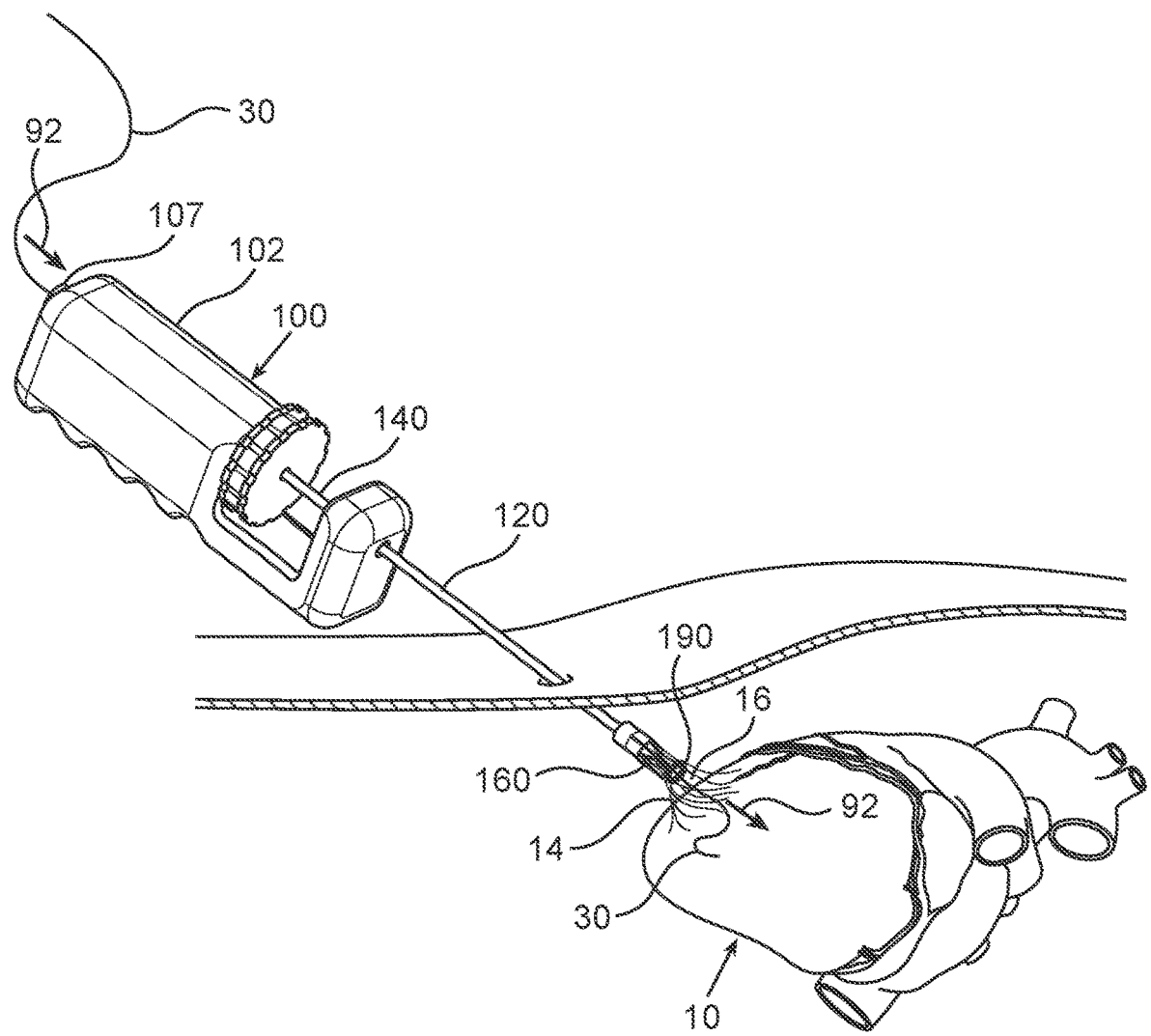

According to some embodiments, there is provided a kit comprising the non-penetrating tissue separator 100, an access device and a guidewire. FIG. 3E shows a further step of introducing a guidewire 30 through the incision or puncturing hole formed in the pericardium by the access device, into the working space 16. According to some embodiments, the guidewire 30 is advance through a lumen of the access device, such as a lumen of the needle 20.

According to some embodiments, once the incision or puncturing hole is formed in the pericardium, the access device, such as the needle 20, is retracted and removed from the non-penetrating tissue separator 100. According to some embodiments, the guidewire 30 is advance through the inner shaft lumen 152 and the grabbing element inner opening 192.

According to some embodiments, the non-penetrating tissue separator 100 further comprises a coupling such as a Luer lock, proximal to the handle proximal portion 104, for providing access to external devices such as the guidewire 30. According to some embodiments, the Luer lock is attached to the handle inlet 107 (embodiments not shown).

The terms "centerline", "central axis" or "longitudinal axis" of an element, as used herein, are interchangeable and refer to a set of centroids of all cross-sections of the element. The centerline may curve, such that its orientation varies along its length. The "local" centerline refers to the tangent to the centerline at or generally near the point of interest.

According to some embodiments, any one of the outer shaft 120, the inner shaft 140 or the cone head 160 can be made from a lubricious or low friction material, or can have an outer layer (along the respective outer surfaces) made from a lubricious or low friction material, such as PTFE.

According to some embodiments, there is provided a non-penetrating tissue separator 100 comprising a cone head 160″ threadedly engaged with a threaded grabbing element 190″ (embodiments not shown). The cone head 160″ comprises a plurality of wings 170″, oriented in a distal axial direction, separated by notches there between. Each wing 170″ comprises a wing distal lip 172″, wherein the plurality wing distal lips 172″ together form the cone distal lip 174″. At least a portion of the cone inner surface 178″, for example formed by at least a portion of the inner surfaces of the wings 170″, comprises an inner thread.

The grabbing element circumferential surface 198″ comprises an outer thread matching the inner thread of the cone head 160″. The outer thread of the grabbing element 190″ is engaged with the inner thread of the cone head 160″. According to some embodiments, the cone head 160″ is provided with its wings 170″ in an un-expanded state (similar to the state of wings 170 in FIG. 1C) when the grabbing element 190″ is in the first state, and configured to expand when the grabbing element 190″ threadedly propagates distally to the second state.

In use, when the grabbing element 190″ is rotated in one direction during propagation thereof in the distal direction, the rotational threaded engagement promotes radial expansion of the wings 170″. According to some embodiments, the wings 170″ are provided with inclined or slanted inner surfaces, configured to promote a desired radial expansion thereof during threaded movement of the grabbing element 190″ there along. According to some embodiments, the wings 170″ are further configured to contract radially inwards when the grabbing element 190″ is retracted proximally towards the first state.

According to some embodiments, the advancement and operation of at least some, and potentially all of the steps of using the non-penetrating tissue separator 100, are facilitated by at least one imaging or sensing device. According to some embodiments, the non-penetrating tissue separator 100 comprises at least one sensor to facilitate at least one functionality thereof (embodiments not shown).

According to some embodiments, the non-penetrating tissue separator 100 comprises at least one optical sensor. According to some embodiments, the non-penetrating tissue separator 100 comprises at least one impedance sensor. According to some embodiments, the non-penetrating tissue separator 100 comprises at least one ultrasound sensor.

According to some embodiments, non-penetrating tissue separator 100 comprises at least one mechanical sensor, such as a spring-based sensor.

According to some embodiments, the non-penetrating tissue separator 100 comprises at least one electrical sensor, such as an ECG electrode, configured to be in electrical communication with an ECG monitor. The sensor may serve as an electrode to sense and record electrical signals in the cardiac tissue. In such embodiments, the ECG monitor may provide feedback to an operator of the non-penetrating tissue separator 100, facilitating operation thereof. According to some embodiments, ECG monitor may provide feedback regarding the current position of a specific portion or element of the non-penetrating tissue separator 100.

Figure 4A:
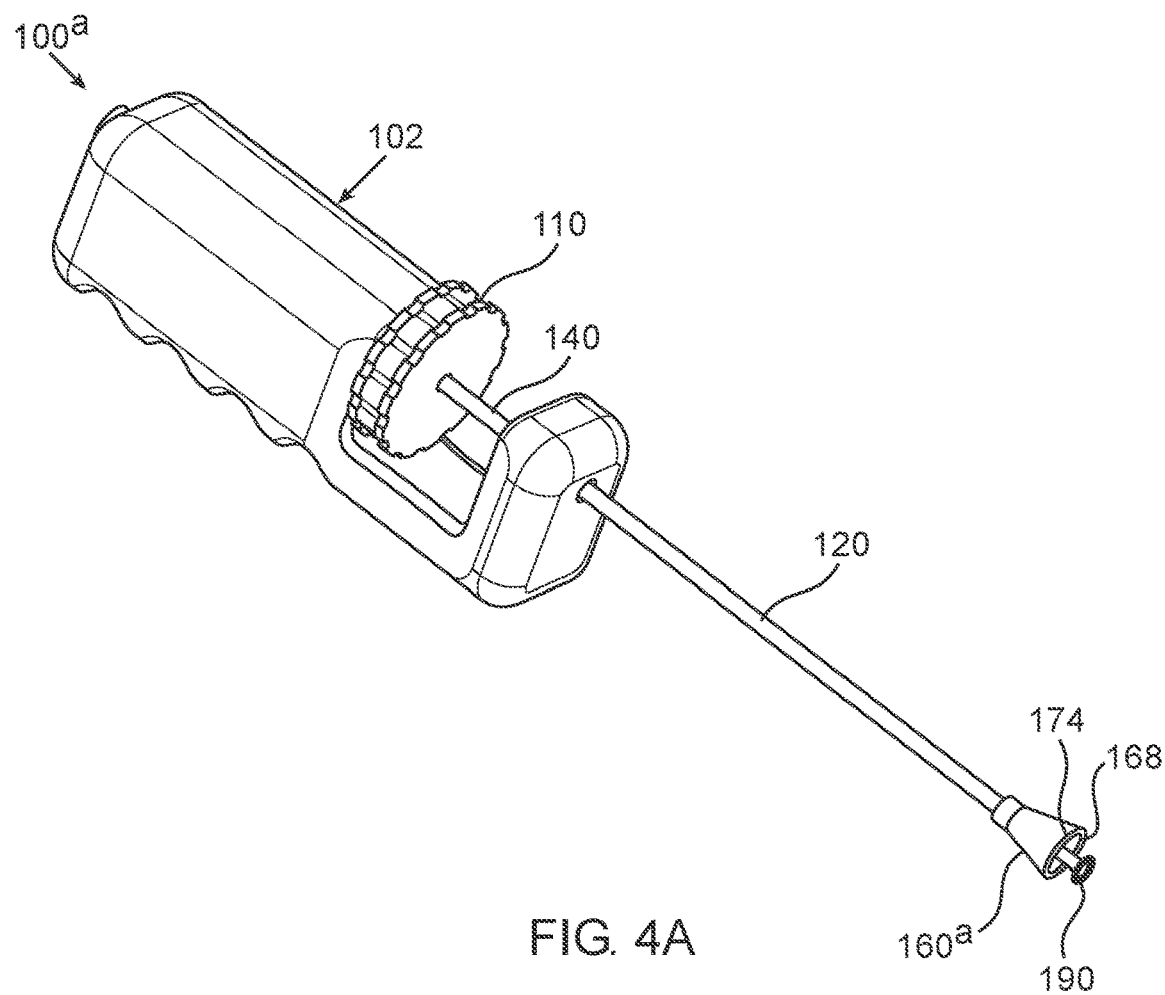
FIG. 4A constitutes a view in perspective of a non-penetrating tissue separator, according to some embodiments.
Figure 4B:
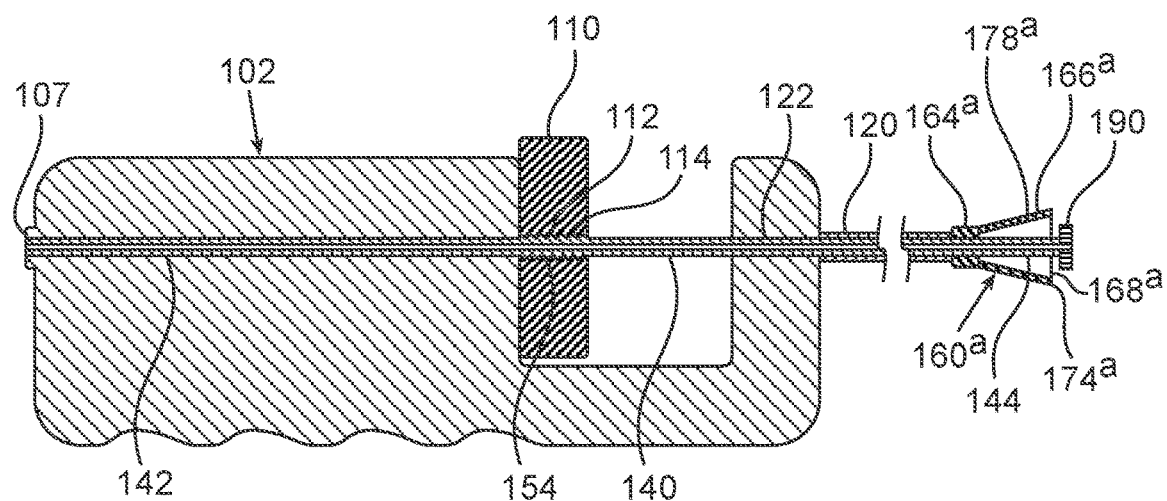
FIG. 4B constitutes a cross-sectional side view of the non-penetrating tissue separator of FIG. 4A.

Reference is now made to FIGS. 4A-4B. FIGS. 4A and 4B constitute a view in perspective and a cross-sectional side view, respectively, of a non-penetrating tissue separator $100^a$ according to some embodiments. The non-penetrating tissue separator $100^a$ is similar to the non-penetrating tissue separator 100 described herein above, except that the cone head $160^a$ is devoid of expandable wings.

Specifically, the cone head $160^a$ is formed as a rigid non-deformable structure, comprising a cone proximal portion $164^a$ attached to the outer shaft distal portion 124, and a cone distal portion $166^a$ extending distally therefrom, tapering radially outwards such that the diameter of its cone opening $168^a$ is larger than the diameter of the outer shaft 120. The cone head $160^a$ functions and includes all of the embodiments described herein above for cone head 160 that do not refer to the relative movement or operation of wings 170.

Figure 5A:
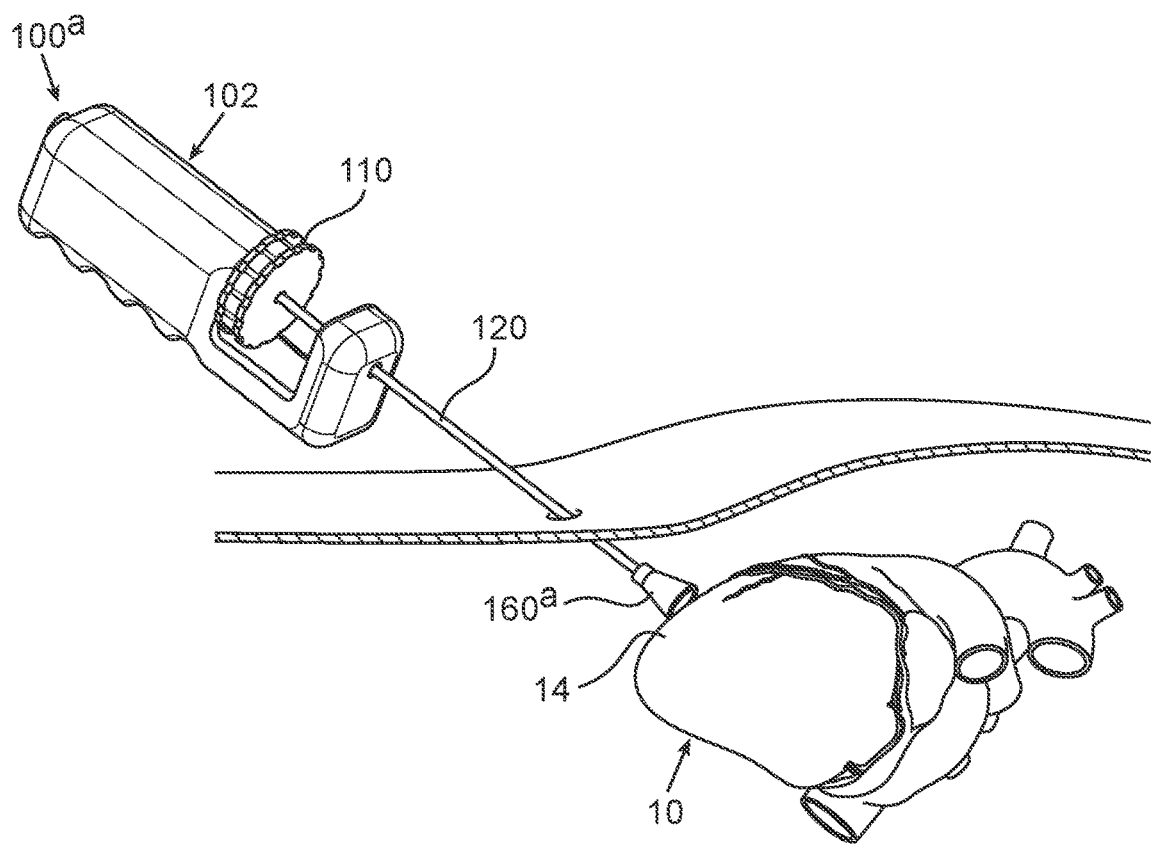
FIGS. 5A-5D illustrate different steps of a method of using the non-penetrating tissue separator, according to some embodiments.

Reference is now made to FIGS. 5A-5D, depicting different steps of a method of using the non-penetrating tissue separator $100^a$, according to some embodiments. FIG. 5A shows a first step of the method, wherein the distal portion of the non-penetrating tissue separator 100, including at least a portion of the outer 120 and inner 140 shafts, the grabbing element 190 and the cone head $160^a$, is inserted into the patient and advanced distally toward the heart 10 of the patient, while the non-penetrating tissue separator $100^a$ is in a first state, that is to say while the grabbing element 190 is positioned proximal to cone distal lip $174^a$.

When the outer distal edge approximates the heart 10, such that it is at or near the pericardium 14, the operator maneuvers the non-penetrating tissue separator $100^a$ to deploy the grabbing element 190 from a first state to a second state. According to some embodiments, the grabbing element 190 is positioned in the second state such that it is distally spaced from the cone distal lip $174^a$ (see FIG. 5B).

The grabbing element 190 is distally advanced in the second state to contact the pericardium 14. When the grabbing element 190 is at the pericardium 14, the operator maneuvers the non-penetrating tissue separator $100^a$ to rotate the grabbing element 190 around its central axis.

Figure 5B:
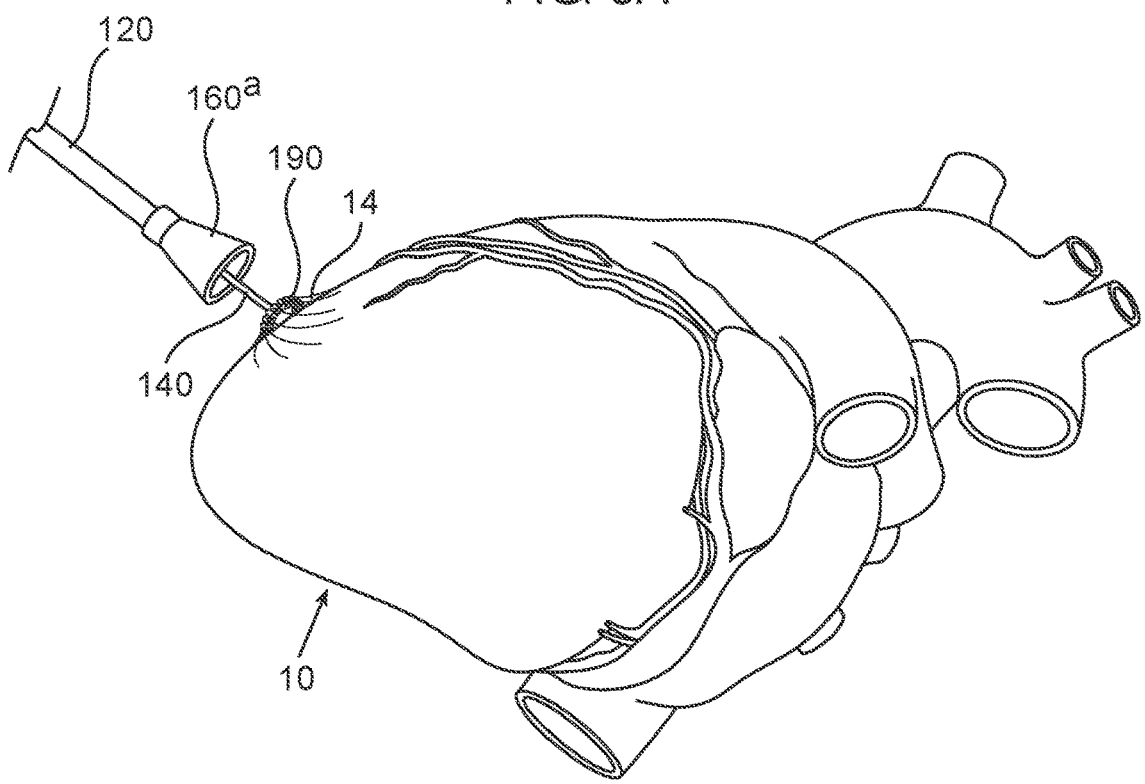

The surface features 188, during the rotational movement of the grabbing element 190, cause the tissue to wrap around the grabbing element 190 as shown in FIG. 5B, without being cut or punctured thereby. Once the tissue of the pericardium 14 is wrapped around the grabbing element 190, the operator maneuvers the non-penetrating tissue separator $100^a$ to pull the grabbing element 190 in the proximal direction to create the working pericardial space 16 (see FIG. 5C).

According to some embodiments, the grabbing element 190 is pulled in a proximal direction 94 until the pericardium 14 wrapped there along is pressed between the grabbing element 190 and at least a portion of the cone head $160^a$, thereby locking the wrapped pericardial tissue 14 there between.

Figure 5C:
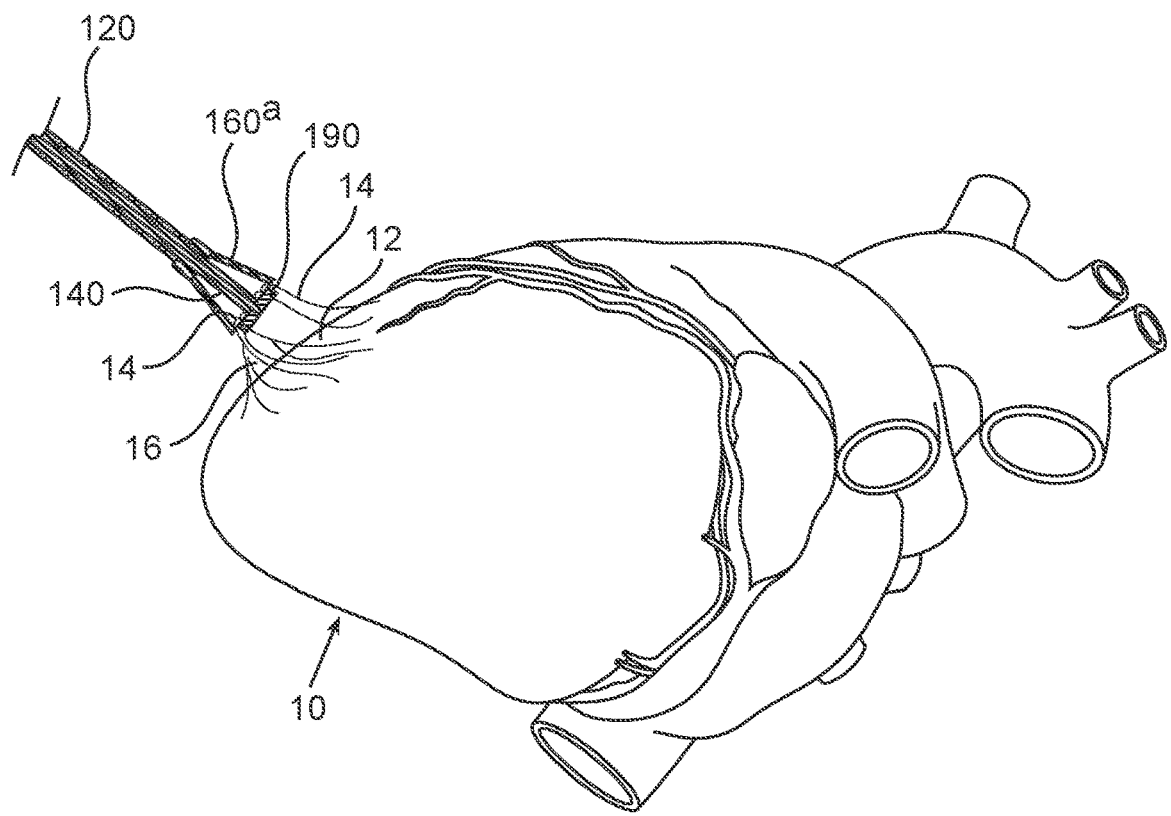

According to some embodiments, the wrapped pericardial tissue 14 is pressed between the grabbing element proximal surface 194 and the cone distal lip $174^a$, as shown in FIG. 5C. According to some embodiments, the wrapped pericardial tissue 14 is pressed between the grabbing element circumferential surface 198 and the cone inner surface $178^a$, as shown both in FIGS. 5C and 5D.

According to some embodiments, the grabbing element 190 is pulled in a proximal direction 94 until the pericardium 14 wrapped there along is pressed between the grabbing element 190 and at least a portion of the outer shaft 120, thereby locking the wrapped pericardial tissue 14 there between.

Figure 5D:
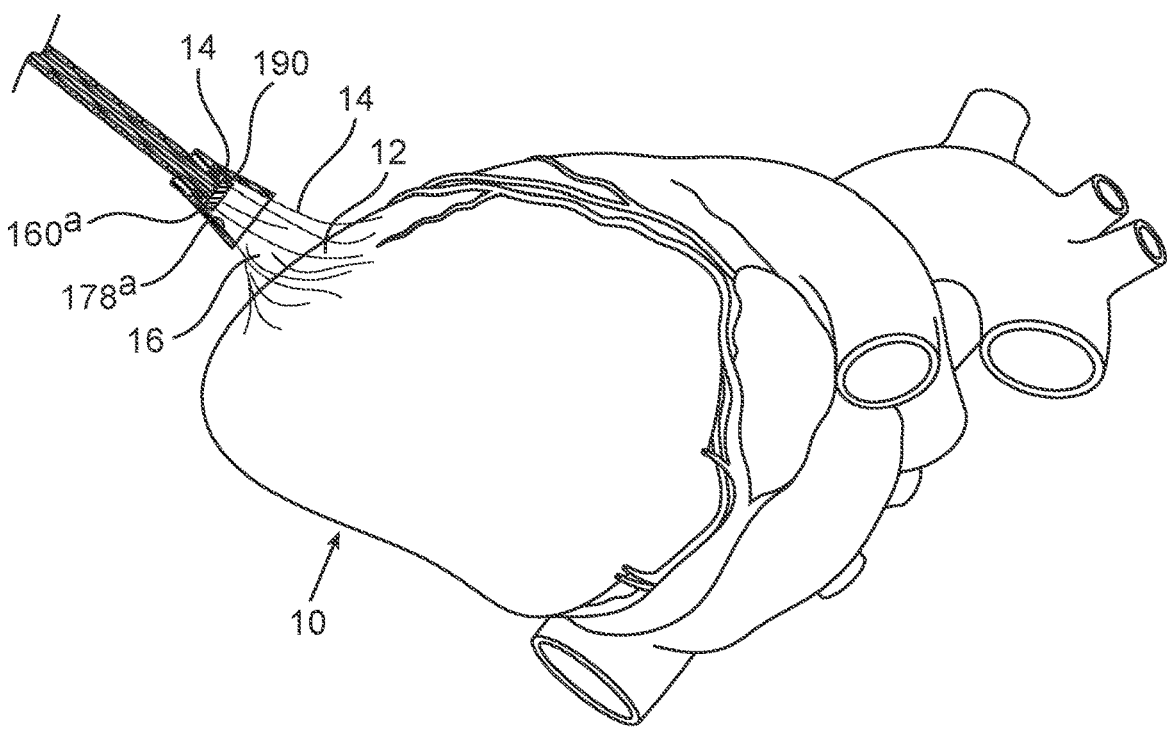

According to some embodiments, the wrapped pericardial tissue 14 is pressed between the grabbing element proximal surface 194 and the outer shaft distal lip 126, as shown in FIG. 5D.

According to some embodiments, there is provided a method of using the non-penetrating tissue separator 100, wherein the operator maneuvers the non-penetrating tissue separator 100 to deploy the grabbing element 190 from a first state to a second state prior to insertion thereof into the patient's body. The distal portion of the non-penetrating tissue separator 100, including at least a portion of the outer 120 and inner 140 shafts, the cone head $160^a$ and the grabbing element 190 in the second state, is then inserted into the patient and advanced distally toward the heart 10 of the patient, The rest of the steps are similar to those described for FIGS. 5B-5D herein above.

Figure 6A:
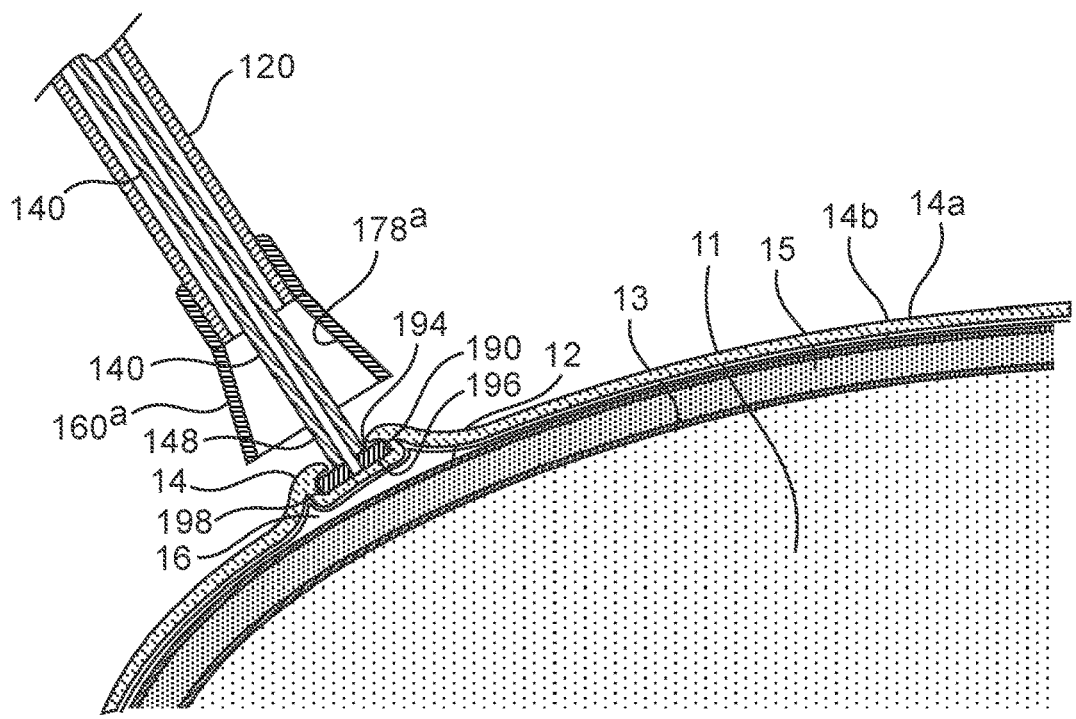
FIGS. 6A-6B constitute zoomed in cross-sectional side views of different steps of separating between the anatomical heart tissues, according to some embodiments.
Figure 6B:
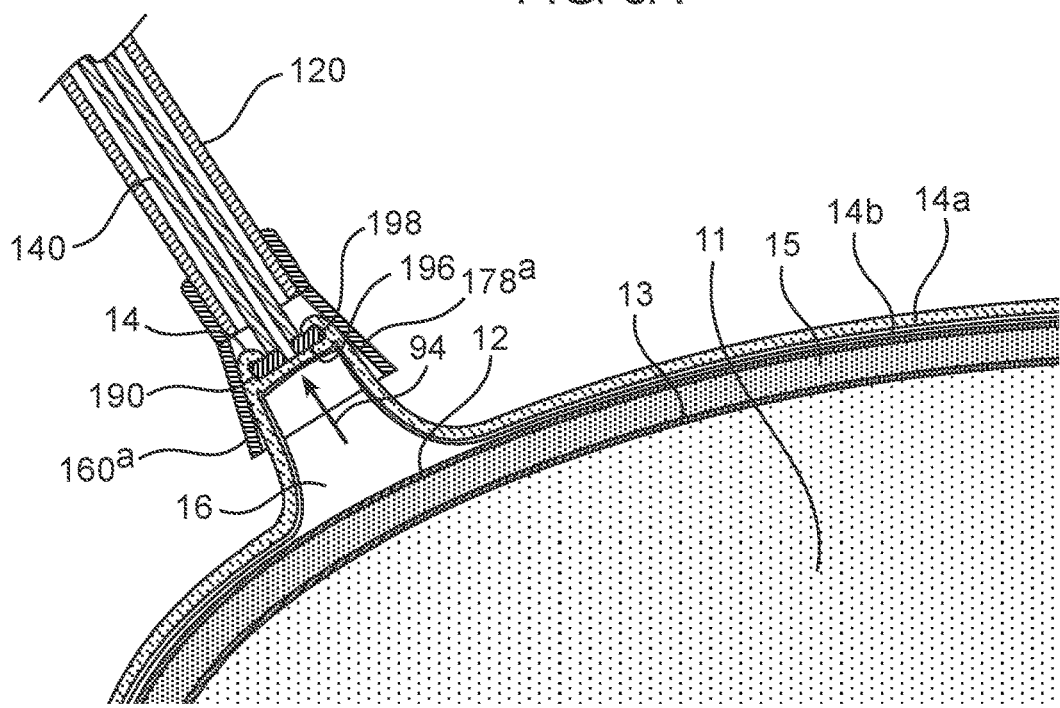

Reference is now made to FIGS. 6A-6B. FIGS. 6A and 6B constitute zoomed-in cross-section views of the distal region of the non-penetrating tissue separator 100 and the corresponding anatomical heart tissues, at two consecutive steps of the creation of the pericardial space 16. The heart chamber 11 is surrounded by several layers of tissue. The pericardial space 16 is formed by utilizing the non-penetrating tissue separator 100 to further separate a pre-existing narrower cavity between the heart wall and the pericardium 14. The heart wall, overlaying the chamber 11, includes several tissue layers: the endocardium 13, the myocardium 15, and the epicardium 12. The pericardium 14 itself is also composed of a fibrous pericardial tissue 14a overlaying the pericardial parietal layer 14b.

Normally, the pericardium 14 and the heart wall lie in close contact, separated only by a thin layer of pericardial fluid. When the grabbing element 190 is advanced to contact the pericardium 14 and then rotated about its centerline, the pericardium 14, including both the fibrous 14a and parietal 14b layers, is wrapped around it. In the exemplary embodiments illustrated in FIG. 6A, the pericardium 14 is wrapped around the grabbing element 190 such that it is engaged the grabbing element distal surface 196, the grabbing element circumferential surface 198, and the grabbing element proximal surface 194. In other embodiments, the grabbing element 190 can be rotated such that the pericardium 14 is engaged with and wrapped around only one or some of its surfaces, such as the grabbing element distal surface 196 and the grabbing element circumferential surface 198.

The separation between the layers is achieved by pulling the grabbing element 190 in a proximal direction 94 at this point, thereby distancing the pericardium 14 distally away from the heart wall, and specifically distancing the pericardial parietal layer 14b from the epicardial surface 12, to create an enlarged pericardial space 16 there between.

According to some embodiments, the grabbing element 190 is pulled until it can no longer move in the proximal direction 94 under conventional pull force applied thereto, such as manual pull force exerted by an operator of the non-penetrating tissue separator 100.

In the exemplary embodiment illustrated in FIG. 6B, the grabbing element 190 is retracted until the pericardium 14 is pressed between the grabbing element circumferential surface 198 and the cone inner surface 178$^a$.

In other embodiments, the grabbing element 190 is pulled until the pericardium 14 is pressed between at least one or some of the surfaces of the grabbing element 190 and at least one or some of: the cone distal lip 174, the cone inner surface 178, the outer shaft distal lip 126 and the outer shaft internal surface 130.

Advantageously, the procedure of grabbing the pericardium 14 and pulling it in a proximal direction 94 to create an enlarged pericardial space 16 is performed without cutting or perforating any of the tissues, including the pericardium 14 or any tissue of the heart wall, such as the epicardium 12, the myocardium 15 and the endocardium 13.

It will be clear that while other figures of the current specification, such as FIGS. 3B-E, 10A-C, 19A-C, 21A-C, 27A-D, 29A-B and 33A-B may illustrate a pericardial space 16 formed between the pericardium 14 and the epicardial surface 12 for simplicity, the pericardium 14 represents both the fibrous 14$a$ and parietal 14$b$ layers as shown in FIGS. 6A-B, and the epicardial surface 12 represents a layer overlaying the other layers of the heart wall, including the endocardium 13 and the myocardium 15 as shown in FIGS. 6A-B.

According to some embodiments, the non-penetrating tissue separator 100 does not necessarily include a cone head 160. Reference is now made to FIGS. 7A-10C, illustrating embodiments of a non-penetrating tissue separator 100 devoid of a cone head 160.

Figure 7A:
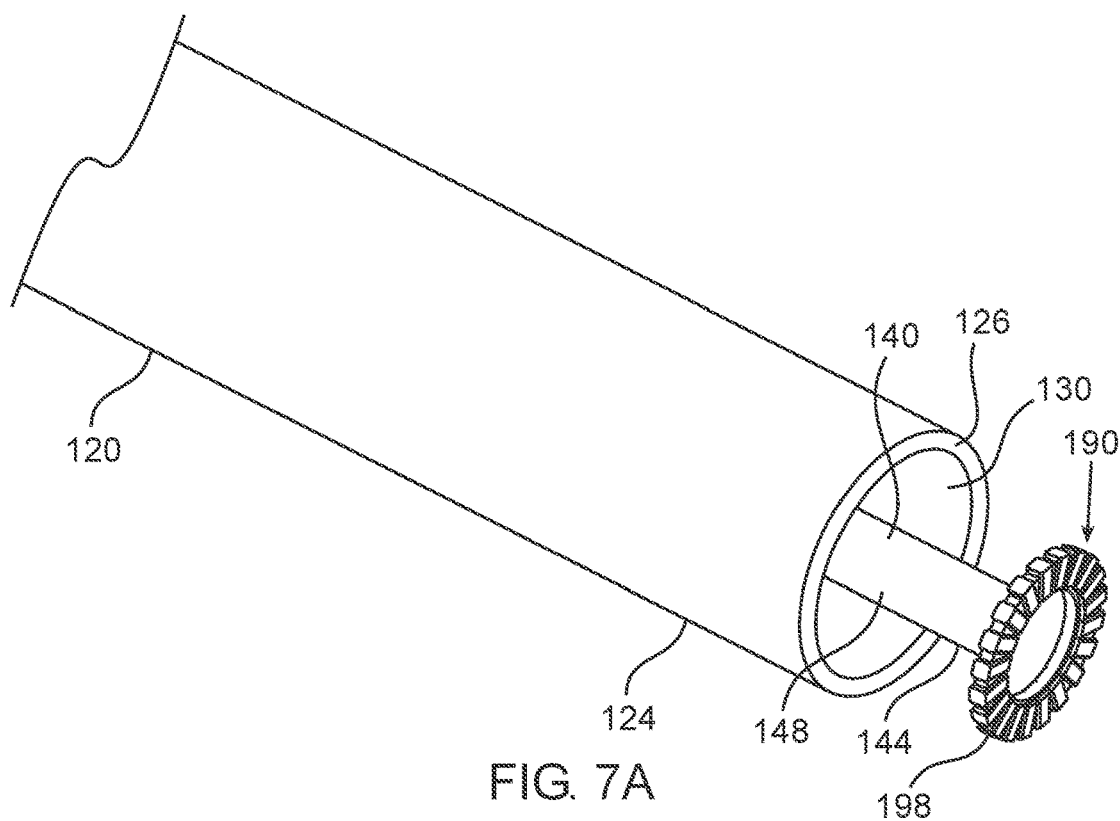
FIG. 7A constitutes a zoomed-in view in perspective of the distal region of the non-penetrating tissue separator devoid of a cone head, according to some embodiments.
Figure 7B:
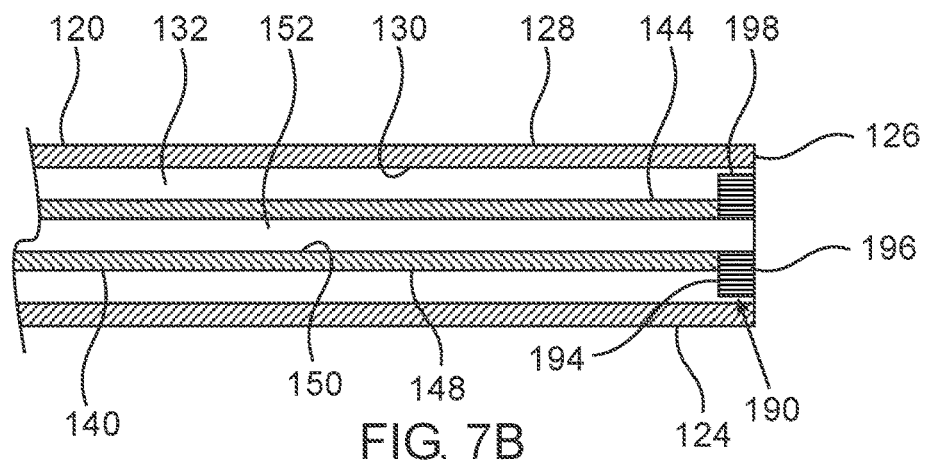
FIG. 7B constitutes a cross-sectional side view of the distal region of the non-penetrating tissue separator of FIG. 7A, in a first state.
Figure 7C:
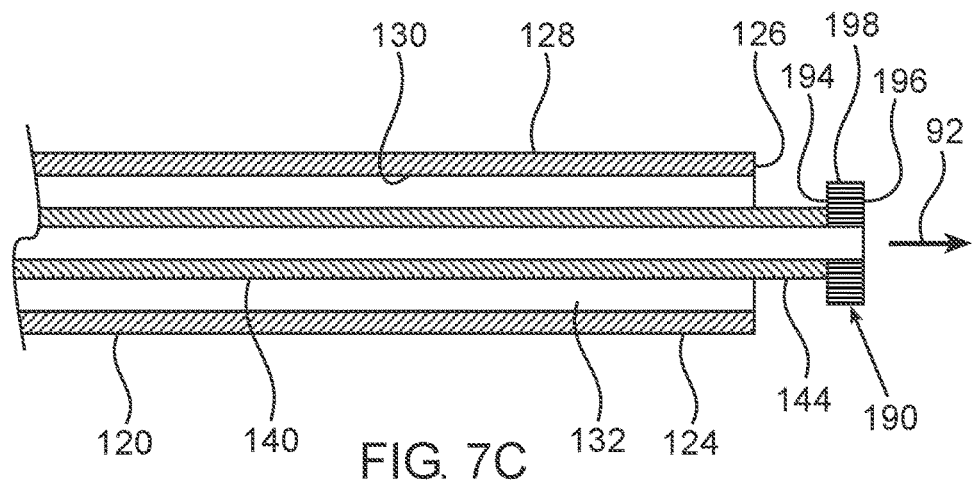
FIG. 7C constitutes a cross-sectional side view of the distal region of the non-penetrating tissue separator of FIG. 7A, in a second state.

FIG. 7A constitutes a view in perspective of a non-penetrating tissue separator 100 according to some embodiments. FIGS. 7B and 7C constitute cross-sectional side views in a first state and a second state, respectively, of the non-penetrating tissue separator 100 of FIG. 7A. Aside from the absence of a cone head 160, the non-penetrating tissue separator 100 includes all other components, similar in structure and function, disclosed throughout the current specification.

According to some embodiments, the outer diameter of the grabbing element 190 is smaller than the diameter of the outer shaft lumen 132, such that the grabbing element 190 can be inserted into the outer shaft lumen 132. In such embodiments, the outer shaft distal lip 126 serves as the outer distal edge. FIG. 7B illustrates the grabbing element 190 positioned in a first state, such that the distal surface 196 of the grabbing element 190 is proximal to or flush with the outer shaft distal lip 126.

According to some embodiments, the non-penetrating tissue separator 100 further comprises an inner shaft retraction limiting mechanism, configured to limit the maximal retraction of the grabbing element 190 in a proximal direction up to a specific position, for example in order to limit the movement of the grabbing element 190 from advancing proximally too far away into the outer shaft lumen 132 (embodiments not shown). This may be beneficial to ensure that the grabbing element 190 is either flush with or distanced only a relatively short desired distance from the outer shaft distal lip 126 in a first position.

An exemplary inner shaft retraction limiting mechanism may include, by way of example, and outer protrusion extending radially outwards from the inner shaft external surface 148, positioned distal to and configured to engage a corresponding inner protrusion extending radially inwards from the outer shaft internal surface 130, thereby preventing either further proximal movement of the inner shaft 140 relative to the outer shaft 120, or preventing further distal movement of the outer shaft 120 relative to the inner shaft 140 (exemplary embodiment not shown).

FIG. 7C illustrates the grabbing element 190 positioned in a second state, wherein the proximal surface 194 of the grabbing element 190 is distally spaced from the outer shaft distal lip 126. According to some embodiments, the second state illustrated in FIG. 7C is achieved by pushing the inner shaft 140 along with the grabbing element 190 in the distal direction 92 relative to the outer shaft 120. According to some embodiments, the second state illustrated in FIG. 7C is achieved by pulling the outer shaft 120 in a proximal direction 94 relative to the grabbing element 190.

According to some embodiments, such as the embodiments illustrated in FIGS. 7A-C, the outer shaft lumen 132 is provided with uniform diameter along the length of the outer shaft 120, or at least along the length of the outer shaft distal portion 124. According to some embodiments, the outer shaft 120 further comprises an outer shaft distal conical portion 136.

Figure 8A:
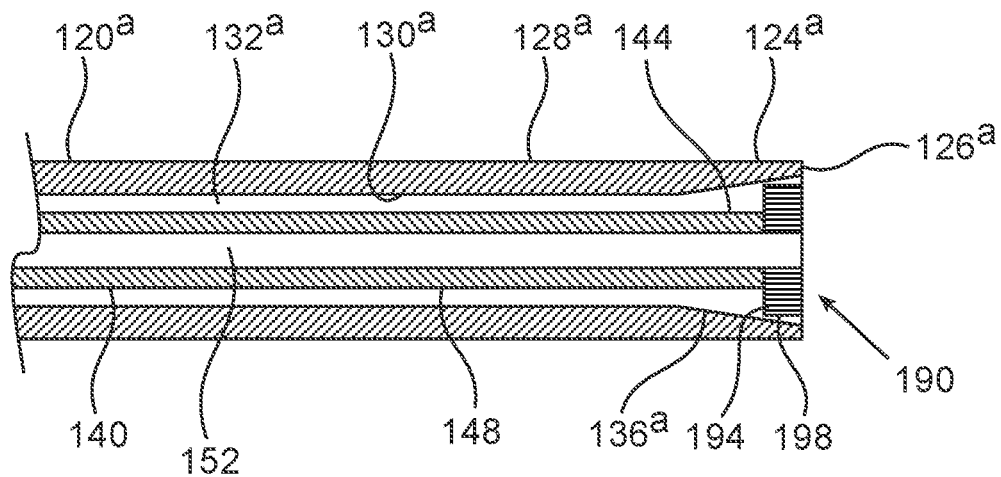
FIG. 8A constitutes a cross-sectional side view of the distal region of a non-penetrating tissue separator devoid of a cone head, in a first state, according to some embodiments.
Figure 8B:
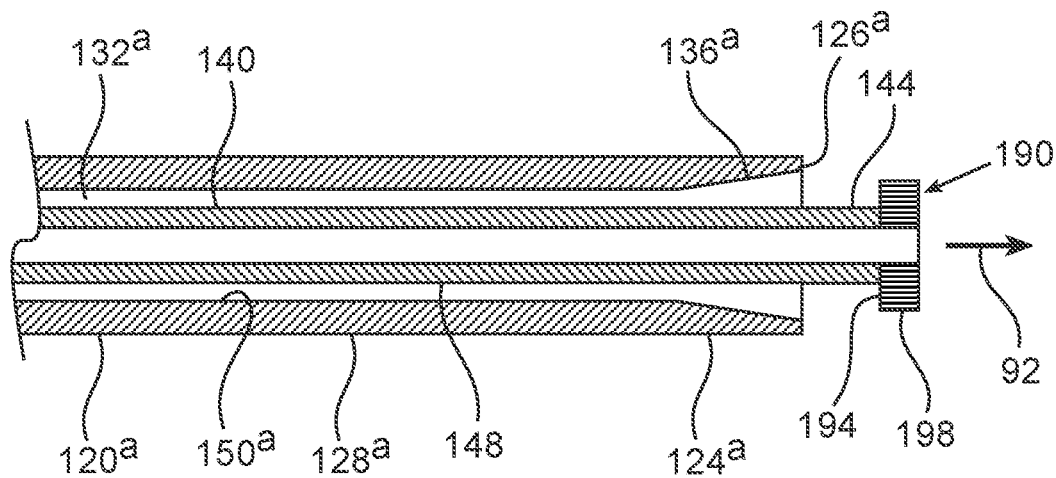
FIG. 8B constitutes a cross-sectional side view of the distal region of the non-penetrating tissue separator of FIG. 8A, in a second state.

FIGS. 8A and 8B constitute cross-sectional side views in a first state and a second state, respectively, of the non-penetrating tissue separator 100 equipped with an outer shaft 120$^a$, according to some embodiments. The outer shaft 120$^a$ is similar to the outer shaft 100 illustrated in FIGS. 7B-7C, except that its outer shaft lumen 132$^a$ further comprises an outer shaft distal conical portion 136$^a$, tapering radially inwards from the outer shaft distal lip 126$^a$ proximally up to a border from which the rest of the outer shaft lumen 132$^a$ can be provided with a uniform diameter, which is larger than the outer diameter of the inner shaft 140.

According to some embodiments, the outer diameter of the grabbing element 190 is smaller than the diameter of the distal end of the outer shaft distal conical portion 136$^a$, such that the grabbing element 190 can be inserted into a distal portion of the outer shaft distal conical portion 136$^a$. FIG. 8A illustrates the grabbing element 190 positioned in a first state, such that the distal surface 196 of the grabbing element 190 is proximal to or flush with the outer shaft distal lip 126$^a$.

According to some embodiments, the outer shaft distal conical portion 136$^a$ serves as an inner shaft retraction limiting mechanism, such that at least a proximal portion thereof is provided with a tapering diameter smaller than the outer diameter of the grabbing element 190. Thus, the outer shaft distal conical portion 136$^a$ is configured to accommodate the grabbing element 190 therein in the first position, while preventing further proximal retraction of the grabbing element 190 when it is engaged with the inner surface of the outer shaft distal conical portion 136$^a$.

FIG. 8B illustrates the grabbing element 190 positioned in a second state, wherein the proximal surface 194 of the grabbing element 190 is distally spaced from the outer shaft distal lip 126$^a$. According to some embodiments, the second state illustrated in FIG. 8B is achieved by pushing the inner shaft 140 along with the grabbing element 190 in the distal direction 92 relative to the outer shaft 120$^a$. According to some embodiments, the second state illustrated in FIG. 8B is achieved by pulling the outer shaft 120$^a$ in a proximal direction 94 relative to the grabbing element 190.

Figure 9A:
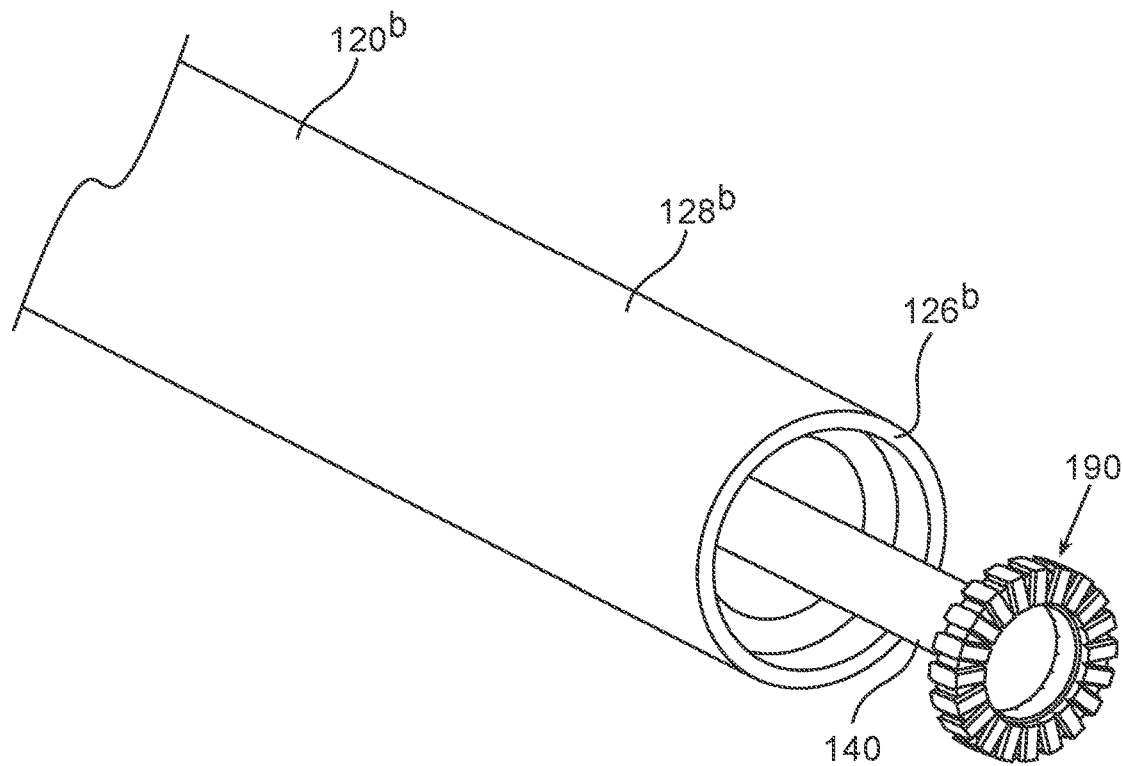
FIG. 9A constitutes a zoomed-in view in perspective of the distal region of the non-penetrating tissue separator devoid of a cone head, according to some embodiments.
Figure 9B:
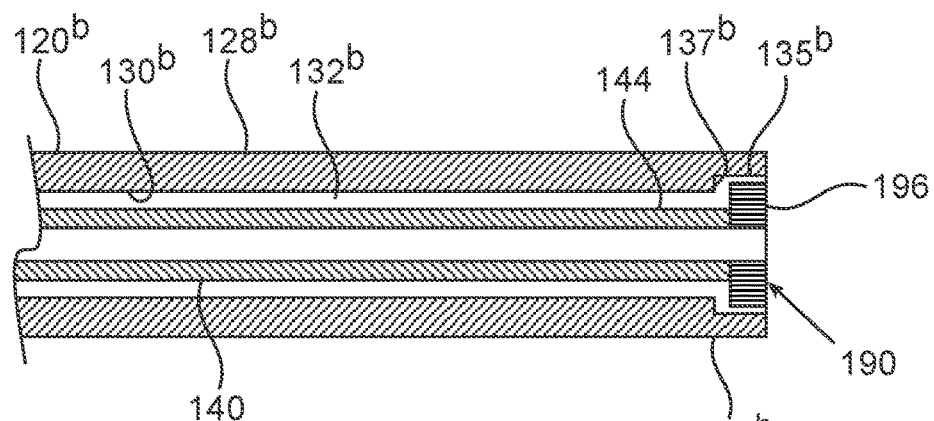
FIG. 9B constitutes a cross-sectional side view of the distal region of the non-penetrating tissue separator of FIG. 9A, in a first state.
Figure 9C:
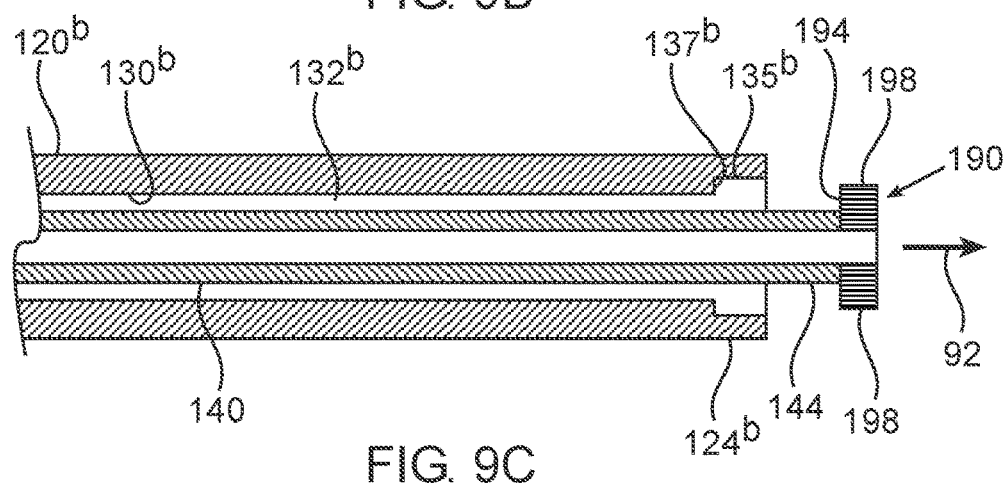
FIG. 9C constitutes a cross-sectional side view of the distal region of the non-penetrating tissue separator of FIG. 9A, in a second state.

FIG. 9A constitutes a view in perspective of a non-penetrating tissue separator 100 equipped with an outer shaft $120^b$, according to some embodiments. FIGS. 9B and 9C constitute cross-sectional side views in a first state and a second state, respectively, of the non-penetrating tissue separator 100 of FIG. 9A. The outer shaft $120^b$ is similar to the outer shaft 100 illustrated in FIGS. 7B-7C, except that its outer shaft lumen $132^b$ further comprises an outer shaft distal socket $135^b$, extending between the outer shaft distal lip $126^b$ and the outer shaft distal socket shoulder $137^b$, provided with a uniform outer diameter with is larger than the outer diameter of the rest of the outer shaft lumen $132^b$ extending proximally from the outer shaft distal socket shoulder $137^b$.

FIG. 9B illustrates the grabbing element 190 positioned in a first state, such that the distal surface 196 of the grabbing element 190 is proximal to or flush with the outer shaft distal lip $126^b$. The outer diameter of the grabbing element 190 is smaller than the diameter of the inner diameter of the outer shaft distal socket $135^b$, and larger than the inner diameter of the rest of the outer shaft lumen $132^b$.

According to some embodiments, the axial length of the outer shaft distal socket $135^b$, defined between the outer shaft distal lip $126^b$ and the outer shaft distal socket shoulder $137^b$, is equal to or larger than the axial length of the grabbing element 190, defined between the grabbing element distal surface 196 the grabbing element proximal surface 194, configured to accommodate the grabbing element 190 therein in the first state.

According to some embodiments, the outer shaft distal socket shoulder $137^b$ serves as an inner shaft retraction limiting mechanism, such that when the grabbing element proximal surface 194 abuts or is engaged with the outer shaft distal socket shoulder $137^b$, further proximal retraction of the grabbing element 190 is prevented.

FIG. 9C illustrates the grabbing element 190 positioned in a second state, wherein the proximal surface 194 of the grabbing element 190 is distally spaced from the outer shaft distal lip $126^b$. According to some embodiments, the second state illustrated in FIG. 9C is achieved by pushing the inner shaft 140 along with the grabbing element 190 in the distal direction 92 relative to the outer shaft $120^b$. According to some embodiments, the second state illustrated in FIG. 9C is achieved by pulling the outer shaft $120^b$ in a proximal direction 94 relative to the grabbing element 190.

Figure 10A:
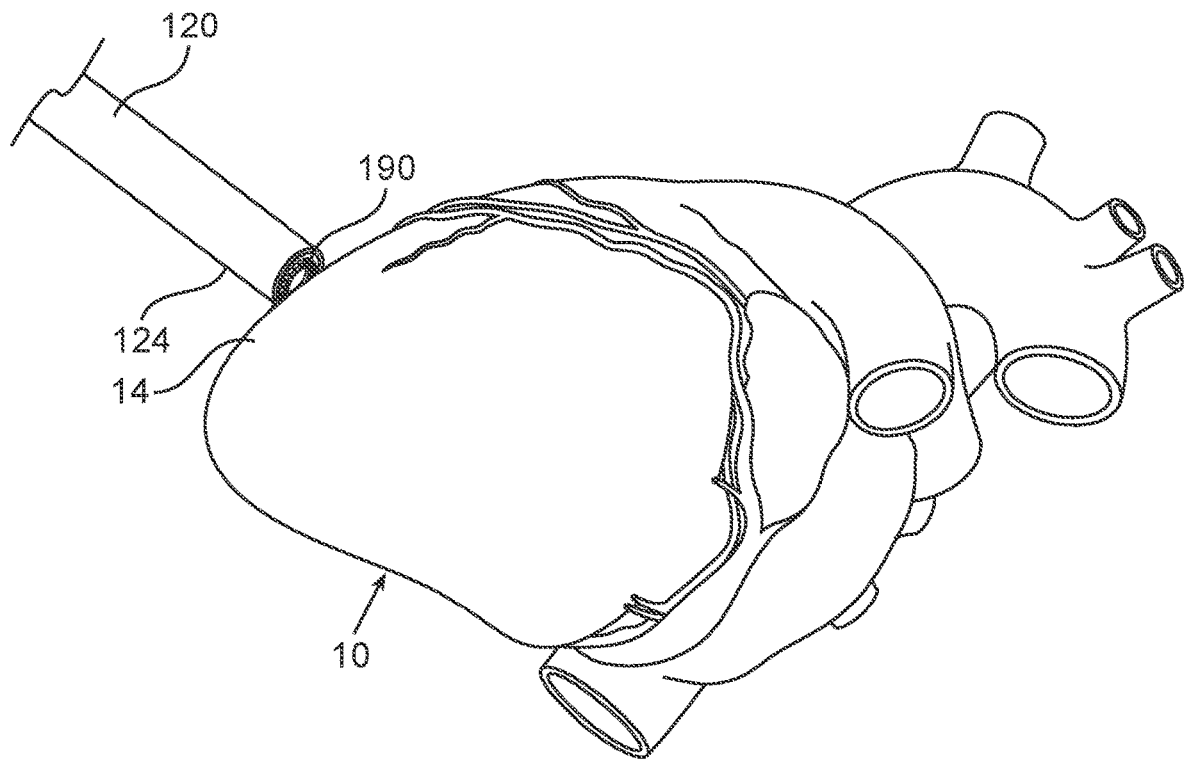
FIGS. 10A-10C illustrate different steps of a method of using the non-penetrating tissue separator, according to some embodiments.
Figure 10B:
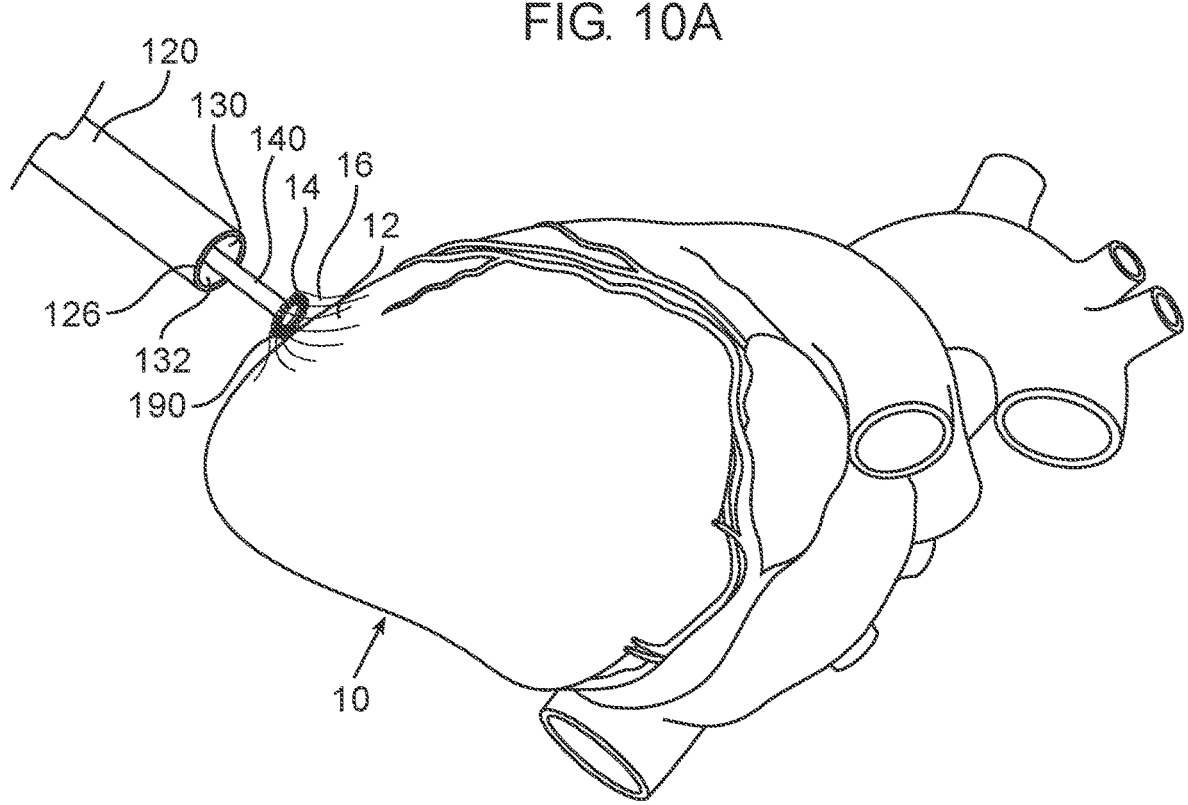
Figure 10C:
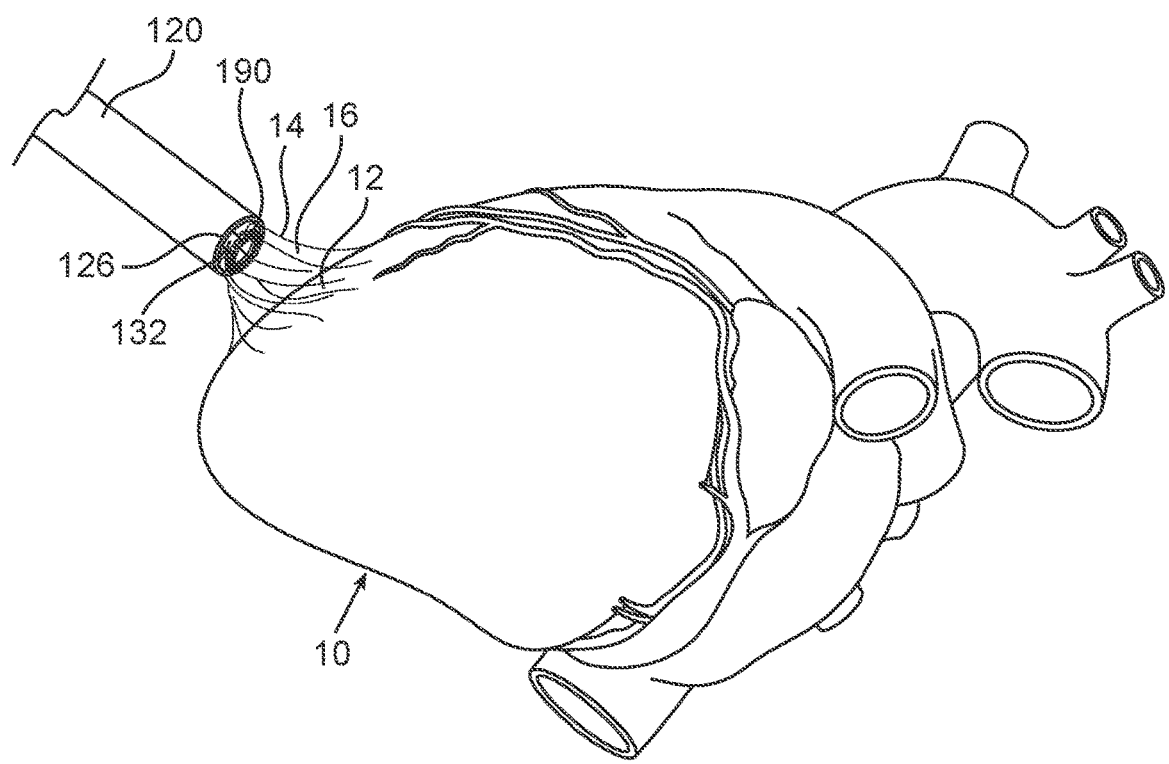

Reference is now made to FIGS. 10A-10C, depicting different steps of a method of using a non-penetrating tissue separator 100 devoid of a cone head 160, according to some embodiments. FIG. 10A shows a first step of the method, wherein the distal portion of the non-penetrating tissue separator 100, including at least a portion of the outer 120 and inner 140 shafts and the grabbing element 190, is inserted into the patient's body and advanced distally toward the heart 10 of the patient, while the non-penetrating tissue separator 100 is in a first state, that is to say while the grabbing element 190 is positioned proximal to outer shaft distal lip 126.

When the outer distal edge approximates the heart 10, such that it is at or near the pericardium 14, the operator maneuvers the non-penetrating tissue separator 100 to deploy the grabbing element 190 from a first state to a second state. According to some embodiments, the grabbing element 190 is positioned in the second state such that it is distally spaced from the outer shaft distal lip 126 (see FIG. 10B).

The grabbing element 190 is distally advanced in the second state to contact the pericardium 14. When the grabbing element 190 is at the pericardium 14, the operator maneuvers the non-penetrating tissue separator 100 to rotate the grabbing element 190 around its central axis.

The surface features 188 during the rotational movement of the grabbing element 190 causes the tissue to wrap around the grabbing element 190 as shown in FIG. 10B, without being cut or punctured thereby. Once the tissue of the pericardium 14 is wrapped around the grabbing element 190, the operator maneuvers the non-penetrating tissue separator 100 to pull the grabbing element 190 in the proximal direction to create the working pericardial space 16 (see FIG. 10C).

According to some embodiments, the grabbing element 190 is pulled in a proximal direction 94 until the pericardium 14 wrapped there along is pressed between the grabbing element 190 and at least a portion of the outer shaft 120, thereby locking the wrapped pericardial tissue 14 there between.

According to some embodiments, the outer diameter of the wrapped pericardial tissue 14 is larger than the inner diameter of the outer shaft lumen 132, such that upon retraction, the wrapped pericardial tissue 14 is pressed between the grabbing element proximal surface 194 and the outer shaft distal lip 126, as shown in FIG. 10C. According to some embodiments, the wrapped pericardial tissue 14 is pressed between the grabbing element circumferential surface 198 and the outer shaft internal surface 130.

It will be clear that the outer shaft 120 illustrated in FIGS. 10A-C can be either one of the embodiments of the outer shaft 120 from FIGS. 7A-C, the outer shaft $120^a$ from FIGS. 9A-B or the outer shaft $120^b$ from FIGS. 10A-C. According to some embodiments, the wrapped pericardial tissue 14 is pressed upon retraction between the grabbing element circumferential surface 198 and the outer shaft distal conical portion $136^a$. According to some embodiments, the wrapped pericardial tissue 14 is pressed upon retraction between the grabbing element proximal surface 194 and the outer shaft distal conical portion $136^a$.

According to some embodiments, the wrapped pericardial tissue 14 is pressed upon retraction between the grabbing element circumferential surface 198 and the outer shaft distal socket $135^b$. According to some embodiments, the wrapped pericardial tissue 14 is pressed upon retraction between the grabbing element proximal surface 194 and the outer shaft distal socket shoulder $137^b$.

According to some embodiments, the axial slidable movement between the inner shaft 140 and the outer shaft 120 is facilitated by engagement between inner threads of an outer shaft threaded portion 134 along at least a portion of the outer shaft internal surface 130, and matching outer threads of an inner shaft threaded portion 154 along at least a portion of the inner shaft external surface 148.

According to some embodiments, the axial relative movement between the inner shaft 140 and the outer shaft 120 is facilitated by engagement between the inner steering knob threading 114 along at least a portion of the steering knob internal bore 112, and matching outer threads of an inner shaft threaded portion 154 along at least a portion of the inner shaft external surface 148.

Figure 11A:
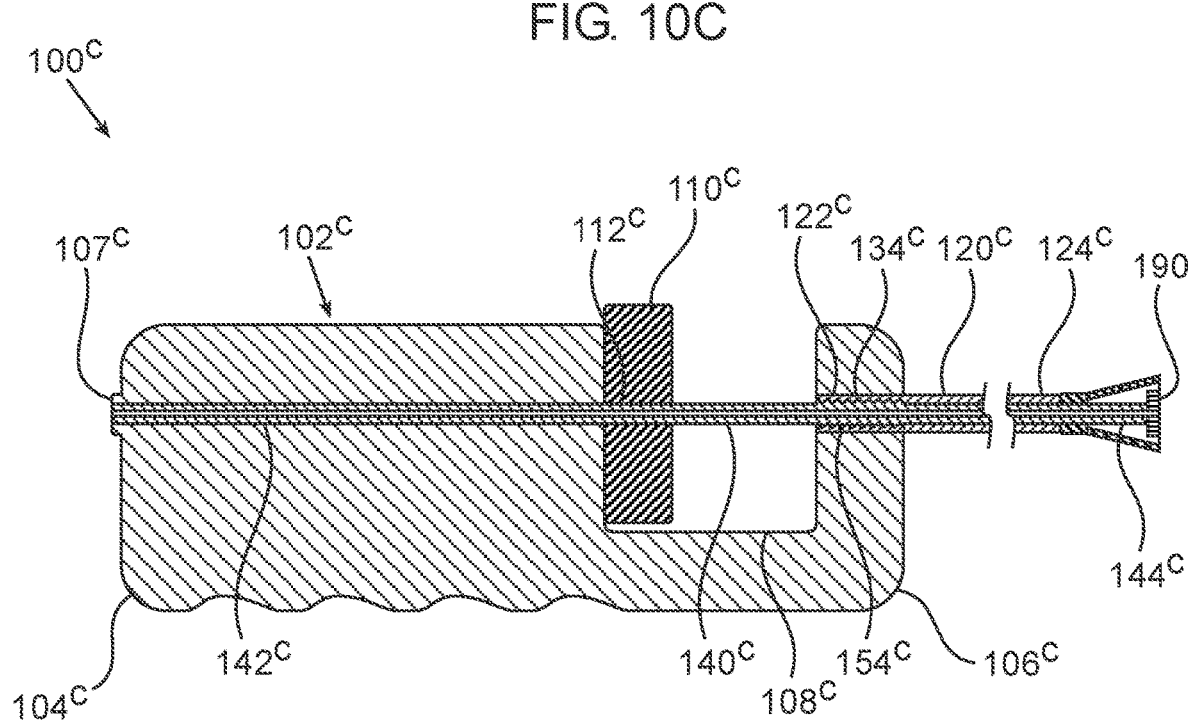
FIG. 11A constitutes a cross-sectional side view of a non-penetrating tissue separator in a first state, according to some embodiments.
Figure 11B:
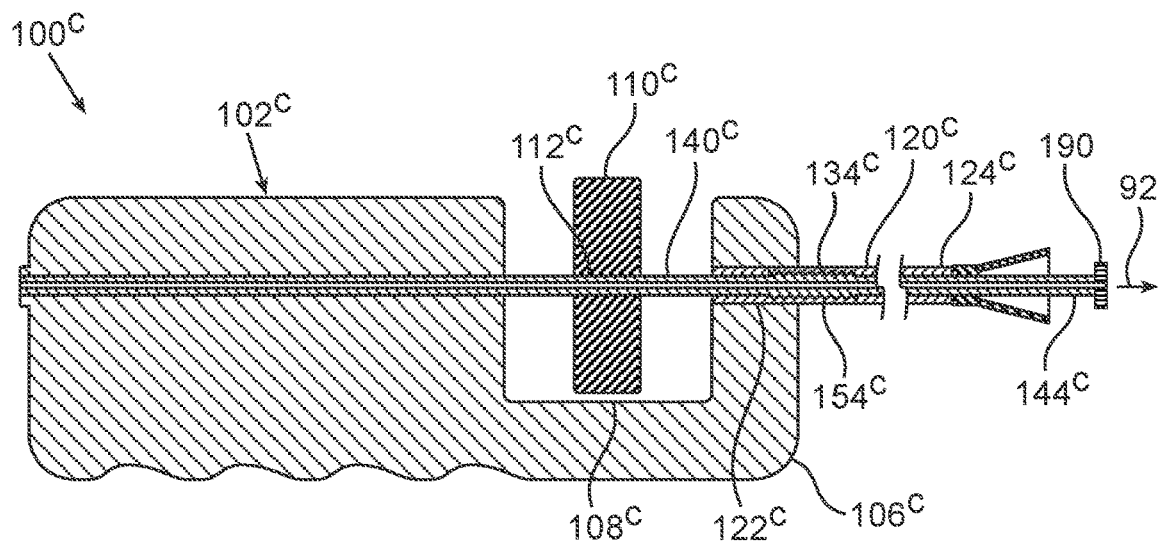
FIG. 11B constitutes a cross-sectional side view of the non-penetrating tissue separator of FIG. 11A, in a second state.
Figure 12A:
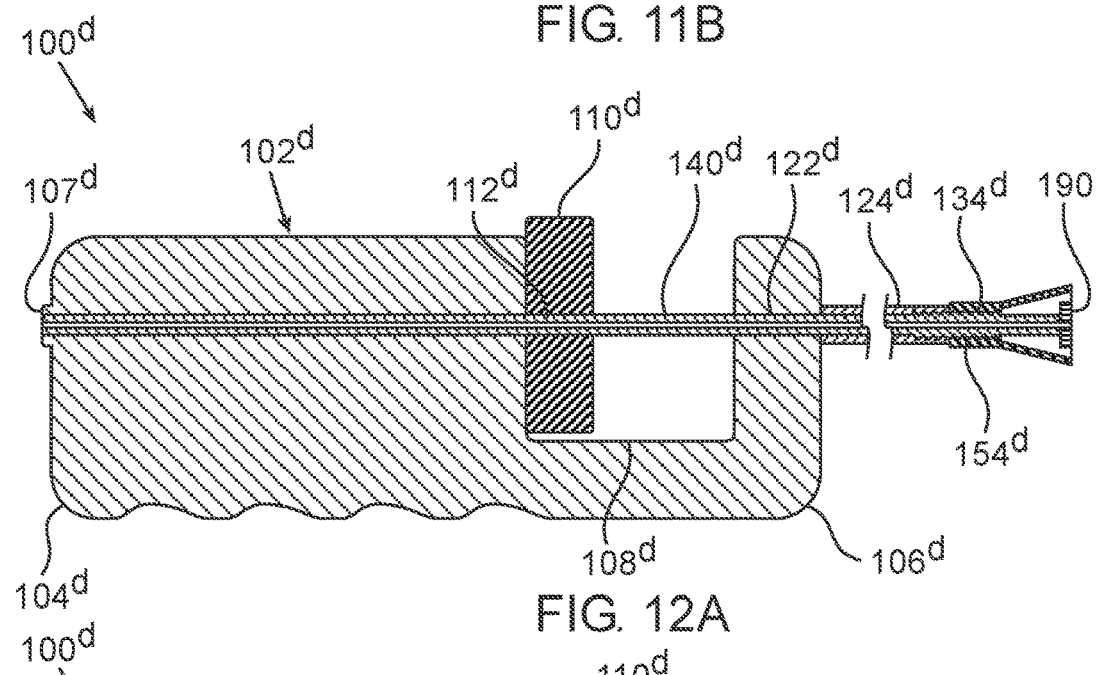
FIG. 12A constitutes a cross-sectional side view of a non-penetrating tissue separator in a first state, according to some embodiments.
Figure 12B:
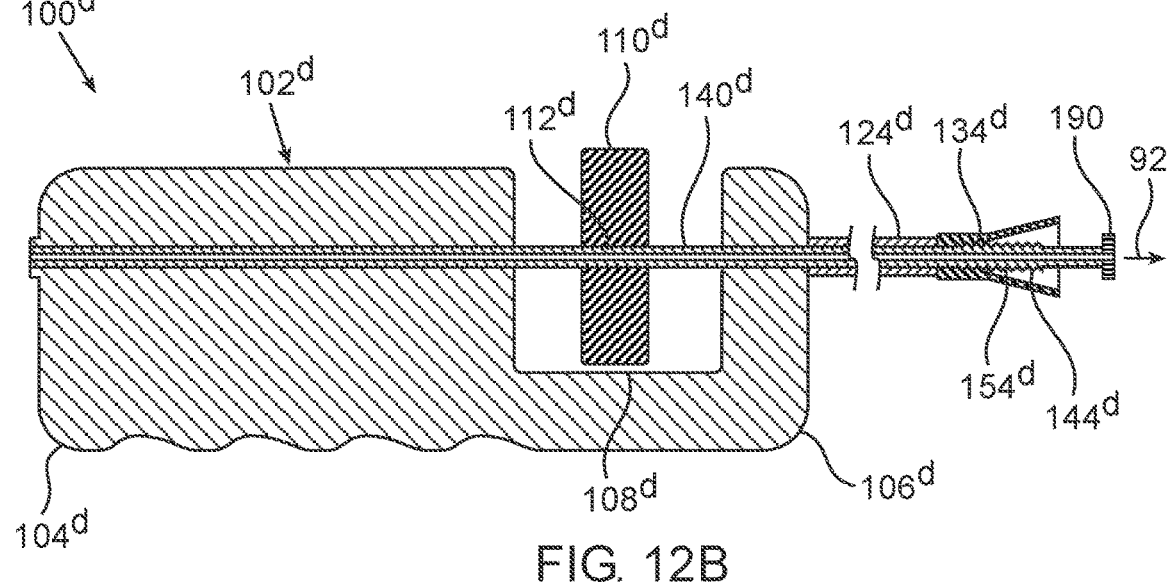
FIG. 12B constitutes a cross-sectional side view of the non-penetrating tissue separator of FIG. 12A, in a second state.
Figure 13A:
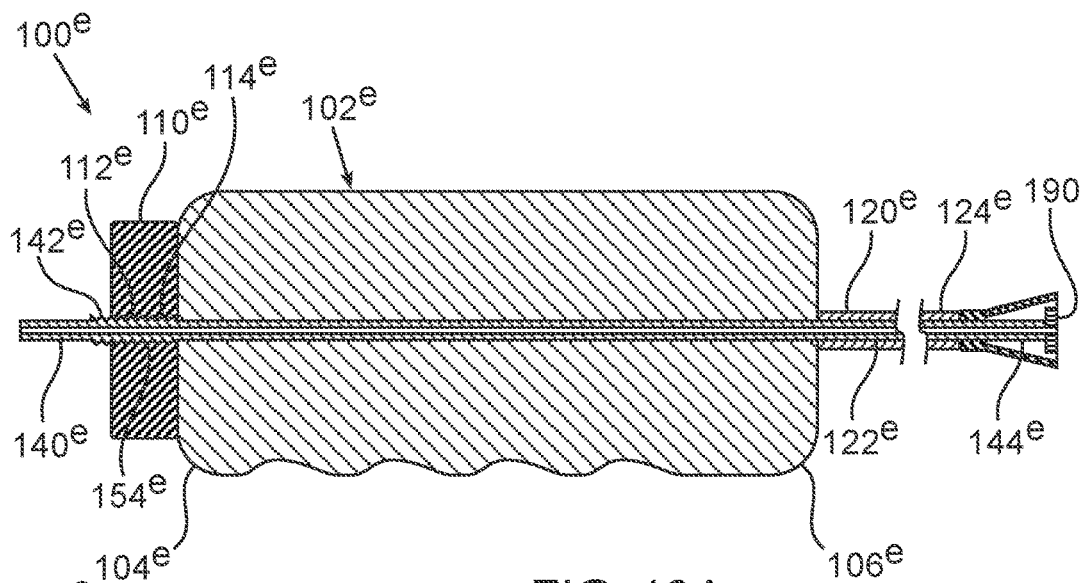
FIG. 13A constitutes a cross-sectional side view of a non-penetrating tissue separator in a first state, according to some embodiments.
Figure 13B:
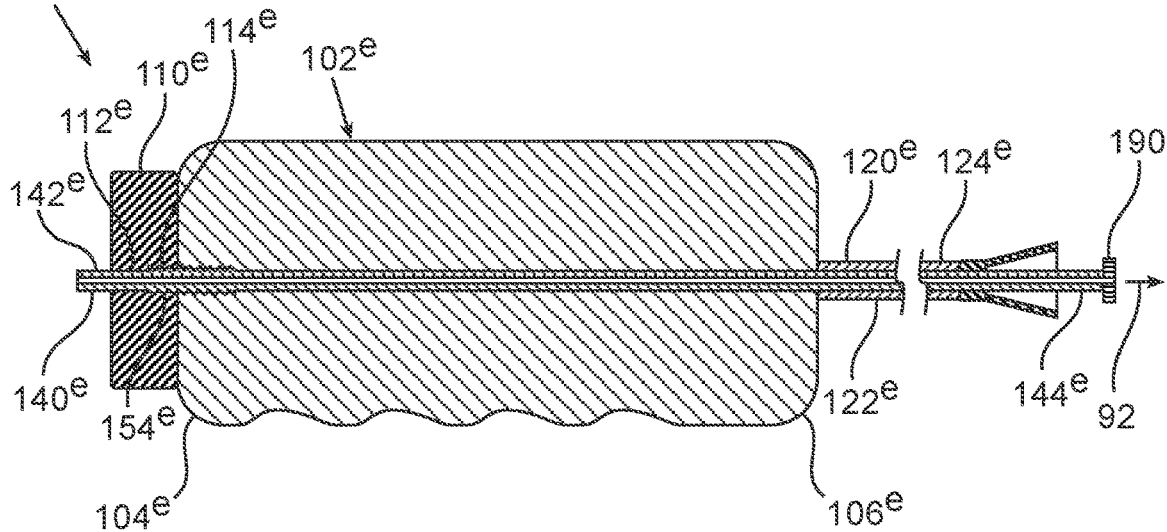
FIG. 13B constitutes a cross-sectional side view of the non-penetrating tissue separator of FIG. 13A, in a second state.
Figure 14A:
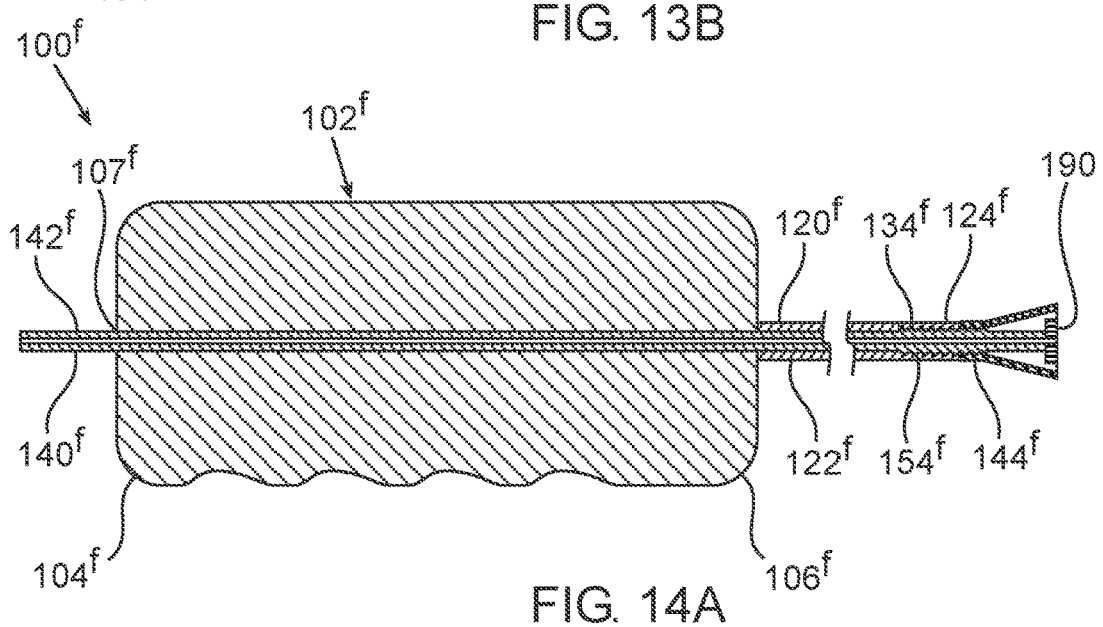
FIG. 14A constitutes a cross-sectional side view of a non-penetrating tissue separator in a first state, according to some embodiments.
Figure 14B:
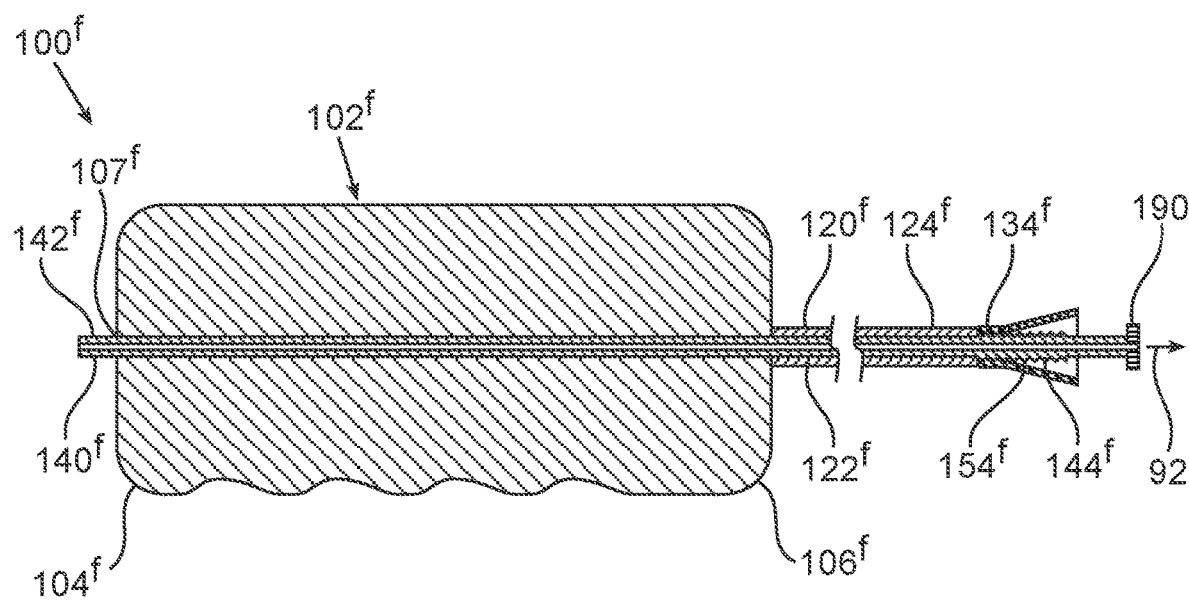
FIG. 14B constitutes a cross-sectional side view of the non-penetrating tissue separator of FIG. 14A, in a second state.

Reference is now made to FIGS. 11A-11B. FIGS. 11A and 11B constitute a cross-sectional side view of a non-penetrating tissue separator $100^c$ in a first state and a second state, respectively, according to some embodiments. FIGS. 12A and 12B constitute a cross-sectional side view of a non-penetrating tissue separator $100^d$ in a first state and a second state, respectively, according to some embodiments. FIGS. 13A and 13B constitute a cross-sectional side view of a non-penetrating tissue separator $100^e$ in a first state and a second state, respectively, according to some embodiments. FIGS. 14A and 14B constitute a cross-sectional side view of a non-penetrating tissue separator $100^f$ in a first state and a second state, respectively, according to some embodiments.

The non-penetrating tissue separator $100^c$ is similar to the non-penetrating tissue separator 100 described in any other embodiment throughout the current specification, except that the relative axial movement between the inner shaft $140^c$ and the outer shaft $120^c$ is facilitated by threaded engagement there between.

According to some embodiments, the threaded engagement between the inner shaft $140^c$ and the outer shaft $120^c$ includes engagement between inner threads of the outer shaft threaded portion $134^c$ along at least a portion of the outer shaft proximal portion $122^c$, and matching outer threads of an inner shaft threaded portion $154^c$ along at least a portion of the inner shaft external surface $148^c$.

According to some embodiments, the outer shaft proximal portion $122^c$ comprises outer shaft threaded portion $134^c$ along at least a portion of its internal surface $130^c$, and a portion of the inner shaft external surface $148^c$ comprises a matching inner shaft threaded portion $154^c$, such that the inner shaft $140^c$ is threadedly engaged with the outer shaft $120^c$. In such embodiments, rotation of the inner shaft $140^c$ in one direction translates to an axial movement thereof in the distal direction 92 relative to the outer shaft $120^c$, thereby causing the position of the grabbing element 190 to translate distally in direction 92.

According to some embodiments, the inner shaft $140^c$ is fixedly connected to the steering knob $110^c$. According to some embodiments, the inner shaft $140^c$ is fixedly connected to the steering knob internal bore $112^c$. In such embodiments, rotation of the steering knob $110^c$ in one direction can cause the inner shaft $140^c$ to rotate therewith, and translate axially in the distal direction 92 relative to the outer shaft $120^c$, thereby causing the position of the grabbing element 190 to translate distally in direction 92.

According to some embodiments, the outer shaft $120^c$ is connected to the handle $102^c$. According to some embodiments, the outer shaft $120^c$ is fixedly attached to the handle $102^c$. According to some embodiments the outer shaft $120^c$ is immovable or stationary relative to the handle $120^c$. According to some embodiments, the outer shaft proximal portion $122^c$ is fixedly attached to the handle distal portion $106^c$, for example by gluing, welding and the like. In such embodiments, displacement of the grabbing element 190 from the first state to the second state, is facilitated by axially moving the inner shaft $140^c$ in a distal direction relative to the outer shaft 120.

According to some embodiments the outer shaft $120^c$ is axially slidable within a bore of the handle 102. According to some embodiments the outer shaft $120^c$ is axially slidable within a bore of the handle distal portion 106. In such embodiments, displacement of the grabbing element 190 from the first state to the second state, is facilitated by axially moving the outer shaft $120^c$ in a proximal direction relative to the inner shaft 140.

The non-penetrating tissue separator $100^d$ is similar to the non-penetrating tissue separator 100 described in any other embodiment throughout the current specification, except that the axial slidable movement between the inner shaft $140^d$ and the outer shaft $120^d$ is facilitated by engagement between inner threads of the outer shaft threaded portion $134^d$ along at least a portion of the outer shaft distal portion $124^d$, and matching outer threads of an inner shaft threaded portion $154^d$ along at least a portion of the inner shaft distal portion $144^d$.

According to some embodiments, the outer shaft distal portion $124^d$ comprises outer shaft threaded portion $134^d$ along at least a portion of its internal surface $130^d$, and the inner shaft distal portion $144^d$ comprises a matching inner shaft threaded portion $154^d$ along at least a portion of its external surface $148^d$, such that the inner shaft $140^d$ is threadedly engaged with the outer shaft $120^d$. In such embodiments, rotation of the inner shaft $140^d$ in one direction translates to an axial movement thereof in the distal direction 92 relative to the outer shaft $120^c$, thereby causing the position of the grabbing element 190 to translate distally in direction 92.

According to some embodiments, the inner shaft $140^d$ is fixedly connected to the steering knob $110^d$. According to some embodiments, the inner shaft $140^d$ is fixedly connected to the steering knob internal bore $112^d$. In such embodiments, rotation of the steering knob $110^d$ in one direction can cause the inner shaft $140^d$ to rotate therewith, and translate axially in the distal direction 92 relative to the outer shaft $120^d$, thereby causing the position of the grabbing element 190 to translate distally in direction 92.

According to some embodiments, the outer shaft $120^d$ is connected to the handle $102^d$. According to some embodiments, the outer shaft $120^d$ is fixedly attached to the handle $102^d$. According to some embodiments the outer shaft $120^d$ is immovable or stationary relative to the handle $120^d$. According to some embodiments, the outer shaft proximal portion $122^d$ is fixedly attached to the handle distal portion $106^d$, for example by gluing, welding and the like. In such embodiments, displacement of the grabbing element 190 from the first state to the second state, is facilitated by axially moving the inner shaft $140^d$ in a distal direction relative to the outer shaft $120^d$.

According to some embodiments the outer shaft $120^d$ is axially slidable within a bore of the handle $102^d$. According to some embodiments the outer shaft $120^d$ is axially slidable within a bore of the handle distal portion $106^d$. In such embodiments, displacement of the grabbing element 190 from the first state to the second state, is facilitated by axially moving the outer shaft $120^d$ in a proximal direction relative to the inner shaft $140^d$.

The non-penetrating tissue separator $100^e$ is similar to the non-penetrating tissue separator 100 described in any other embodiment throughout the current specification, except that the handle $102^e$ is devoid of a first handle niche 108, and the axial slidable movement between the inner shaft $140^e$ and the outer shaft $120^e$ is facilitated by engagement between inner threads of steering knob threading 114e along at least a portion of the steering knob internal bore $112^e$, and matching outer threads of an inner shaft threaded portion $154^e$ along at least a portion of the inner shaft proximal portion $142^e$.

According to some embodiments, the steering knob $110^e$ is disposed at or proximal to the handle proximal portion $102^e$. According to some embodiments, the steering knob $110^e$ comprises the steering knob internal bore $112^e$, dimensioned to accept the inner shaft $140^e$ extending there through. According to some embodiments, the steering knob internal bore $112^e$ comprises the steering knob threading 114e, and a portion of external surface $148^e$ of the inner shaft proximal portion $142^e$ comprises a matching inner shaft threaded portion $154^e$, such that the inner shaft $140^e$ is threadedly engaged with the steering knob $110^e$. In such embodiments, rotation of the steering knob $110^e$ in one direction can cause the inner shaft $140^e$ to translate axially in the distal direction 92 relative to the handle 102$^e$, thereby causing the position of the grabbing element 190 to translate distally in direction 92.

According to some embodiments, the outer shaft 120$^e$ is connected to the handle 102$^e$. According to some embodiments, the outer shaft 120$^e$ is fixedly attached to the handle 102$^e$. According to some embodiments the outer shaft 120$^e$ is immovable or stationary relative to the handle 120$^e$. According to some embodiments, the outer shaft proximal portion 122$^e$ is fixedly attached to the handle distal portion 106$^e$, for example by gluing, welding and the like. In such embodiments, displacement of the grabbing element 190 from the first state to the second state, is facilitated by axially moving the inner shaft 140$^e$ in a distal direction relative to the outer shaft 120$^e$.

According to some embodiments the outer shaft 120$^e$ is axially slidable within a bore of the handle 102$^e$. According to some embodiments the outer shaft 120$^e$ is axially slidable within a bore of the handle distal portion 106$^e$. In such embodiments, displacement of the grabbing element 190 from the first state to the second state, is facilitated by axially moving the outer shaft 120$^e$ in a proximal direction relative to the inner shaft 140$^e$.

The non-penetrating tissue separator 100$^f$ is similar to the non-penetrating tissue separator 100 described in any other embodiment throughout the current specification, except that the handle 102$^f$ is devoid of a steering knob 110, and the relative axial movement between the inner shaft 140$^f$ and the outer shaft 120$^f$ is facilitated by threaded engagement between the inner shaft 140$^f$ and the handle 102$^f$.

According to some embodiments, the threaded engagement between the inner shaft 140$^f$ and the handle 102$^f$ includes engagement between inner threads of the outer shaft threaded portion 134$^f$ along at least a portion of the outer shaft distal portion 124$^f$, and matching outer threads of an inner shaft threaded portion 154$^f$ along at least a portion of the inner shaft distal portion 144$^f$.

According to some embodiments, the outer shaft distal portion 124$^f$ comprises outer shaft threaded portion 134$^f$ along at least a portion of its internal surface 130$^f$, and the inner shaft distal portion 144$^f$ comprises a matching inner shaft threaded portion 154$^f$ along at least a portion of its external surface 148$^f$, such that the inner shaft 140$^f$ is threadedly engaged with the outer shaft 120$^f$. In such embodiments, rotation of the inner shaft 140$^d$ in one direction translates to an axial movement thereof in the distal direction 92 relative to the outer shaft 120$^f$, thereby causing the position of the grabbing element 190 to translate distally in direction 92.

According to some embodiments, the outer shaft 120$^f$ is connected to the handle 102$^f$. According to some embodiments, the outer shaft 120$^f$ is fixedly attached to the handle 102$^f$. According to some embodiments the outer shaft 120$^f$ is immovable or stationary relative to the handle 120$^f$. According to some embodiments, the outer shaft proximal portion 122$^f$ is fixedly attached to the handle distal portion 106$^f$, for example by gluing, welding and the like. In such embodiments, displacement of the grabbing element 190 from the first state to the second state, is facilitated by axially moving the inner shaft 140$^f$ in a distal direction relative to the outer shaft 120$^f$.

According to some embodiments the outer shaft 120$^f$ is axially slidable within a bore of the handle 102$^f$. According to some embodiments the outer shaft 120$^f$ is axially slidable within a bore of the handle distal portion 106$^f$. In such embodiments, displacement of the grabbing element 190 from the first state to the second state, is facilitated by axially moving the outer shaft 120$^f$ in a proximal direction relative to the inner shaft 140$^f$.

It will be clear that the axial movement between the inner shaft 140 and the outer shaft 120 throughout the specification can be bi-directional, i.e. in either a distal or a proximal direction relative to each other. Likewise, it will be clear throughout the specification that whenever a first component can be rotated in a first direction to facilitate distal movement of the same first component or a different second component, rotation of the first component is also possible in the opposite direction to facilitate proximal movement of the same first component or a different second component.

It will be clear that any combination of the embodiments of different components of the non-penetrating tissue separator 100 can be available, such as but not limited to, a separator 100 with or without a steering knob 110, with or without a first handle niche 108, with or without a cone head 160, with or without threaded engagement between the inner shaft 120 and the outer shaft 140, with or without threaded engagement between the inner shaft 120 and the steering knob 110, and so on.

While some of the embodiments exemplify threaded engagement between the inner shaft 120 and the outer shaft 140 along either the outer shaft proximal portion 122 or the outer shaft distal portion 124, it will be clear that such a threaded engagement can be positioned along any region of the outer shaft 140, and can extend along the entire length of the outer shaft 140.

According to some embodiments, the inner shaft 140 is devoid of an inner shaft threaded portion 154, such that relative axial movement between the inner shaft 140 and the outer shaft 120 is facilitated by pushing, for example in a telescoping manner, the outer shaft 120 in a distal direction 92 relative to the outer shaft 120, or alternatively by pulling the outer shaft 120 in a proximal direction 94 relative to the inner shaft 140. According to some embodiments, the inner shaft 140 is further fixedly connected to the steering knob 110, for example to the steering knob internal bore 112. In such embodiments, pushing or pulling the inner shaft 140 in an axial direction can be facilitated by pushing or pulling the steering knob 110.

Figure 15:
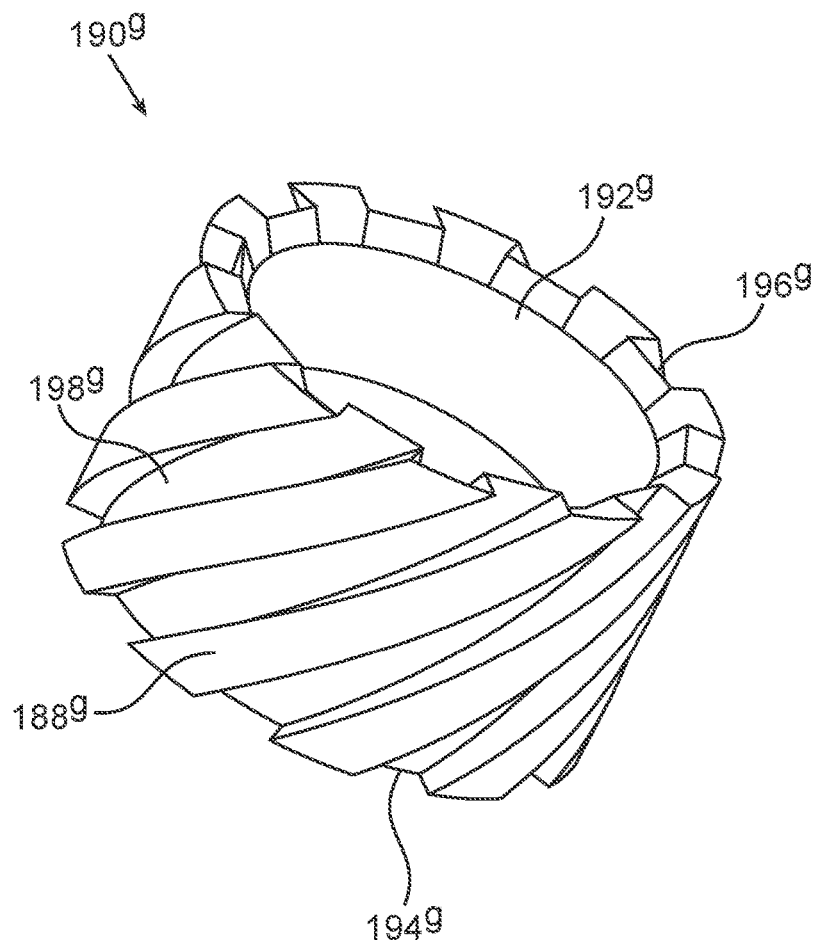
FIG. 15 constitutes a view in perspective of a grabbing element, According to some embodiments.
Figure 16A:
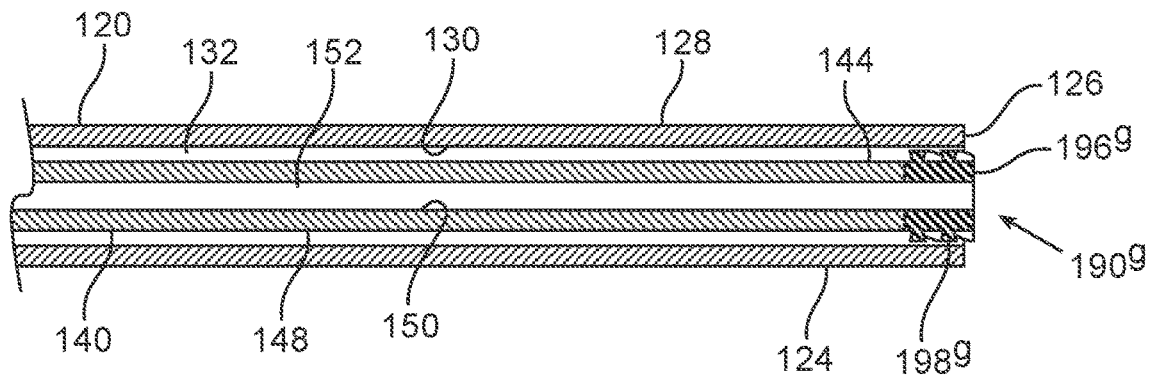
FIG. 16A constitutes a cross-sectional side view of the distal region of a non-penetrating tissue separator in a first state, according to some embodiments.
Figure 16B:
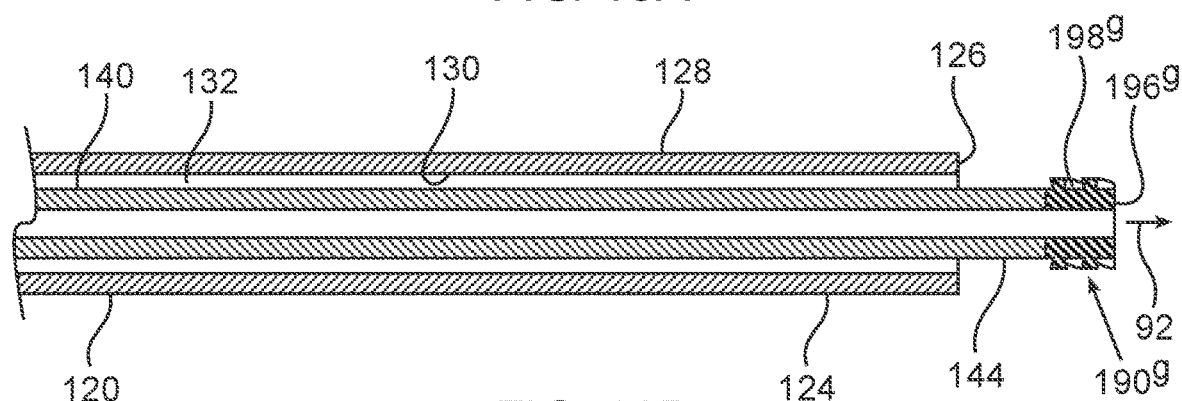
FIG. 16B constitutes a cross-sectional side view of the distal region of the non-penetrating tissue separator of FIG. 16A, in a second state.
Figure 17A:
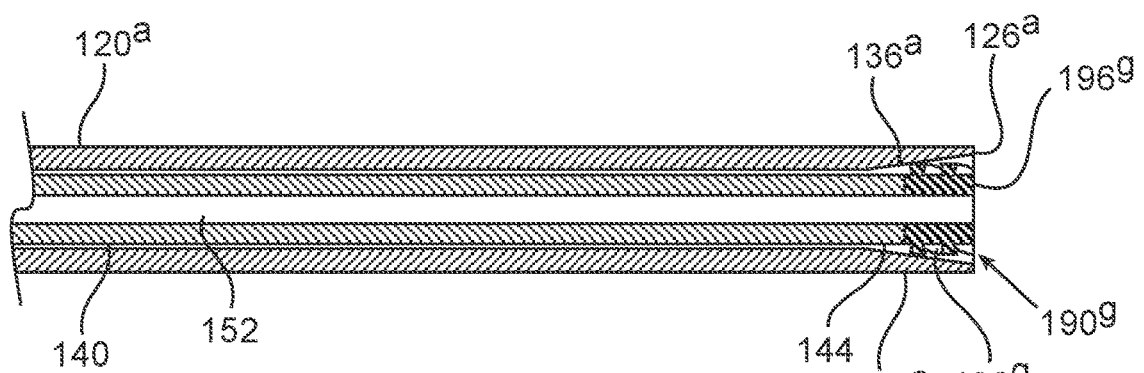
FIG. 17A constitutes a cross-sectional side view of the distal region of a non-penetrating tissue separator in a first state, according to some embodiments.
Figure 17B:
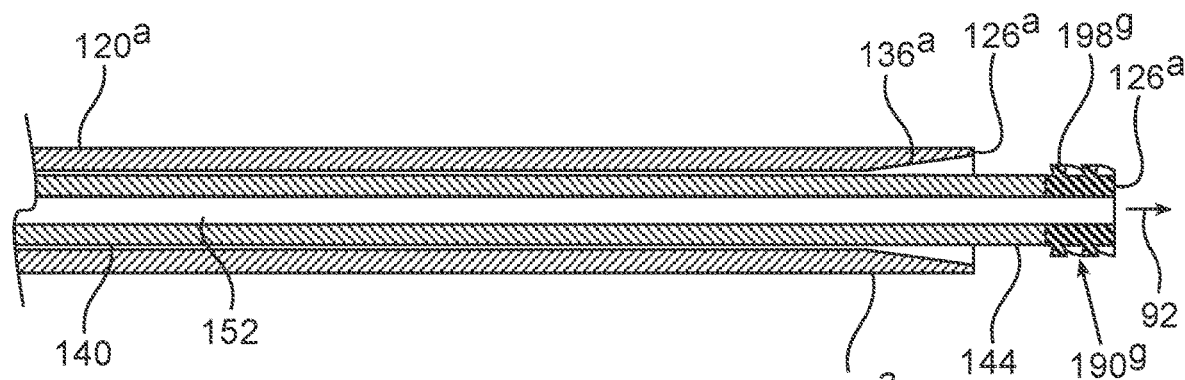
FIG. 17B constitutes a cross-sectional side view of the distal region of the non-penetrating tissue separator of FIG. 17A, in a second state.
Figure 18A:
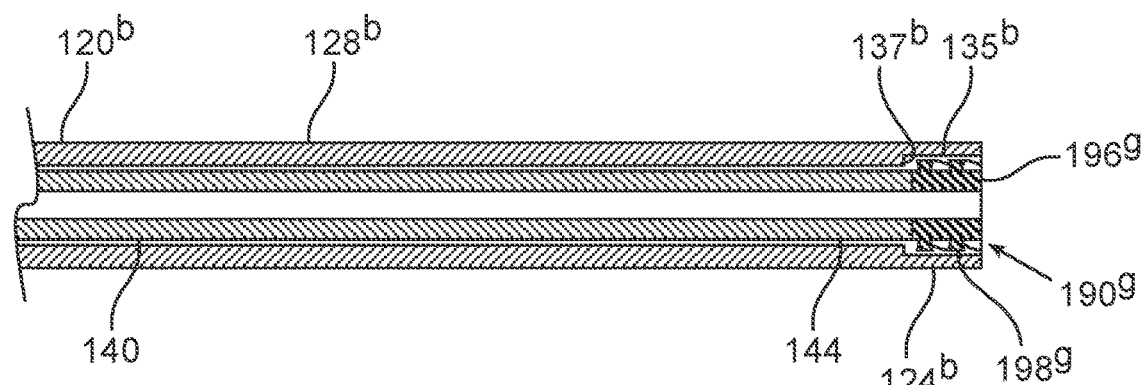
FIG. 18A constitutes a cross-sectional side view of the distal region of a non-penetrating tissue separator in a first state, according to some embodiments.
Figure 18B:
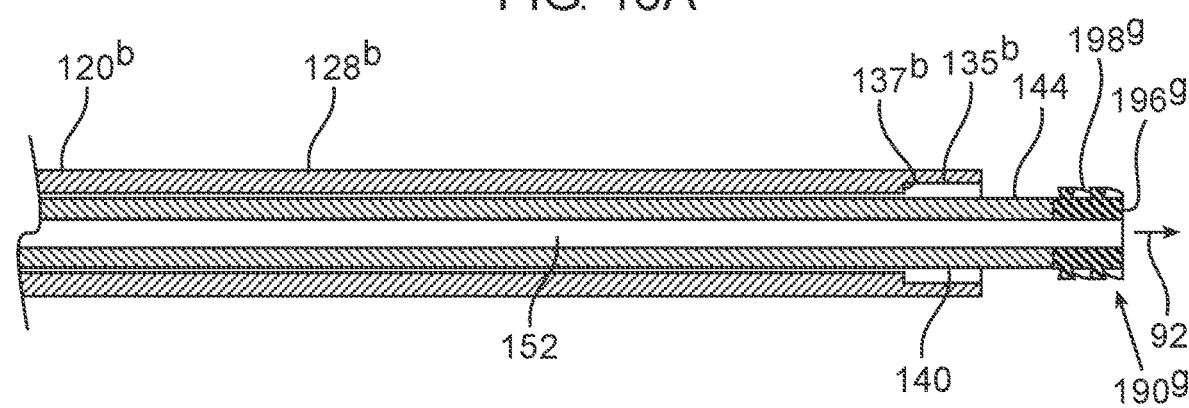
FIG. 18B constitutes a cross-sectional side view of the distal region of the non-penetrating tissue separator of FIG. 18A, in a second state.

Reference is now made to FIGS. 15-18B. FIG. 15 constitutes a view in perspective of a grabbing element 190$^g$, according to some embodiments. FIGS. 16A and 16B constitute a cross-sectional side views in a first state and a second state, respectively, of the non-penetrating tissue separator 100 equipped with an outer shaft 120 and a grabbing element 190$^g$, according to some embodiments. FIGS. 17A and 17B constitute a cross-sectional side views in a first state and a second state, respectively, of the non-penetrating tissue separator 100 equipped with an outer shaft 120$^a$ and a grabbing element 190$^g$, according to some embodiments. FIGS. 18A and 18B constitute a cross-sectional side views in a first state and a second state, respectively, of the non-penetrating tissue separator 100 equipped with an outer shaft 120$^b$ and a grabbing element 190$^g$, according to some embodiments.

The grabbing element 190$^g$ differs from the embodiments of grabbing elements 190$^a$-190$^e$ (see FIGS. 2A-F), for example, in that it is not shaped like a disc but is rather longer in the axial direction, assuming the shape of a bolt. According to some embodiments, a disc-like shape of a grabbing element 190 refers to an axial length thereof being shorter than its outer diameter. According to some embodiments, a disc-like shape of a grabbing element 190 refers to an axial length thereof being shorter than its outer radius.

According to some embodiments, an elongated shape of a grabbing element 190 refers to an axial length thereof being equal to or longer than its outer diameter.

FIG. 15 illustrates a grabbing element 190$^g$ provided with surface features 188$^g$ in the form of radial extensions disposed along the grabbing element circumferential surface 198$^g$, protruding distally therefrom, and potentially disposed along the grabbing element distal surface 196$^g$, protruding distally therefrom. According to some embodiments, the surface features 188$^g$ are in the form of blunt teeth, each tooth disposed along an axial curved path between the grabbing element proximal surface 194$^g$ and the grabbing element distal surface 196$^g$, without encircling the grabbing element circumferential surface 198$^g$.

According to some embodiments, the surface features 188$^g$ are formed so as to create flutes there between, configured to accommodate portions of a tissue, such as the pericardium 14, when wrapped there along.

Advantageously, the elongated grabbing element 190$^g$ offers a larger grabbing element circumferential surface 198$^g$ along which the pericardium 14 can be wrapped relative to disc-shaped configurations of the grabbing element 190$^g$, thereby providing improved grip or engagement there between.

According to some embodiments, the grabbing element 190 is provided with non-uniform diameter along its length (embodiments not shown). According to some embodiments, the grabbing element 190 tapers between the grabbing element distal surface 196 and the grabbing element proximal surface 194, so as to form a frusto-conical profile.

According to some embodiments, the diameter of the grabbing element distal surface 196 is smaller than the diameter of the grabbing element proximal surface 194. According to some embodiments, the diameter of the grabbing element distal surface 196 is larger than the diameter of the grabbing element proximal surface 194.

According to some embodiments, the outer diameter of the grabbing element 190$^g$ is smaller than the diameter of the outer shaft lumen 132, such that the grabbing element 190$^g$ can be inserted into the outer shaft lumen 132. In such embodiments, the outer shaft distal lip 126 serves as the outer distal edge. FIG. 16A illustrates the grabbing element 190$^g$ positioned in a first state, such that the distal surface 196$^g$ of the grabbing element 190 is proximal to or flush with the outer shaft distal lip 126.

According to some embodiments, the grabbing element 190 and the inner shaft 140 are integrally formed, such that the grabbing element proximal surface 194 is not visible as a separate surface but is rather continuous with an inner shaft's 120 distal lip.

According to some embodiments, the grabbing element 190 constitutes a distal portion of the inner shaft 120, for example by forming a distal region along the inner shaft comprising surface features 188 along at least one of the distal lip of the inner shaft 120, which constitutes the grabbing element distal surface 196 in such embodiments, or at least a portion of the inner shaft distal portion 144, which constitutes the grabbing element circumferential surface 198 in such embodiments.

FIG. 16B illustrates the grabbing element 190$^g$ positioned in a second state, wherein the proximal surface 194$^g$ of the grabbing element 190$^g$ is distally spaced from the outer shaft distal lip 126. According to some embodiments, the second state illustrated in FIG. 16B is achieved by pushing the inner shaft 140 along with the grabbing element 190$^g$ in the distal direction 92 relative to the outer shaft 120. According to some embodiments, the second state illustrated in FIG. 16B is achieved by pulling the outer shaft 120 in a proximal direction 94 relative to the grabbing element 190$^g$.

The outer shaft 120$^a$ illustrated in FIGS. 17A-17B is similar to the outer shaft 120$^a$ of FIGS. 8A-8B, comprising the outer shaft distal conical portion 136$^a$. FIG. 17A illustrates the grabbing element 190$^g$ positioned in a first state, such that the distal surface 196$^g$ of the grabbing element 190$^g$ is proximal to or flush with the outer shaft distal lip 126$^a$.

According to some embodiments, the outer shaft distal conical portion 136$^a$ serves as an inner shaft retraction limiting mechanism, such that at least a proximal portion thereof is provided with a tapering diameter smaller than the outer diameter of the grabbing element 190$^g$. Thus, the outer shaft distal conical portion 136$^a$ is configured to accommodate the grabbing element 190$^g$ therein in the first position, while preventing further proximal retraction of the grabbing element 190$^g$ when it is engaged with the inner surface of the outer shaft distal conical portion 136$^a$.

FIG. 17B illustrates the grabbing element 190$^g$ positioned in a second state, wherein the proximal surface 194$^g$ of the grabbing element 190$^g$ is distally spaced from the outer shaft distal lip 126$^a$. According to some embodiments, the second state illustrated in FIG. 8B is achieved by pushing the inner shaft 140 along with the grabbing element 190$^g$ in the distal direction 92 relative to the outer shaft 120$^a$. According to some embodiments, the second state illustrated in FIG. 17B is achieved by pulling the outer shaft 120$^a$ in a proximal direction 94 relative to the grabbing element 190$^g$.

The outer shaft 120$^b$ illustrated in FIGS. 18A-18B is similar to the outer shaft 120$^b$ of FIGS. 9A-9C, comprising the outer shaft distal socket 135$^b$. FIG. 18A illustrates the grabbing element 190$^g$ positioned in a first state, such that the distal surface 196$^g$ of the grabbing element 190$^g$ is proximal to or flush with the outer shaft distal lip 126$^b$. The outer diameter of the grabbing element 190$^g$ is smaller than the diameter of the inner diameter of the outer shaft distal socket 135$^b$, and larger than the inner diameter of the rest of the outer shaft lumen 132$^b$.

According to some embodiments, the axial length of the outer shaft distal socket 135$^b$, defined between the outer shaft distal lip 126$^b$ and the outer shaft distal socket shoulder 137$^b$, is equal to or larger than the axial length of the grabbing element 190$^g$, defined between the grabbing element distal surface 196$^g$ the grabbing element proximal surface 194$^g$, configured to accommodate the grabbing element 190$^g$ therein in the first state.

According to some embodiments, the outer shaft distal socket shoulder 137$^b$ serves as an inner shaft retraction limiting mechanism, such that when the grabbing element proximal surface 194$^g$ abuts or is engaged with the outer shaft distal socket shoulder 137$^b$, further proximal retraction of the grabbing element 190$^g$ is prevented.

FIG. 18B illustrates the grabbing element 190$^g$ positioned in a second state, wherein the proximal surface 194$^g$ of the grabbing element 190$^g$ is distally spaced from the outer shaft distal lip 126$^b$. According to some embodiments, the second state illustrated in FIG. 18B is achieved by pushing the inner shaft 140 along with the grabbing element 190$^g$ in the distal direction 92 relative to the outer shaft 120$^b$. According to some embodiments, the second state illustrated in FIG. 18B is achieved by pulling the outer shaft 120$^b$ in a proximal direction 94 relative to the grabbing element 190$^g$.

Figure 19A:
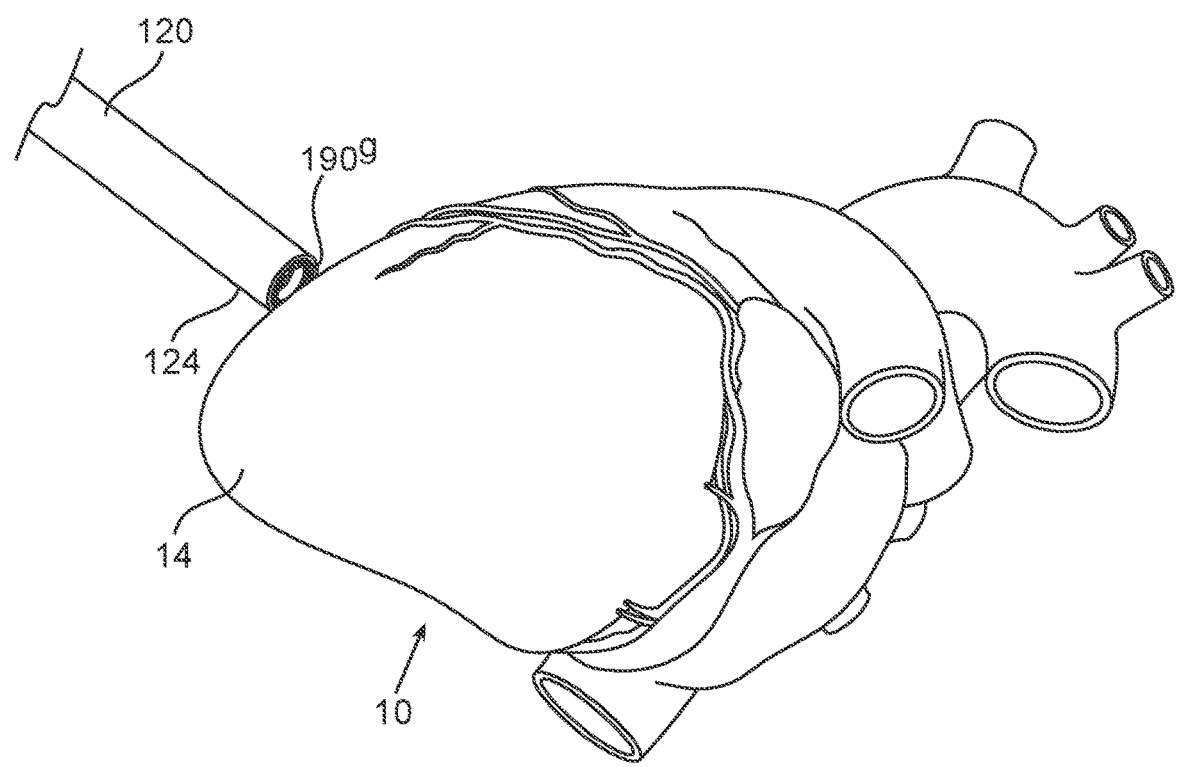
FIGS. 19A-19C illustrate different steps of a method of using the non-penetrating tissue separator, according to some embodiments.
Figure 19B:
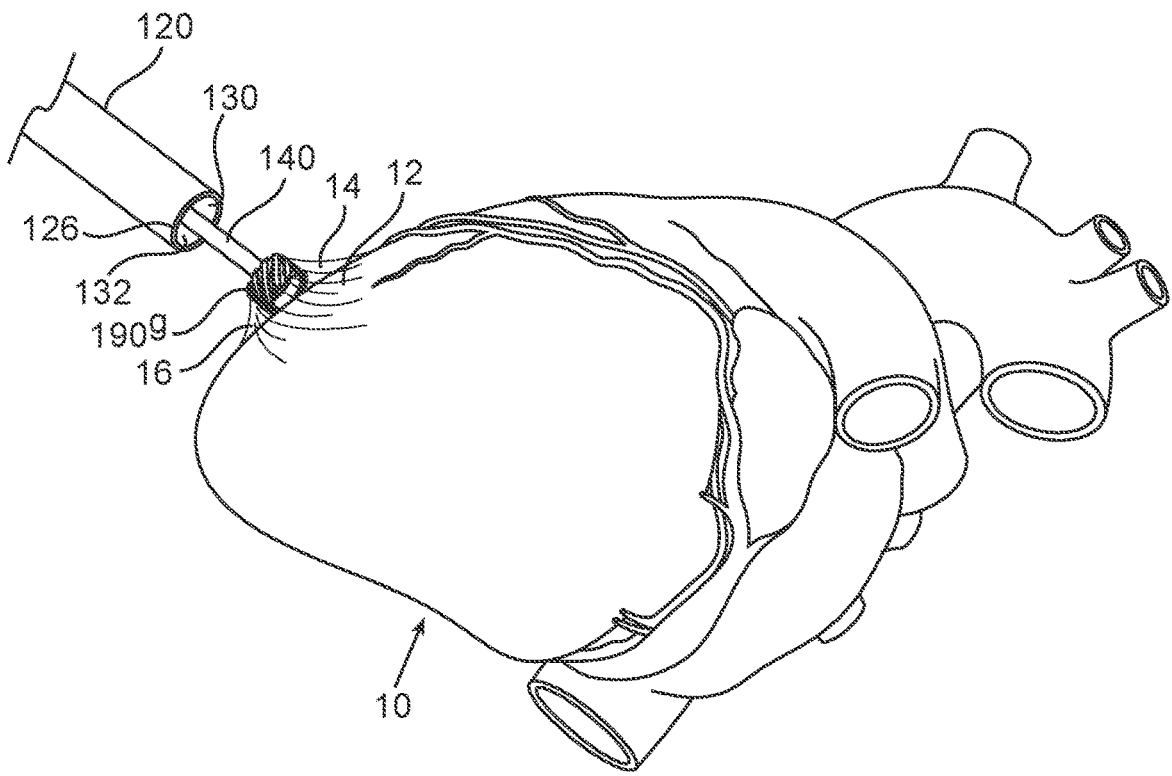
Figure 19C:
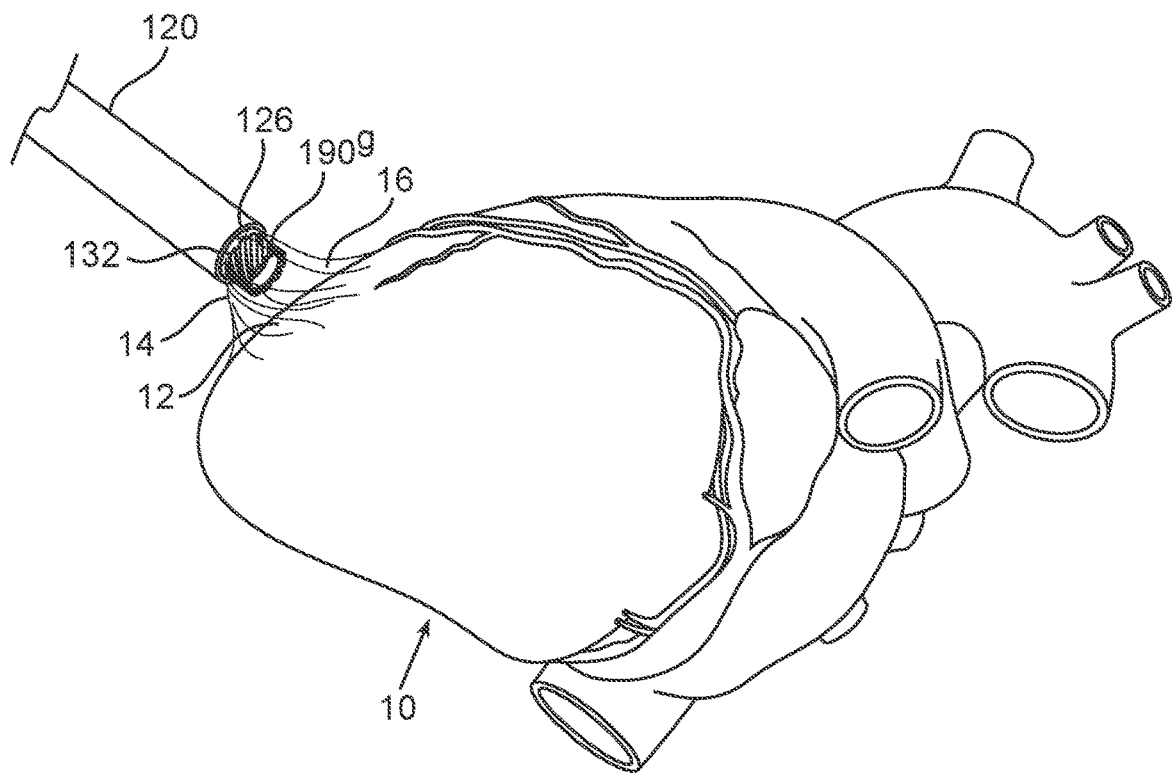

Reference is now made to FIGS. 19A-19C, depicting different steps of a method of using a non-penetrating tissue separator 100 equipped with an elongated grabbing element 190$^g$, according to some embodiments. FIG. 19A shows a first step of the method, wherein the distal portion of the non-penetrating tissue separator 100, including at least a portion of the outer 120 and inner 140 shafts and the elongated grabbing element 190$^g$, is inserted into the patient's body and advanced distally toward the heart 10 of the patient, while the non-penetrating tissue separator 100 is in a first state, that is to say while the elongated grabbing element 190$^g$ is positioned proximal to outer shaft distal lip 126.

When the outer distal edge approximates the heart 10, such that it is at or near the pericardium 14, the operator maneuvers the non-penetrating tissue separator 100 to deploy the elongated grabbing element 190$^g$ from a first state to a second state. According to some embodiments, the elongated grabbing element 190$^g$ is positioned in the second state such that it is distally spaced from the outer shaft distal lip 126 (see FIG. 19B).

The elongated grabbing element 190$^g$ is distally advanced in the second state to contact the pericardium 14. When the elongated grabbing element 190$^g$ is at the pericardium 14, the operator maneuvers the non-penetrating tissue separator 100 to rotate the elongated grabbing element 190$^g$ around its central axis.

The surface features 188$^g$, during the rotational movement of the elongated grabbing element 190$^g$, cause the tissue to wrap around the elongated grabbing element 190$^g$ as shown in FIG. 19B, without being cut or punctured thereby. Once the tissue of the pericardium 14 is wrapped around the elongated grabbing element 190$^g$, the operator maneuvers the non-penetrating tissue separator 100 to pull the elongated grabbing element 190$^g$ in the proximal direction to create the working pericardial space 16 (see FIG. 19C).

According to some embodiments, the elongated grabbing element 190$^g$ is pulled in a proximal direction 94 until the pericardium 14 wrapped there along is pressed between the elongated grabbing element 190$^g$ and at least a portion of the outer shaft 120, thereby locking the wrapped pericardial tissue 14 there between.

According to some embodiments, the outer diameter of the wrapped pericardial tissue 14 is larger than the inner diameter of the outer shaft lumen 132, such that upon retraction, the wrapped pericardial tissue 14 is pressed between the grabbing element proximal surface 194$^g$ and the outer shaft distal lip 126, as shown in FIG. 19C. According to some embodiments, the wrapped pericardial tissue 14 is pressed between the grabbing element circumferential surface 198$^g$ and the outer shaft internal surface 130.

It will be clear that the outer shaft 120 illustrated in FIGS. 19A-C can be either one of the embodiments of the outer shaft 120 from FIGS. 16A-B, the outer shaft 120$^a$ from FIGS. 17A-B or the outer shaft 120$^b$ from FIGS. 18A-B. According to some embodiments, the wrapped pericardial tissue 14 is pressed upon retraction between the grabbing element circumferential surface 198$^g$ and the outer shaft distal conical portion 136$^a$. According to some embodiments, the wrapped pericardial tissue 14 is pressed upon retraction between the grabbing element proximal surface 194$^g$ and the outer shaft distal conical portion 136$^a$.

According to some embodiments, the wrapped pericardial tissue 14 is pressed upon retraction between the grabbing element circumferential surface 198$^g$ and the outer shaft distal socket 135$^b$. According to some embodiments, the wrapped pericardial tissue 14 is pressed upon retraction between the grabbing element proximal surface 194$^g$ and the outer shaft distal socket shoulder 137$^b$.

Figure 20A:
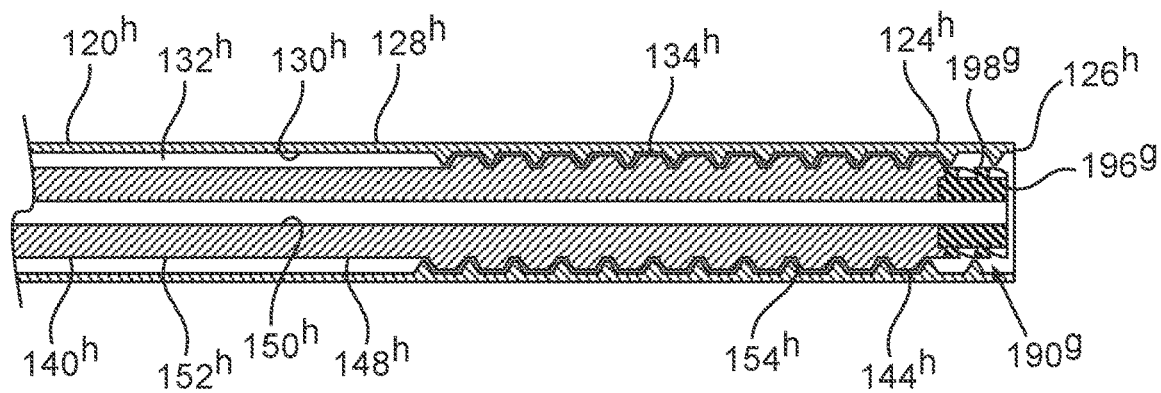
FIG. 20A constitutes a cross-sectional side view of the distal region of a non-penetrating tissue separator in a first state, according to some embodiments.
Figure 20B:
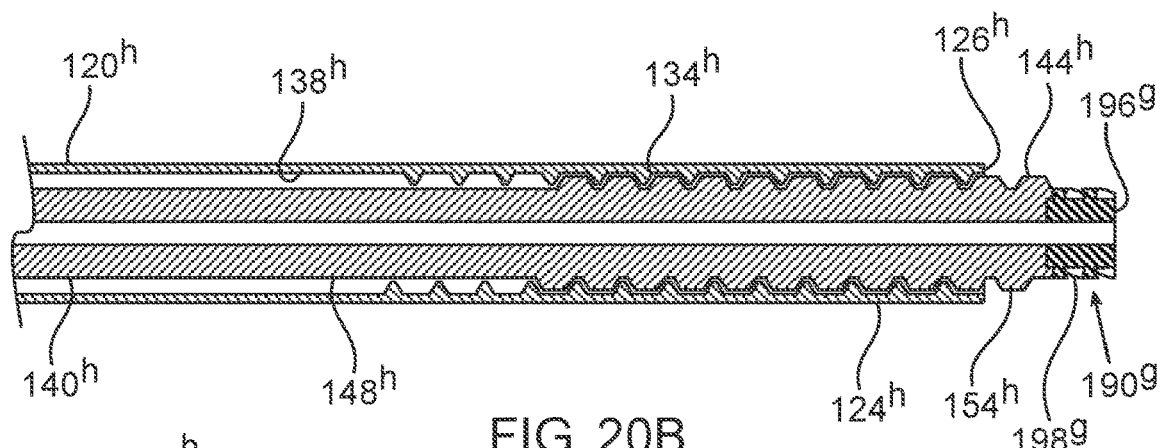
FIG. 20B constitutes a cross-sectional side view of the distal region of the non-penetrating tissue separator of FIG. 20A, in a second state.

Reference is now made to FIGS. 20A-20B. FIGS. 20A and 20B constitute a cross-sectional side views in a first state and a second state, respectively, of the non-penetrating tissue separator 100 equipped with an outer shaft 120$^h$ and a grabbing element 190$^g$ attached to an inner shaft 140$^h$, according to some embodiments.

According to some embodiments, the outer shaft distal portion 124$^h$ comprises outer shaft threaded portion 134$^h$ along at least a portion of its internal surface 130$^d$, and the inner shaft distal portion 144$^h$ comprises a matching inner shaft threaded portion 154$^h$ along at least a portion of its external surface 148$^h$, such that the inner shaft 140$^h$ is threadedly engaged with the outer shaft 120$^h$. According to some embodiments, the outer shaft threaded portion 134$^h$ extends proximally from the outer shaft distal lip 126$^h$. According to some embodiments, the inner shaft threaded portion 154$^h$ extends proximally from its connection interface with the grabbing element 190$^g$ (see FIGS. 20A-B).

According to some embodiments, rotation of the inner shaft 140$^h$ in one direction translates to an axial movement thereof in the distal direction 92 relative to the outer shaft 120$^h$, thereby causing the position of the grabbing element 190$^g$ to translate distally in direction 92.

According to some embodiments, the outer diameter of the grabbing element 190$^g$ is substantially equal to the outer diameter of the inner shaft threaded portion 154$^h$. According to some embodiments, the outer diameter of the inner shaft threaded portion 154$^h$ is larger than the outer diameter of the outer diameter of the grabbing element 190$^g$. According to some embodiments, the outer diameters of the grabbing element 190$^g$ and the inner shaft threaded portion 154$^h$ are configured to enable a tissue, such as the pericardium 14, when wrapped around the grabbing element 190$^g$, to further wrap around at least a portion of the inner shaft threaded portion 154$^h$ during continued rotation thereof.

Advantageously, the total length of the grabbing element 190$^g$ and the inner shaft threaded portion 154$^h$ offers a larger surface along which the pericardium 14 can be wrapped, thereby providing improved grip or engagement there between.

FIG. 20A illustrates the grabbing element 190$^g$ positioned in a first state, such that the distal surface 196$^g$ of the grabbing element 190$^g$ is proximal to or flush with the outer shaft distal lip 126$^h$.

FIG. 20B illustrates the grabbing element 190$^g$ positioned in a second state, wherein the proximal surface 194$^g$ of the grabbing element 190$^g$ is distally spaced from the outer shaft distal lip 126$^h$, and wherein at least a portion of the inner shaft threaded portion 154$^h$ also extends distally beyond the outer shaft distal lip 126$^h$.

Figure 21A:
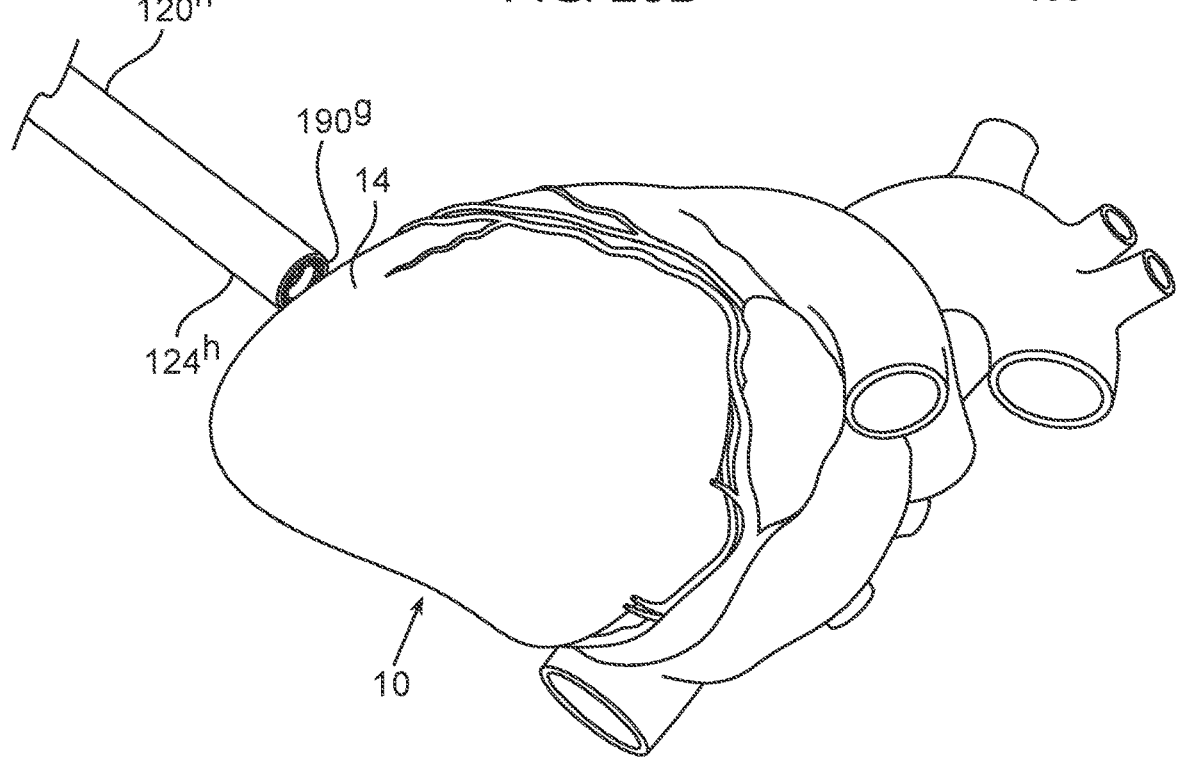
FIGS. 21A-21C illustrate different steps of a method of using the non-penetrating tissue separator, according to some embodiments.
Figure 21B:
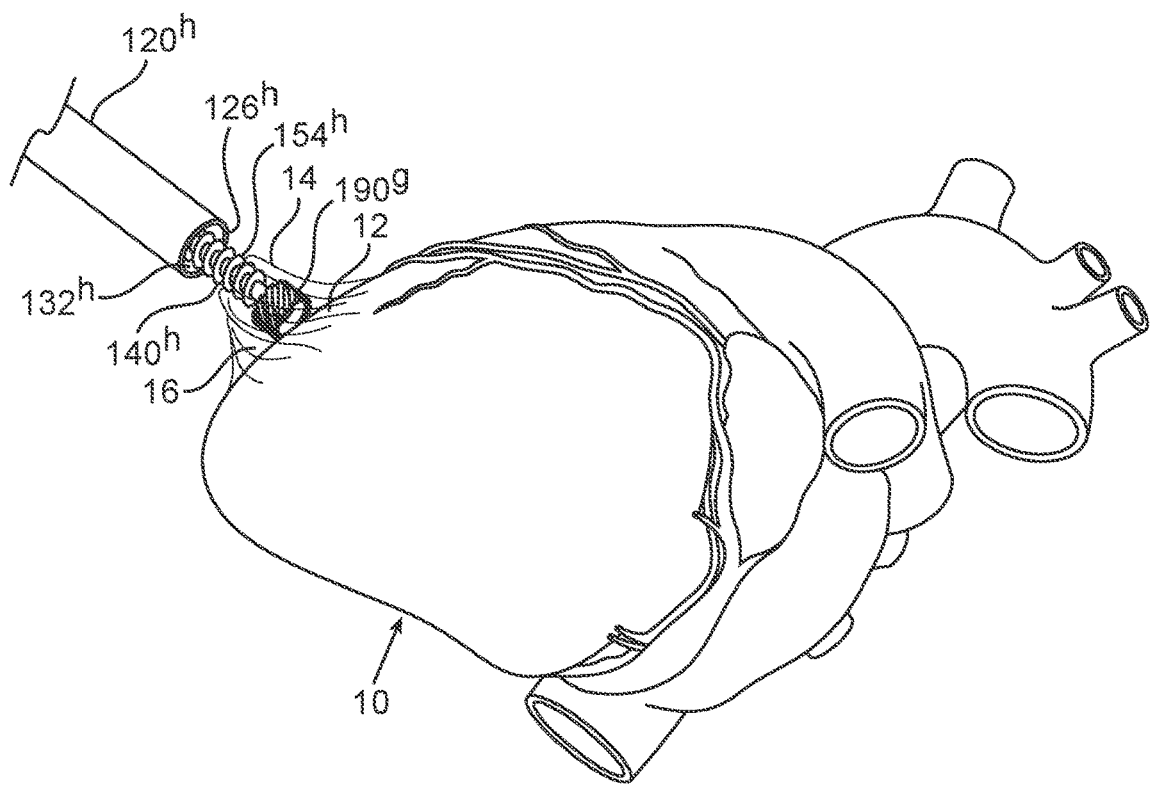
Figure 21C:
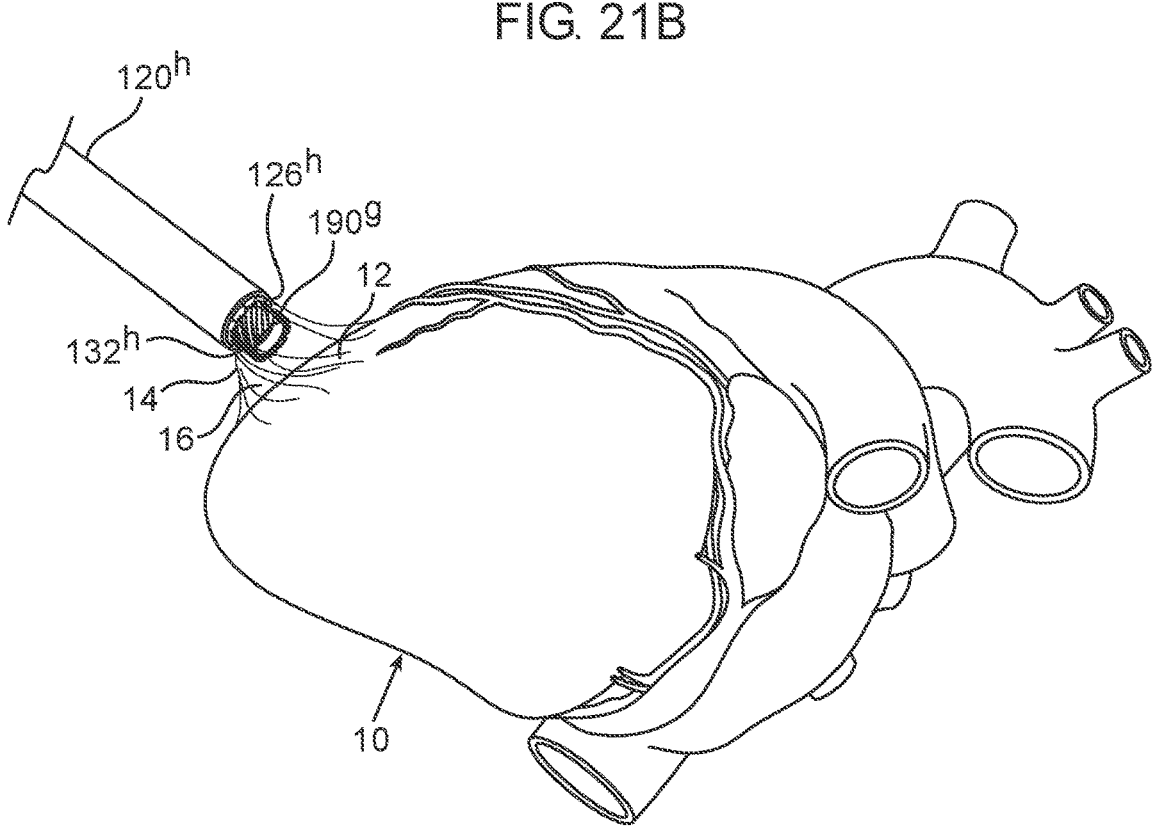

Reference is now made to FIGS. 21A-21C, depicting different steps of a method of using a non-penetrating tissue separator 100 equipped with an outer shaft 120$^h$ and a grabbing element 190$^g$ attached to an inner shaft 140$^h$, according to some embodiments. FIG. 21A shows a first step of the method, wherein the distal portion of the non-penetrating tissue separator 100, including at least a portion of the outer 120$^h$ and inner 140$^h$ shafts and the elongated grabbing element 190$^g$, is inserted into the patient's body and advanced distally toward the heart 10 of the patient, while the non-penetrating tissue separator 100 is in a first state, that is to say while the elongated grabbing element 190$^g$ is positioned proximal to outer shaft distal lip 126$^h$.

When the outer distal edge approximates the heart 10, such that it is at or near the pericardium 14, the operator maneuvers the non-penetrating tissue separator 100 to deploy the elongated grabbing element 190$^h$ from a first state to a second state. According to some embodiments, the elongated grabbing element 190$^h$ is positioned in the second state such that it is distally spaced from the outer shaft distal lip 126$^h$, and such that a portion of the inner shaft threaded portion 154$^h$ also extends distally beyond the outer shaft distal lip 126$^h$ (see FIG. 21B).

The elongated grabbing element 190$^g$ is distally advanced in the second state to contact the pericardium 14. When the elongated grabbing element 190$^g$ is at the pericardium 14, the operator maneuvers the non-penetrating tissue separator 100 to rotate the elongated grabbing element 190$^g$ around its central axis.

The surface features 188$^g$, during the rotational movement of the elongated grabbing element 190$^g$, cause the tissue to wrap around the elongated grabbing element 190$^g$, without being cut or punctured thereby. According to some embodiments, further rotation of the inner shaft 140$^h$ along with the elongated grabbing element 190$^g$ causes the tissue of the pericardium 14 to further wrap along the entire length of the grabbing element 190$^g$, as well as along a portion of the length of inner shaft threaded portion 154$^h$, as shown in FIG. 21B.

Once the tissue of the pericardium 14 is wrapped around the elongated grabbing element 190$^g$ and potentially along the inner shaft threaded portion 154$^h$, the operator maneuvers the non-penetrating tissue separator 100 to pull the elongated grabbing element 190$^g$ in the proximal direction to create the working pericardial space 16 (see FIG. 21C).

According to some embodiments, the elongated grabbing element 190$^g$ and the inner shaft threaded portion 154$^h$ are pulled in a proximal direction 94 until the pericardium 14 wrapped there along is pressed between the elongated grabbing element 190$^g$ and at least a portion of the outer shaft 120, thereby locking the wrapped pericardial tissue 14 there between.

According to some embodiments, the elongated grabbing element 190$^g$ and the inner shaft threaded portion 154$^h$ are pulled in a proximal direction 94 until the pericardium 14 wrapped there along is pressed between inner shaft threaded portion 154$^h$ and at least a portion of the outer shaft 120, thereby locking the wrapped pericardial tissue 14 there between.

According to some embodiments, the outer diameter of the wrapped pericardial tissue 14 is larger than the inner diameter of the outer shaft lumen 132, such that upon retraction, the wrapped pericardial tissue 14 is pressed between the a portion of the inner shaft threaded portion 154$^h$ and the outer shaft distal lip 126$^h$. According to some embodiments, the wrapped pericardial tissue 14 is pressed between the inner shaft threaded portion 154$^h$ and the outer shaft threaded portion 134$^h$.

According to some embodiments, the wrapped pericardial tissue 14 is pressed between the grabbing element circumferential surface 198$^g$ and the outer shaft internal surface 130$^h$. According to some embodiments, the wrapped pericardial tissue 14 is pressed between the grabbing element circumferential surface 198$^g$ and the outer shaft threaded portion 134$^h$.

According to some embodiments, the non-penetrating tissue separator 100 is equipped with an outer shaft 120$^h$ and a disc-shaped grabbing element 190 (such as grabbing elements 190$^a$-190$^e$) attached to an inner shaft 140$^h$ (embodiments not illustrated). In such embodiments, the disc-shaped grabbing element 190 is configured to grab and promote tissue 14 to wrap there along during rotation thereof, and promote further tissue wrapping along at least a portion of the length of the inner shaft threaded portion 154$^h$ upon further rotation. Aside from the length of a disc-shaped element 190 being shorter than that of the elongated grabbing element 190$^g$, the structure, operation and all embodiments described for FIGS. 20A-21C are similarly applicable.

Figure 22A:
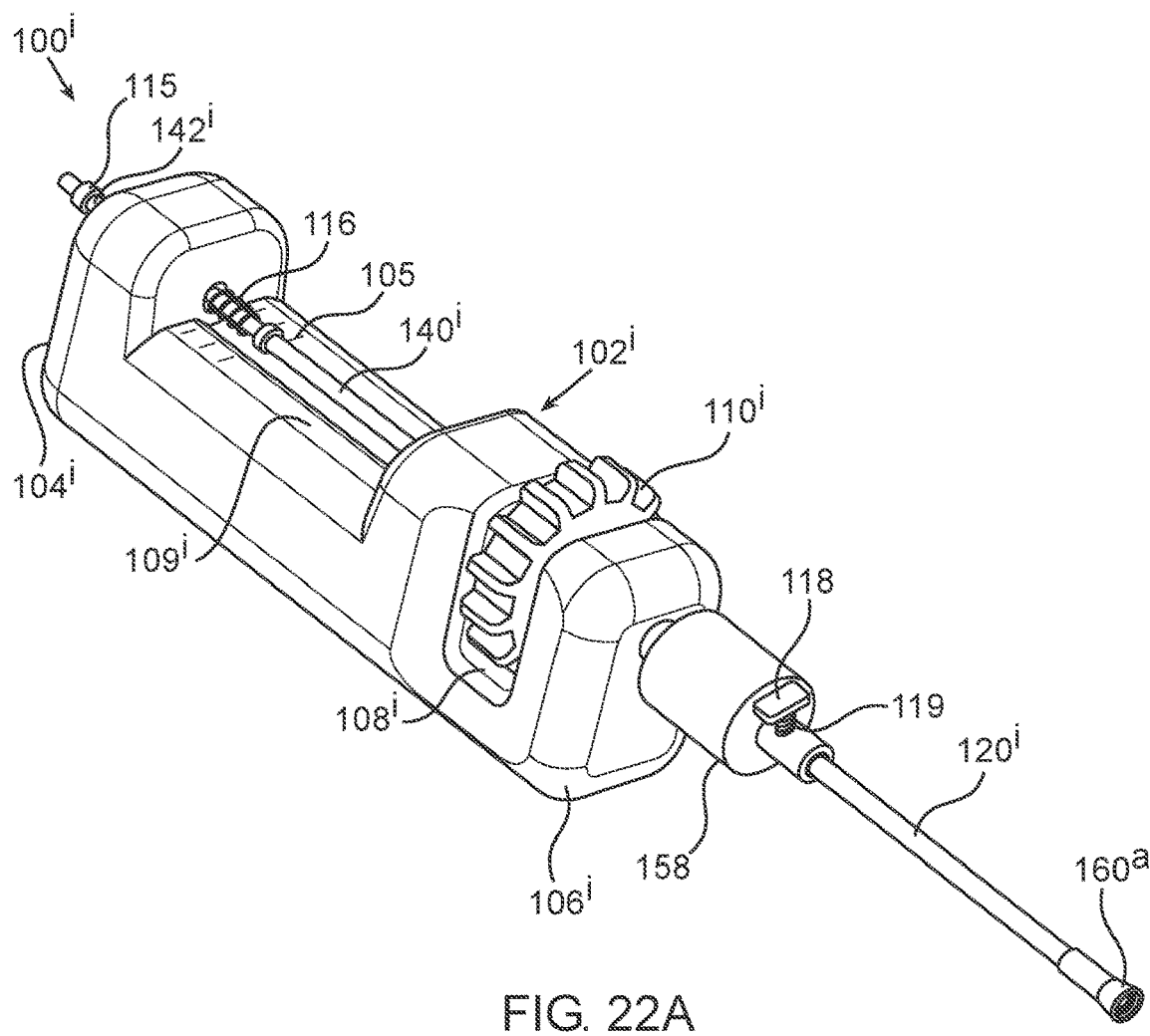
FIG. 22A constitutes a view in perspective of a non-penetrating tissue separator, according to some embodiments.

Reference is now made to FIGS. 22A-25. FIG. 22A constitute a view in perspective of a non-penetrating tissue separator 100$^i$, according to some embodiments. FIGS. 22B and 22C constitute cross-sectional side views in a first state and in a second state, respectively, of the non-penetrating tissue separator 100$^i$.

According to some embodiments, the non-penetrating tissue separator 100$^i$ comprises a latching mechanism configured to displace the relative axial positions between the outer shaft 120$^i$ and the inner shaft 140$^i$ between the first state and the second state.

According to some embodiments, the latching mechanism comprises a lever 156 pivotably movable about a pivot 157, a lever support body 158 comprising the pivot 157, and a grooved element 138 comprising at least two axially spaced grooves 139, such as the distal groove 139$^a$ and the proximal groove 139$^b$. Each groove 139 is configured to accommodate an end portion of the lever 156.

According to some embodiments, the grooved element 138 is fixedly attached to the handle 102$^i$, for example to the handle distal portion 106$^i$. According to some embodiments, the lever support body 158 is fixedly attached to the outer shaft 120$^i$, for example to the outer shaft external surface 128$^i$. According to some embodiments, the lever support body 158 is fixedly attached to the outer shaft distal portion 124$^i$.

According to some embodiments, the grooved element 138 is fixedly attached to the handle 102$^i$, for example to the handle distal portion 106$^i$. According to some embodiments, the grooved element 138 comprises an internal bore through which the inner shaft 140$^i$ can extend in an axial direction.

According to some embodiments, the latching mechanism further comprises a knob 118, connected to an end of the lever 156 opposite to its engagement end with the grooves 139 of the grooved element 138. According to some embodiments, the latching mechanism further comprises a knob spring 119 disposed between the knob 118 and the lever support body 158.

According to some embodiments, the lever support body 158 is comprises a first portion attached to the outer shaft external surface 128$^i$, and a second portion radially spaced from the outer shaft external surface 128$^i$, both portions connected to each other via an intermediate shoulder. According to some embodiments, the first portion of the lever support body 158 is formed as a cylinder, affixed around the outer shaft external surface 128$^i$. According to some embodiments, the second portion of the lever support body 158 is formed as a cylinder, configured to cover at least a portion of the grooved element 138 when positioned in at least one of the first state and the second state.

According to some embodiments, the intermediate shoulder of the lever support body 158 comprises the pivot 157. According to some embodiments, the knob spring 119 is disposed between the knob 118 and the first portion of the lever support body 158 (see FIGS. 22B-C).

Figure 22B:
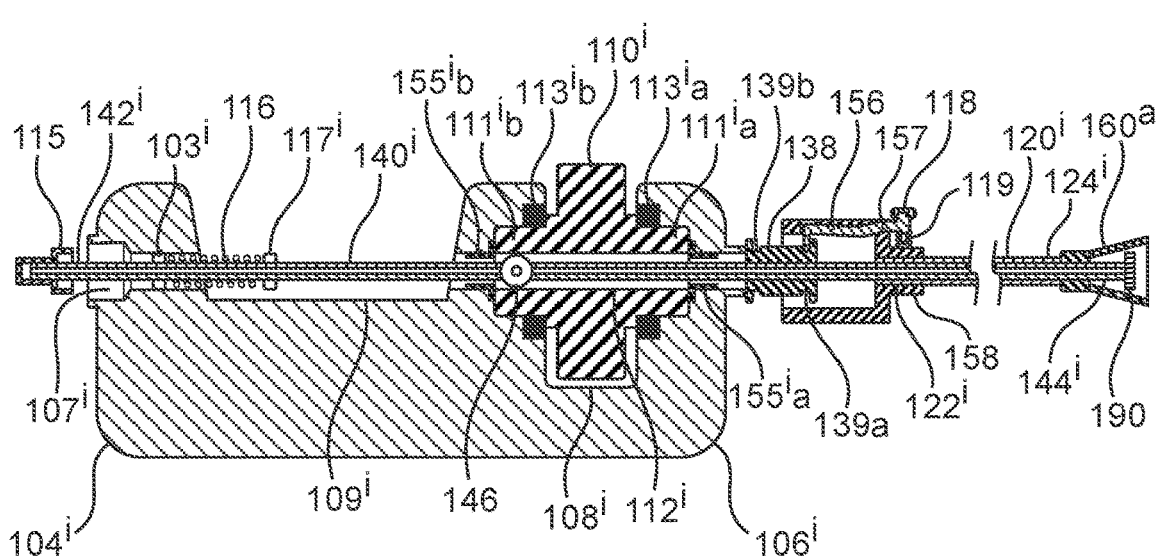
FIG. 22B constitutes a cross-sectional side view of the non-penetrating tissue separator of FIG. 22A, in a first state.

FIG. 22B shows the non-penetrating tissue separator 100$^i$ in the first state, wherein the grabbing element 190 is positioned proximal to the cone distal lip 174$^a$. The lever 156 is spring biased, via spring 119, into the distal groove 139$^a$. Since the lever 156 is attached, via the pivot 157 and the lever support body 158, to the outer shaft external surface 128$^i$, it prevents axial movement of the outer shaft 120$^i$ and the cone head 160$^a$ attached thereto, relative to the handle 102$^i$, as long as the lever 156 is retained in place. If the inner shaft 140$^i$ also remains stationary relative to the handle 102$^i$, the grabbing element 190 remains positioned in the first state.

Pushing the knob 118 to contract the knob spring 119 acts to pivot the lever about the pivot 157, thereby releasing the lever 156 from the distal groove 139$^a$ and enabling axial displacement of the outer shaft 120$^i$ relative to the handle 102$^i$. The outer shaft 120$^i$ can be retracted in the proximal direction 94 to expose the grabbing element 190, i.e. positioning it in the second state. The knob 118 can then be released so that the lever 156 can engage the proximal groove 139$^b$.

Figure 22C:
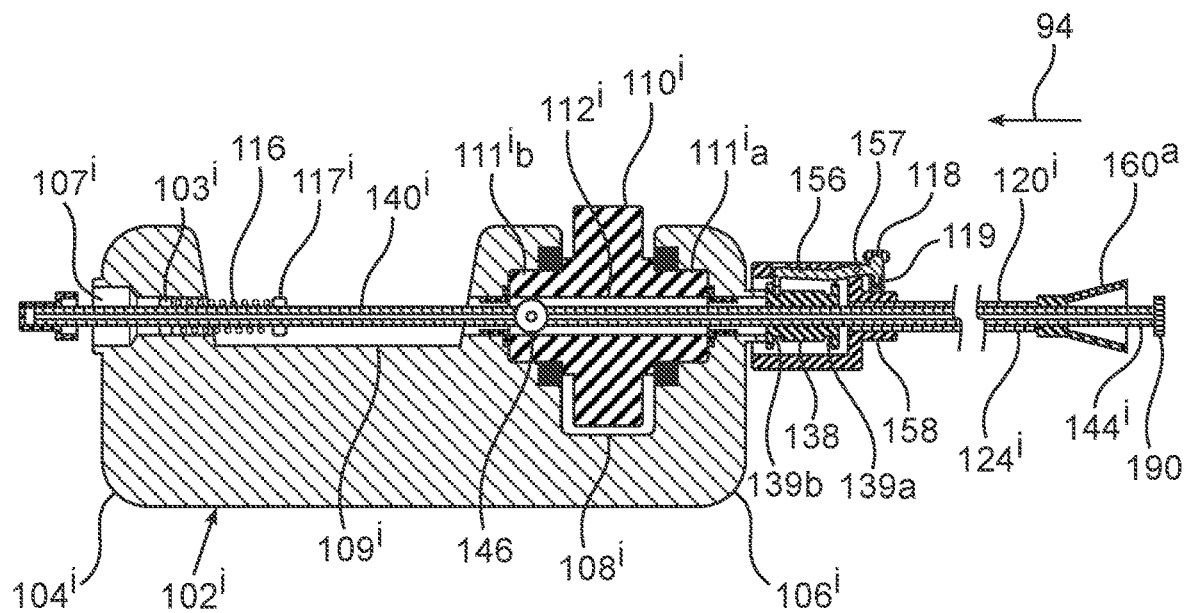
FIG. 22C constitutes a cross-sectional side view of the non-penetrating tissue separator of FIG. 22A, in a second state.

FIG. 22C shows the non-penetrating tissue separator 100$^i$ in the second state, wherein the grabbing element 190 is positioned distal to the cone distal lip 174$^a$. The lever 156 is spring biased, via spring 119, into the proximal groove 139$^b$. Since the lever 156 is attached, via the pivot 157 and the lever support body 158, to the outer shaft external surface 128$^i$, it prevents axial movement of the outer shaft 120$^i$ and the cone head 160$^a$ attached thereto, relative to the handle 102$^i$, as long as the lever 156 is retained in place. If the inner shaft 140$^i$ also remains stationary relative to the handle 102$^i$, the grabbing element 190 remains positioned in the second state.

The axial position of the distal groove 139$^a$ is configured to position the grabbing element 190 in the first state, when engaged with the lever 156. The axial position of the proximal groove 139$^b$ is configured to position the grabbing element 190 in the second state, when engaged with the lever 156.

While the embodiment of the non-penetrating tissue separator 100$^i$ illustrated in FIGS. 22A-C comprises a cone head 160$^a$, it will be clear that any other cone head 160 can be attached to the outer shaft 120$^i$, and that the outer shaft 120$^i$ can be also provided in a configuration devoid of a cone head 160.

Figure 23A:
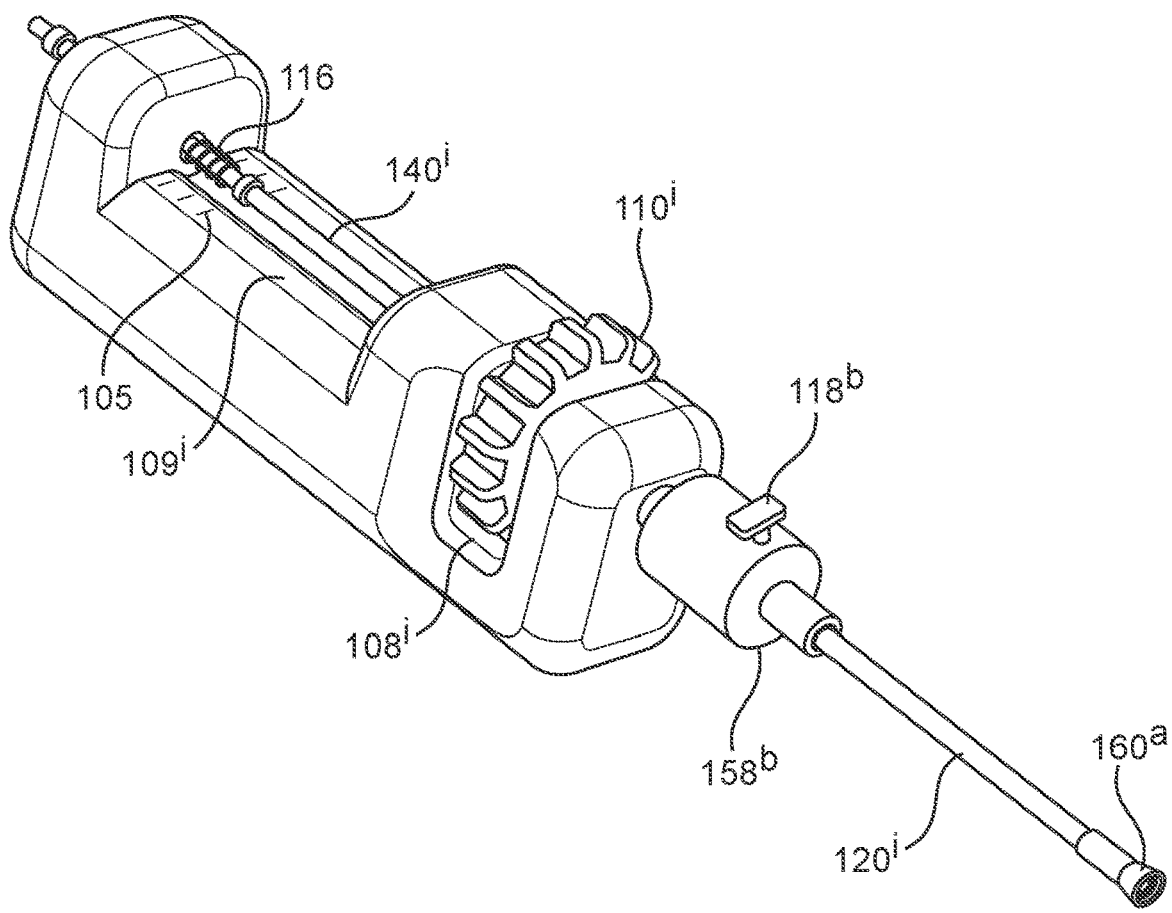
FIG. 23A constitutes a view in perspective of a non-penetrating tissue separator, according to some embodiments.
Figure 23B:
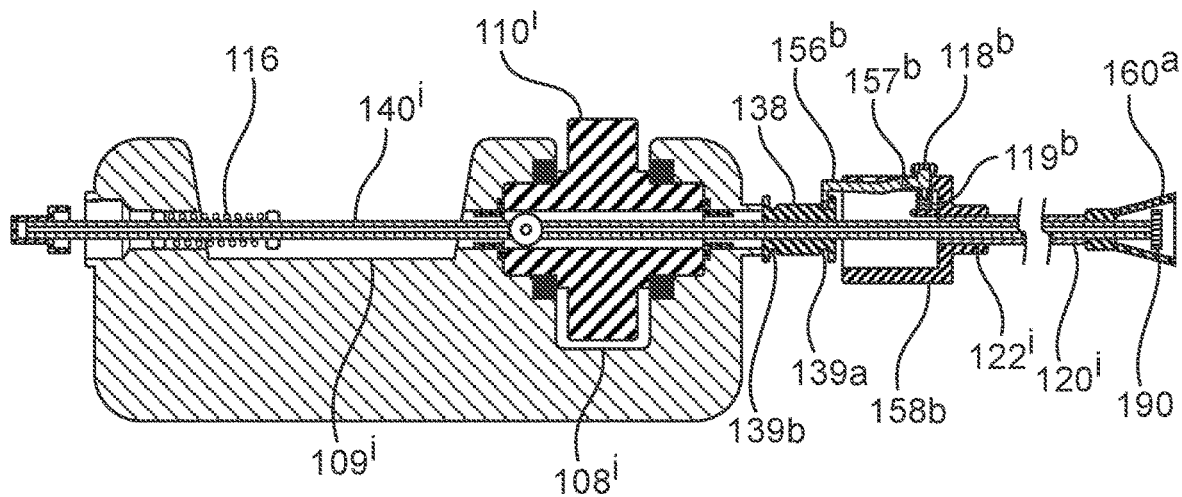
FIG. 23B constitutes a cross-sectional side view of the non-penetrating tissue separator of FIG. 22A, in a first state.
Figure 23C:
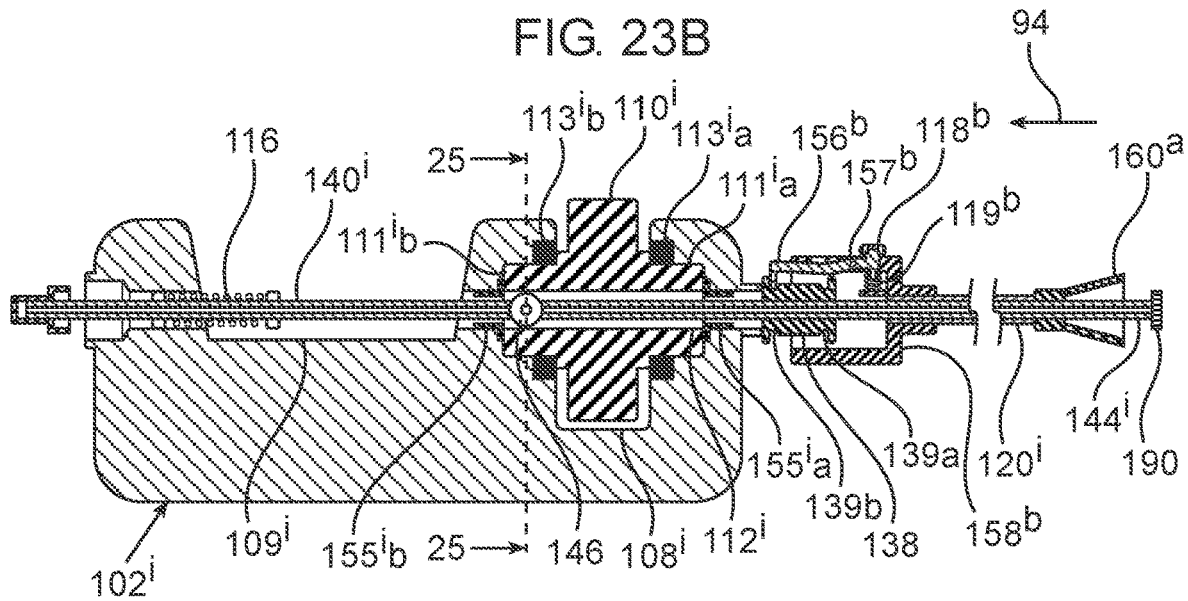
FIG. 23C constitutes a cross-sectional side view of the non-penetrating tissue separator of FIG. 23A, in a second state.

FIGS. 23A-C, analogous to the views of FIGS. 22A-C, show another embodiments of a non-penetrating tissue separator 100$^i$, wherein the second portion of the lever support body 158$^b$ comprises the pivot 157$^b$. In this exemplary embodiment, the knob 118$^b$ is positioned along the second portion of the lever support body 158$^b$, and the knob spring 119$^b$ is disposed between the knob 118$^b$ and an internal support within the second portion of the lever support body 158$^b$, which may be formed as an axial extension from the first portion of the lever support body 158$^b$ (see FIGS. 23A-B).

According to some embodiments, the handle 102$^i$ comprises a first handle niche 108$^i$, and a steering knob 110$^i$ disposed within the first handle niche 108$^i$. According to some embodiments the steering knob 110$^i$ comprises a steering knob internal bore 112$^i$, configured to accommodate the inner shaft 140$^i$ extending there-along, such that the inner shaft 140$^i$ is configured to axially move there through.

Figure 24A:
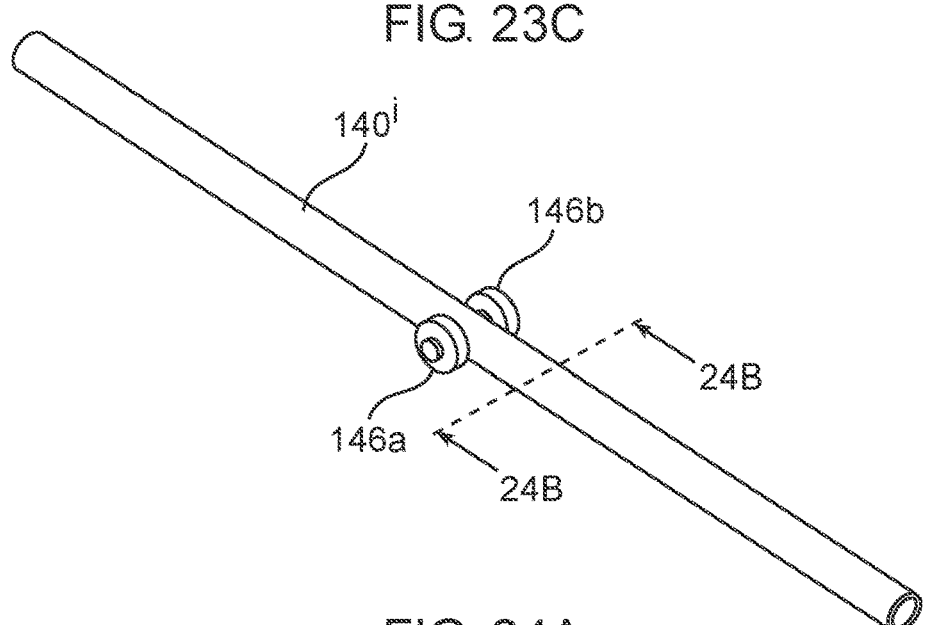
FIG. 24A constitutes a view in perspective of an inner shaft with roller bearings, according to some embodiments.
Figure 24B:
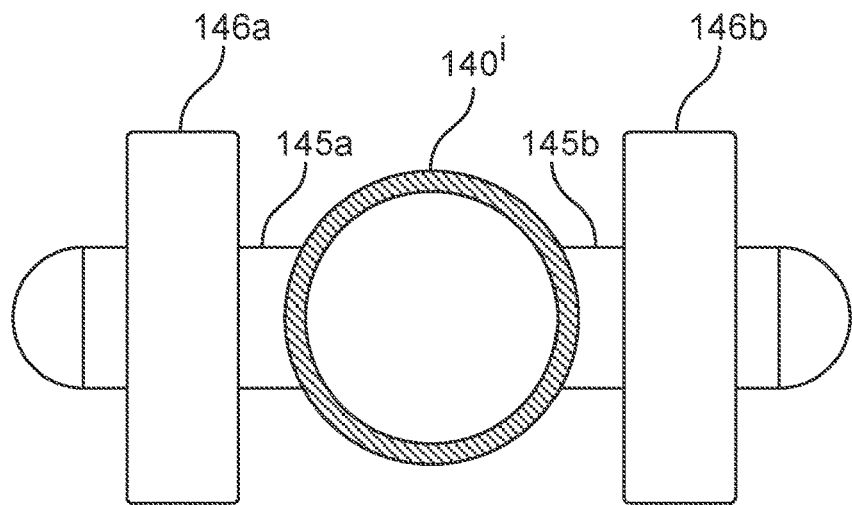
FIG. 24B constitutes a sectional view of the inner shaft of FIG. 24A from direction 24B-24B.

According to some embodiments, the inner shaft 140$^i$ is configured to axially role within the steering knob internal bore 112$^i$ via roller bearings 146 attached thereto. FIG. 24A shows a view in perspective of an inner shaft 140$^i$ with two roller bearings 146$^a$ and 146$^b$, which may be formed as wheels, as rollers and the like. FIG. 24B constitutes a sectional view from direction 24B-24B of FIG. 24A. Stems 145$^a$ and 145$^b$ connect the roller bearings 146$^a$ and 146$^b$ to the inner shaft 140$^i$.

Figure 25:
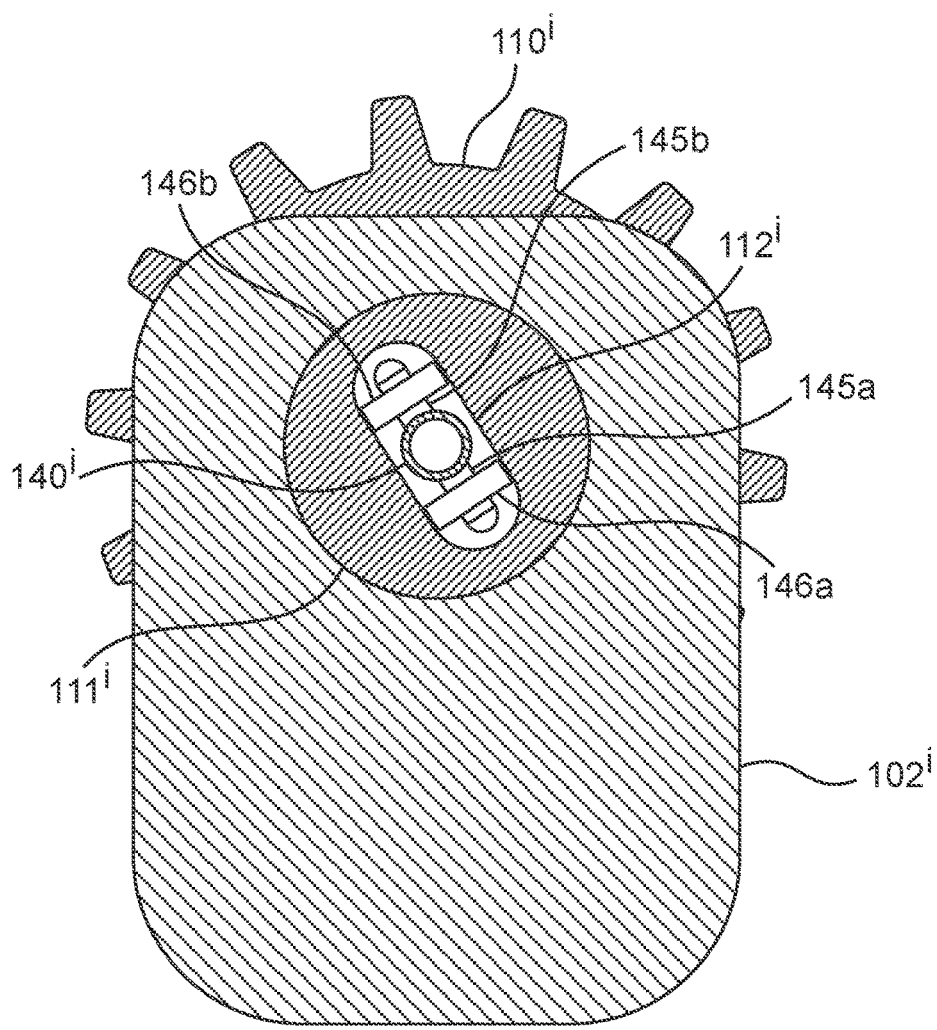
FIG. 25 constitutes a sectional view of the non-penetrating tissue separator of FIG. 23C from direction 25-25.

FIG. 25 constitutes a sectional view from direction 25-25 of FIG. 23C. The roller bearings 146 are configured to roll along the edges of the steering knob internal bore 112$^i$, thereby enabling axial movement of the inner shaft 140$^i$.

According to some embodiments, the inner shaft 140$^i$ comprises other components that promote or enable its axial movement within and along the steering knob internal bore 112$^i$, such as a flat sliding bearing (embodiments not shown).

According to some embodiments, the inner shaft 140$^i$ is configured to slide along the steering knob internal bore 112$^i$ without any mediating components there between. For example, the inner shaft external surface 148$^i$ can be provided with lubricated or low-friction surface (embodiments not shown).

The roller bearings 146$^a$ and 146$^b$ are preferable to other solutions as they can assist in providing a smoother movement of the inner shaft 140$^i$ along the steering knob internal bore 112$^i$.

According to some embodiments, the steering knob internal bore 112$^i$ is provided an elongated profile (see FIG. 25), wherein height is configured to closely match the diameter of the roller bearings 146, and wherein its width is configured to accommodate the roller bearings 146$^a$, 146$^b$ and their respective Stems 145$^a$, 145$^b$.

According to some embodiments, the steering knob 110$^i$ comprises steering knob axial extensions 111$^i$, such as the distal steering knob axial extension 111$^i$a and the proximal steering knob axial extension 111$^i$b, extending towards matching sockets within the distal and axial sidewalls of the first handle niche 108$^i$.

According to some embodiments, the proximal and distal walls of the first handle niche 108$^i$ comprise an internal axial bore configured to allow passage of the inner shaft 140$^i$ there through. According to some embodiments, the steering knob 110$^i$ is rotatable about its central axis within the first handle niche 108$^i$. According to some embodiments, the steering knob 110$^i$ is connected to the distal and proximal walls of the first handle niche 108$^i$ via bearings, such as slide bearings 113$^i$ and 155$^i$.

In the exemplary embodiments of FIGS. 22B-C and 23B-C, a distal slide bearing 113$^i$a is disposed between the distal steering knob axial extension 111$^i$a and the matching socket within the distal wall of the first handle niche 108$^i$, a proximal slide bearing 113$^i$b is disposed between the proximal steering knob axial extension 111$^i$b and the matching socket within the proximal wall of the first handle niche 108$^i$, a distal slide bearing 155$^i$a is disposed between the distal steering knob axial extension 111$^i$a and the internal axial bore within the distal wall of the first handle niche 108$^i$, and a proximal slide bearing 155$^i$b is disposed between the proximal steering knob axial extension 111$^i$b and the internal axial bore within the proximal wall of the first handle niche 108$^i$.

The slide bearings 113$^i$a, 113$^i$b, 155$^i$a, and 155$^i$b can assist in providing a smoother rotational movement of the steering knob 110$^i$ within the first handle niche 108$^i$. According to some embodiments, other types of bearing may be provided between the steering knob 110$^i$ and other structural components of the handle 102$^i$, such as roller bearings (embodiments not shown). According to some embodiments, the steering knob 110$^i$ is configured to rotate within the first handle niche 108$^i$ without any mediating components with other structural components of the handle 102$^i$. For example, the steering knob axial extensions 111$^i$ can be provided with lubricated or smooth low-friction surfaces (embodiments not shown).

According to some embodiments, the handle 102$^i$ further comprises a second handle niche 109$^i$, configured to enable visual exposure of at least a portion of the inner shaft 140$^i$ extending there-through. According to some embodiments, the second handle niche 109$^i$ is disposed between the proximal wall of the first handle niche 108$^i$ and the handle proximal portion 104$^i$. While the second handle niche 109$^i$ in the embodiments exemplified in FIGS. 22A-23C is positioned proximal to the first handle niche 108$^i$, according to some embodiments it can be positioned distal to the first handle niche 108$^i$ (embodiments not shown).

According to some embodiments, the handle proximal portion 104$^i$ comprises an internal proximal bore, extending from a handle inlet 107$^i$ at the proximal edge of the handle 102$^i$ to the second handle niche 109$^i$, configured to allow passage of the inner shaft 140$^i$ there through.

According to some embodiments, the non-penetrating tissue separator 100$^i$ further comprises at least one shaft spring, such as a first shaft spring 116 disposed between the inner shaft 140$^i$ and the handle 102$^i$, configured to provide resistance to a proximal displacement of the inner shaft 140$^i$.

According to some embodiments, the first shaft spring 116 is disposed around at least a portion of the inner shaft 140$^i$, such that one end of the first shaft spring 116 is attached to or abuts a portion of the inner shaft 140$^i$ or an element attached to the inner shaft 140$^i$, and the opposite end of the first shaft spring 116 is attached to or abuts a portion of the handle 102$^i$.

According to some embodiments, the inner shaft 140$^i$ comprises an inner shaft spring retainer 117$^i$, affixed to and extending radially outwards from the inner shaft external surface 148$^i$. According to some embodiments, the handle proximal portion 104$^i$ comprises a handle spring retainer 103$^i$, affixed to and extending radially inwards from its internal proximal bore (see FIGS. 22B-C). According to some embodiments, the first shaft spring 116 is disposed between the inner shaft spring retainer 117$^i$ and the handle spring retainer 103$^i$.

According to some embodiments, at least a portion of the shaft spring 116 is disposed along a portion of the inner shaft 140$^i$ visible through the second handle niche 109$^i$.

According to some embodiments, the inner shaft 140$^i$ is devoid of an inner shaft spring retainer 117$^i$, and the first shaft spring 116 is directly attached at an end thereof to the inner shaft 140$^i$, for example to the inner shaft external surface 148$^i$. According to some embodiments, the handle 102$^i$ is devoid of a handle spring retainer 103$^i$, and the first shaft spring 116 is directly attached at an end thereof to the handle 102$^i$, for example—to the internal proximal bore of the handle proximal portion 104$^i$ (embodiments not shown).

According to some embodiments, the first shaft spring 116 is disposed between the proximal edge of the inner shaft 140$^i$ and a portion of the handle 102$^i$ (embodiments not shown).

According to some embodiments, the first shaft spring 116 is disposed around at least a portion of the inner shaft 140$^i$, such that one end of the first shaft spring 116 is attached to or abuts a portion of the inner shaft 140$^i$ or an element attached to the inner shaft 140$^i$, and the opposite end of the first shaft spring 116 is attached to or abuts a second niche proximal wall 159$^i$a. (annotated in FIGS. 28A-C), (embodiments not shown).

According to some embodiments, the first shaft spring 116 is disposed around at least a portion of the inner shaft 140$^i$, such that one end of the first shaft spring 116 is attached to or abuts a portion of the inner shaft 140$^i$ or an element attached to the inner shaft 140$^i$, and the opposite end of the first shaft spring 116 is attached to or abuts a second niche distal wall 159$^i$b (annotated in FIGS. 28A-C), (embodiments not shown).

According to some embodiments, the non-penetrating tissue separator 100$^i$ comprises indicia 105, for indicating at least one of: the position of grabbing element 190 attached to the inner shaft 140$^i$, the force applied by the grabbing element 190 when pressed against an external surface such as the heart tissue, whether the tissue provides resistance to a proximal pull of the grabbing element 190, or whether the tissue has been grabbed by the grabbing element 190.

According to some embodiments, the second handle niche 109$^i$ comprises indicia 105, for indicating the position of grabbing element 190 attached to the inner shaft 140$^i$, or the force applied by the grabbing element 190 when pressed against the heart tissue. According to some embodiments, the indicia 105 includes markings of ranges, indicating whether the current position or the force applies by the grabbing element 190 on the tissue is within a safe or no-contact zone, within a desired safe contact zone, or within a risk-prone zone. According to some embodiments, the indicia 105 includes color-coded markings.

In use, the first shaft spring 116 retains the inner shaft 140$^i$ and the grabbing element 190 attached thereto, at a specific axial position as long as no external force is applied thereto. Once the distal end of the non-penetrating tissue separator 100$^i$ reaches the heart 10 and the non-penetrating tissue separator 100$^i$ is switched from the first state to the second state, the operator can maneuver the non-penetrating tissue separator 100$^i$ so as to approximate the grabbing element 190 to the pericardium 14, for example to ensure sufficient contact between the grabbing element distal surface 196 and the pericardium 14 prior to rotating the grabbing element 190 to wrap the tissue there along.

It is desirable to ensure sufficient contact between the grabbing element distal surface 196 and the pericardium 14, while avoiding excessive force application on the tissue.

When the grabbing element 190 is pressed against the heart tissue, such as the pericardium 14, the pressure acts to contract the first shaft spring 116 such that the inner shaft 140$^i$ is displaced in a proximal direction relative to the handle 102$^i$. According to some embodiments, the inner shaft 140$^i$ comprises a marking on its external surface 148$^i$, which can be compared against the indicia 105 to indicate the position of the grabbing element 190 or the force it applies on the tissue.

According to some embodiments, the inner shaft 140$^i$ comprises a structural feature that can be compared against the indicia 105 to indicate the position of the grabbing element 190 or the force it applies on the tissue. According to some embodiments, the inner shaft spring retainer 117$^i$ serves as a structural feature that can be compared against the indicia 105. According to some embodiments, the inner shaft spring retainer 117$^i$ comprises a structural feature that can be compared against the indicia 105 to indicate the position of the grabbing element 190 or the force it applies on the tissue.

According to some embodiments, the structural feature of the shaft spring 116 comprises a metering needle, which can be utilized in conjunction with markings or the indicia 105 to indicate the position of the grabbing element 190 or the force it applies on the tissue.

According to some embodiments, the structural feature of the inner shaft 140$^i$ comprises a metering needle, which can be utilized in conjunction with markings or the indicia 105 to indicate the position of the grabbing element 190 or the force it applies on the tissue.

According to some embodiments, the cover of the handle 102$^i$ comprises a metering needle, accompanied by markings or indicia 105, to indicate the position of the grabbing element 190 or the force it applies on the tissue.

According to some embodiments, as long as the grabbing element 190 does not apply sufficient force on the tissue, i.e. a force exceeding a predetermined value, the marking or the structural feature of the inner shaft 140$^i$ can be positioned against a zone of the indicia 105 representing a safe, no-contact position.

According to some embodiments, when the grabbing element 190 is pressed against the heart tissue, the first shaft spring 116 is sufficiently contracted such that the marking or the structural feature of the inner shaft 140$^i$ moves proximally to a position against a zone of the indicia 105 representing a safe contact position.

According to some embodiments, when the grabbing element 190 is pressed too hard against the heart tissue, for example in a manner that can harm the tissue, the first shaft spring 116 is further contracted such that the marking or the structural feature of the inner shaft 140$^i$ moves further in the proximal direction to a position against a zone of the indicia 105 representing a risk-prone position. The operator can readjust the force applied against the heart tissue accordingly.

According to some embodiments, the handle 102$^i$ comprises a cover configured to cover at least the second handle niche 109$^i$, so as to provide environmental protection to the exposed portion of the inner shaft 140$^i$ (embodiments not shown). According to some embodiments, the cover comprises the indicia 105.

The characteristics of the at least one shaft spring, including the first shaft spring 116, such as its size, material or spring coefficient k, can be chosen to provide the appropriate desired resistance for indicating whether the grabbing element 190 is pressed against the tissue such that it applies a moderate or excessive force thereon.

According to some embodiments, the at least one spring, such as the first shaft spring 116 is a compressions spring (see FIGS. 22A-23C). According to some embodiments, the at least one spring, such as the first shaft spring 116 is an expansion spring (embodiments not shown).

According to some embodiments, there is provided a kit comprising the non-penetrating tissue separator 100 and balloon catheter 40, configured to inflate a balloon distal to the non-penetrating tissue separator 100 in order to ensure easier delivery of the distal region of the non-penetrating tissue separator 100 through the patient's organs and tissues until reaching the patient's heart 10.

Figure 26A:
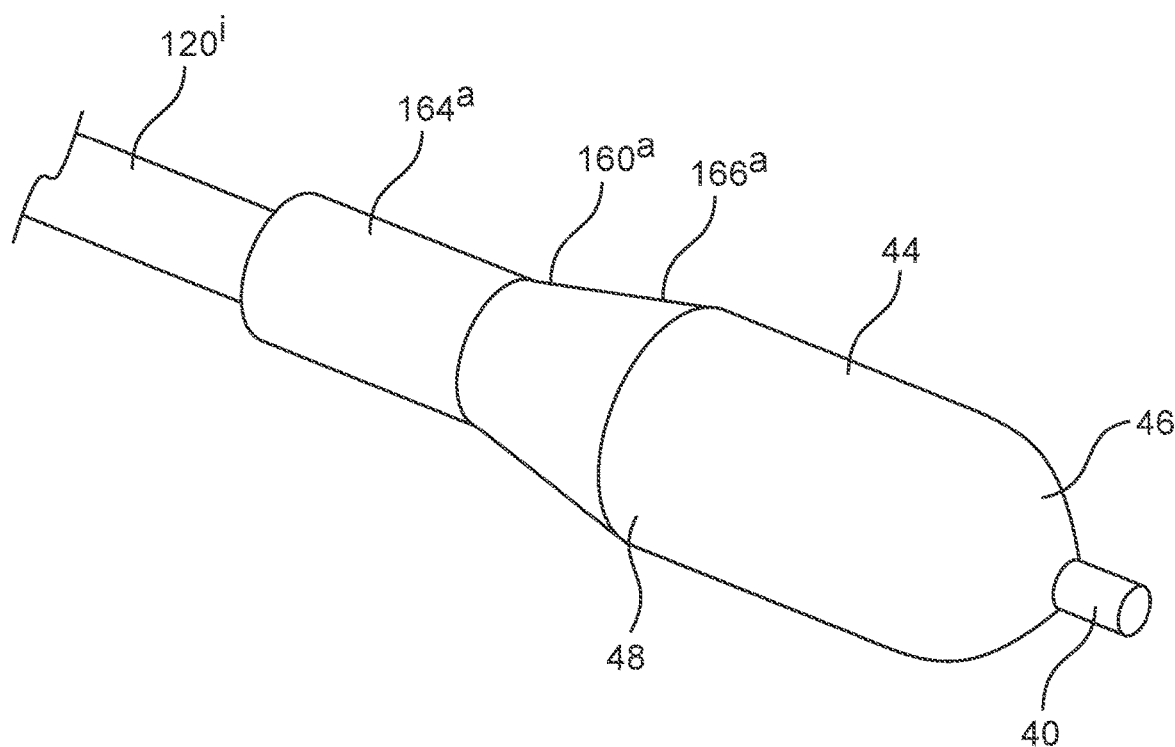
FIG. 26A constitutes a view in perspective of a balloon catheter having an inflated balloon distal to the non-penetrating tissue separator, according to some embodiments.
Figure 26B:
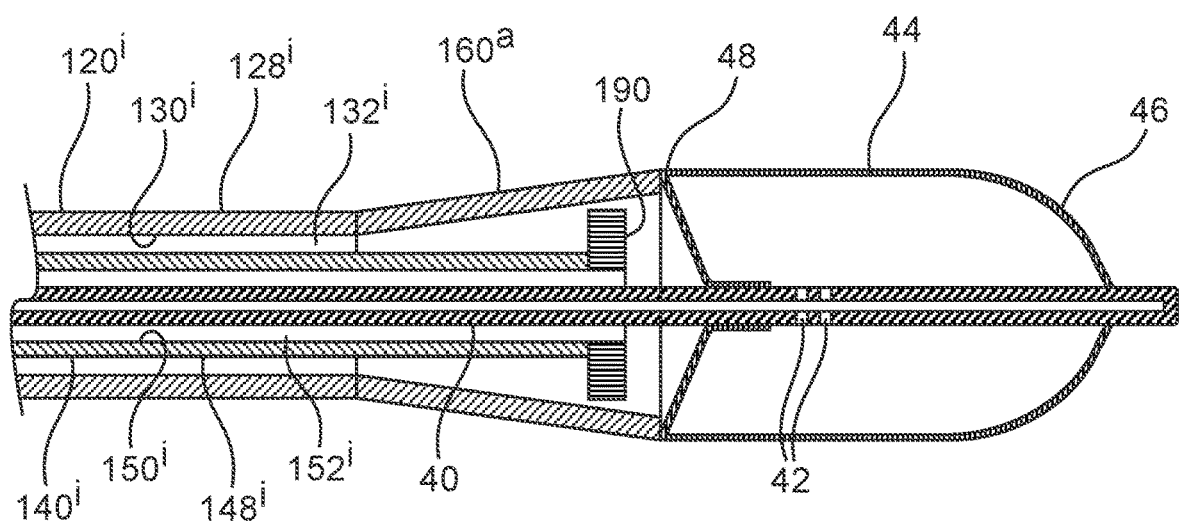
FIG. 26B constitutes a cross-sectional side view of the balloon catheter of FIG. 26A.

Reference is now made to FIGS. 26A-26B. FIGS. 26A and 26B constitute a view in perspective and a cross-sectional side view of a balloon catheter 40 having an inflated balloon 44 distal to the non-penetrating tissue separator 100$^i$. The balloon catheter 40 comprises an inflatable balloon 44 at its distal end. According to some embodiments, the balloon catheter 40 and the balloon 44 are configured to extend through the inner shaft lumen 152$^i$ when the balloon 44 is deflated.

According to some embodiments, the balloon catheter 40 includes balloon catheter aperture 42, through which gas or liquid, such as saline or carbon dioxide, can enter the internal volume of the balloon 44 in order to inflate it.

According to some embodiments, the balloon comprises a balloon distal portion 46 and a balloon proximal portion 48. According to some embodiments, the balloon distal portion is designed as a tapering or dome-shaped atraumatic front end when inflated, configured to assist in atraumatic advancement of the balloon 44 along with the distal region of the non-penetrating tissue separator 100$^i$ through the patient's organs, including hard tissues, without harming them.

According to some embodiments, the balloon proximal portion 48 is designed so as to provide a relatively smooth transition between the distal end of the non-penetrating tissue separator 100$^i$ and the balloon 44 when inflated.

According to some embodiments, the external diameter of the balloon, when inflated, is substantially equal to or larger than the external diameter of the cone distal lip 174$^a$.

While the balloon catheter 40 and the balloon 44 are shown in the exemplary embodiment of FIGS. 26A-B in conjunction with the non-penetrating tissue separator 100$^i$, it will be clear that the balloon catheter 40 along with the balloon 44 can be used in conjunction with any other embodiment or configuration of the non-penetrating tissue separator 100 disclosed throughout the specification.

Reference is now made to FIGS. 27A-27D, depicting different steps of a method of using the non-penetrating tissue separator 100$^i$ with a balloon catheter 40, according to some embodiments. FIG. 27A shows a first step of the method, wherein the balloon 44 is inflated distal to the distal portion of the non-penetrating tissue separator 100$^i$, advanced distally toward the heart 10 of the patient, while the non-penetrating tissue separator 100$^i$ is in a first state, that is to say while the grabbing element 190 is positioned proximal to cone distal lip 174$^a$, as well as proximal to the inflated balloon 44.

When the balloon 44 approximates the heart 10, it is deflated and retracted along with the balloon catheter 40 from the non-penetrating tissue separator 100$^i$. Once the balloon catheter is retracted, the distal portion of the non-penetrating tissue separator 100$^i$, including at least a portion of the outer 120$^i$ and inner 140$^i$ shafts, the grabbing element 190 and the cone head 160$^a$, can be further advance to place them near the pericardium 14.

The operator can then maneuver the non-penetrating tissue separator 100$^i$ to deploy the grabbing element 190 from a first state to a second state, for example by utilizing the latching mechanism to retract the outer shaft 120$^i$ along with the cone head 160$^a$ proximally, thereby exposing the grabbing element 190 now distally spaced from the cone distal lip 174$^a$ (see FIG. 27B).

According to some embodiments, in order to retract the cone head 160$^a$, the operator presses the knob 118 to release the lever from the distal groove 139$^a$, pulls the lever support body 158 along with the lever 156, and then releases the knob 118 in a position enabling the lever 156 to engage the proximal groove 139$^b$.

According to some embodiments, once the cone head 160$^a$ is retracted, the grabbing element 190 is positioned in the second state but is spaced from the pericardium 14. The operator can then maneuver the non-penetrating tissue separator 100$^i$ to further approximate the grabbing element 190 and press it against the pericardium 14, to ensure sufficient contact there between.

According to some embodiments, the operator adjusts the amount of pressure applied by the grabbing element 190 on the pericardium 14 according to the feedback from the indicia 105. The operator then maneuvers the non-penetrating tissue separator 100$^i$ to rotate the grabbing element 190 around its central axis, for example by rotating the steering knob 110$^i$.

The surface features 188, during the rotational movement of the grabbing element 190, cause the tissue to wrap around the grabbing element 190 as shown in FIG. 27B, without being cut or punctured thereby. Once the tissue of the pericardium 14 is wrapped around the grabbing element 190, the operator maneuvers the non-penetrating tissue separator 100$^i$ to reposition the grabbing element 190 from a second state to a first state, i.e. positioning it within the cone head 160$^a$, for example by utilizing the latching mechanism to push the outer shaft 120$^i$ along with the cone head 160$^a$ distally, thereby locking the wrapped pericardial tissue 14 between the grabbing element 190 and at least one of the cone head 160$^a$ and the outer shaft 120$^i$.

According to some embodiments, in order to push the cone head 160$^a$, the operator presses the knob 118 to release the lever from the proximal groove 139$^b$, pushes the lever support body 158 along with the lever 156, and then releases the knob 118 in a position enabling the lever 156 to engage the distal groove 139$^a$.

According to some embodiments, the operator maneuvers a non-penetrating tissue separator 100 to retract the grabbing element 190 in a proximal direction and to push a cone head 160 in a distal direction, simultaneously.

According to some embodiments, the wrapped pericardial tissue 14 is pressed between the grabbing element proximal surface 194 and the cone distal lip 174$^a$ (embodiment not shown). According to some embodiments, the wrapped pericardial tissue 14 is pressed between the grabbing element circumferential surface 198 and the cone inner surface 178$^a$, as shown both in FIGS. 27C and 27D.

According to some embodiments, the wrapped pericardium 14 is pressed between the grabbing element 190 and at least a portion of the outer shaft 120$^i$, thereby locking the wrapped pericardial tissue 14 there between. According to some embodiments, the wrapped pericardial tissue 14 is pressed between the grabbing element proximal surface 194 and the outer shaft distal lip 126$^i$.

Once the wrapped pericardium 14 is locked in place, the whole distal portion of the non-penetrating tissue separator 100$^i$ can be pulled in a proximal direction, to create the working pericardial space 16 (see FIG. 27C).

FIG. 27D shows a further step of advancing a distal needle portion 24 in direction 92 to puncture the portion of the pericardium 14 extending along the grabbing element inner opening 192, thereby providing access to the pericardial space 16.

According to some embodiments, as shown in FIG. 27D, the distal needle portion 24 cannot extend beyond the cone distal lip 174$^a$, for example due to the needle restraining element 26 preventing such extension, thereby ensuring that the needle will not cut or puncture any other tissue, such as the epicardium 12.

According to some embodiments, a needle provided with a curved or bent distal needle portion 24 can be rotated around its axis to orient the bent or curved distal portion 24 at a desired direction, thereby providing control of the advancement direction of a guidewire 30 passing there through.

Figure 28A:
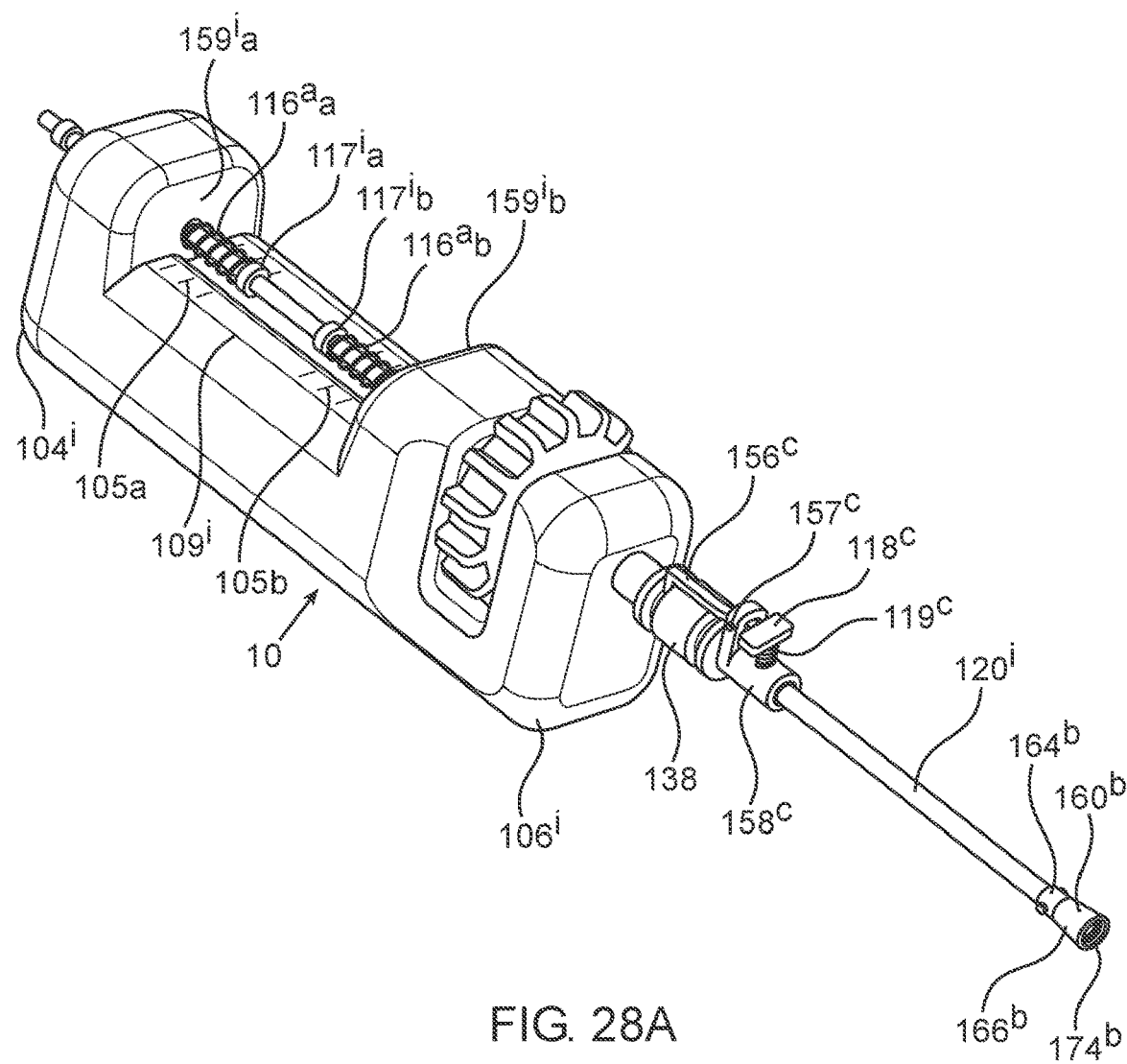
FIG. 28A constitutes a view in perspective of a non-penetrating tissue separator, according to some embodiments.
Figure 28B:
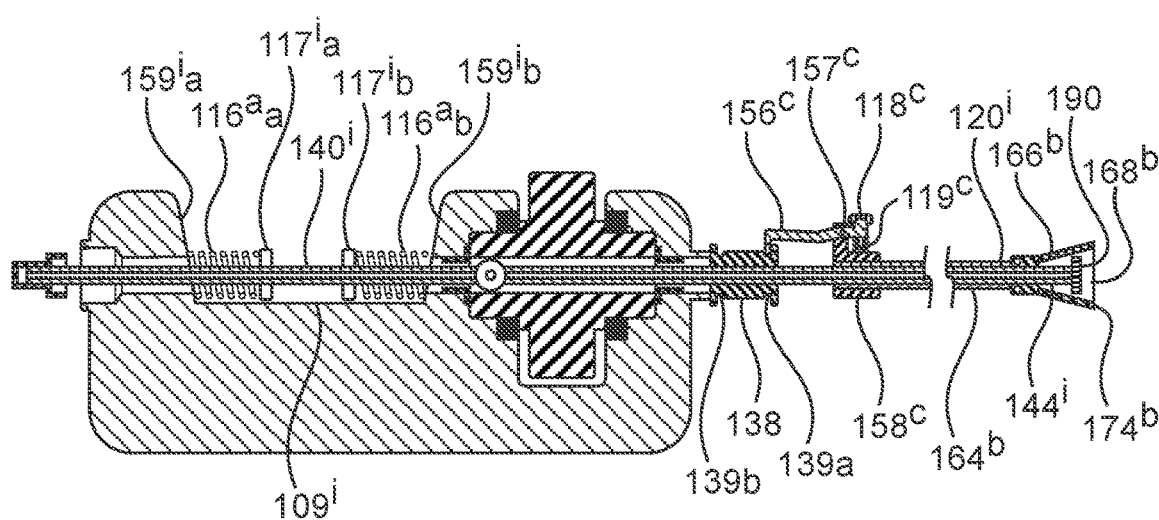
FIG. 28B constitutes a cross-sectional side view of the non-penetrating tissue separator of FIG. 28A, in a first state.
Figure 28C:
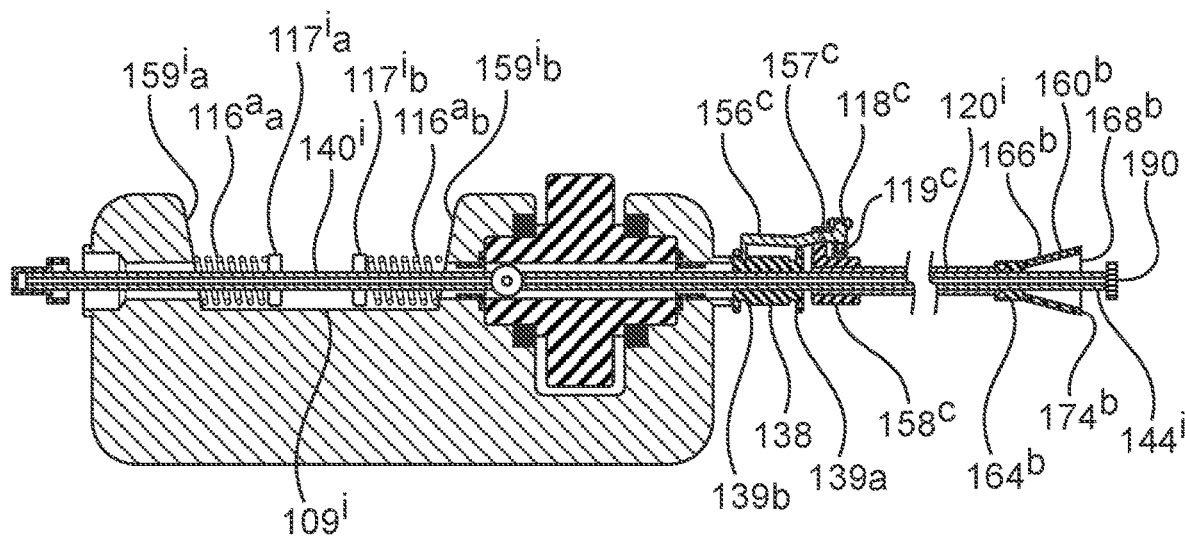
FIG. 28C constitutes a cross-sectional side view of the non-penetrating tissue separator of FIG. 28A, in a second state.

FIGS. 28A-C, analogous to the views of FIGS. 22A-C, show another embodiments of a non-penetrating tissue separator 100$^i$, having two opposing shaft springs 116$^a$, such as the first shaft spring 116$^a$a and the second shaft spring 116$^a$b. The first shaft spring 116$^a$a is similar in structure and function to the first shaft spring 116 described herein above for FIGS. 22A-23C. According to some embodiments, the handle 102$^i$ is devoid of a handle spring retainer 103$^i$, and the first shaft spring 116 or 116$^a$a is directly attached at an end thereof to the handle 102$^i$, for example—to second niche proximal wall 159$^i$a. (see FIGS. 28A-C).

According to some embodiments, the second shaft spring 116$^a$b is disposed between the inner shaft 140$^i$ and the handle 102$^i$, configured to provide resistance to a distal displacement of the inner shaft 140$^i$. According to some embodiments, the second shaft spring 116$^a$b is disposed around at least a portion of the inner shaft 140$^i$.

According to some embodiments, the inner shaft 140$^i$ comprises two inner shaft spring retainers 117$^i$a and 117$^i$a, each of which is affixed to and extending radially outwards from the inner shaft external surface 148$^i$. According to some embodiments, the first shaft spring 116$^{aa}$ is disposed between the first inner shaft spring retainer 117$^i$a and the handle 102$^i$, such as between the first inner shaft spring retainer 117$^i$a and the second niche proximal wall 159$^i$a, while the first shaft spring 116$^a$b is disposed between the second inner shaft spring retainer 117$^i$b and the handle 102$^i$, such as between the second inner shaft spring retainer 117$^i$b and the second niche distal wall 159$^i$b.

According to some embodiments, the second handle niche 109$^i$ comprises first indicia 105a configured to indicate proximal displacements of the inner shaft 140$^i$ indicative of forces applied thereby in the distal direction, and second indicia 150b configured to indicate distal displacements of the inner shaft 140$^i$ indicative of forces applied thereby in the proximal direction.

According to some embodiments, the lever support body 158$^c$ is devoid of a second portion. According to some embodiments, the first portion of the lever support body 158$^c$ is formed as a cylinder, affixed around the outer shaft external surface 128$^i$, having a radial extension protruding radially outwards, comprising the pivot 157$^c$. In such embodiments, the knob 118$^c$ is positioned over the first portion of the lever support body 158, and the knob spring 119$^c$ disposed between the knob 118$^c$ and the first portion of the lever support body 158.

According to some embodiments, the outer shaft 120, the inner shaft 140, the cone head 160 and the grabbing element 190 are coaxial in a free state, defined as a state wherein no external force is acting against either the cone head 160 or the grabbing element 190.

Figure 29A:
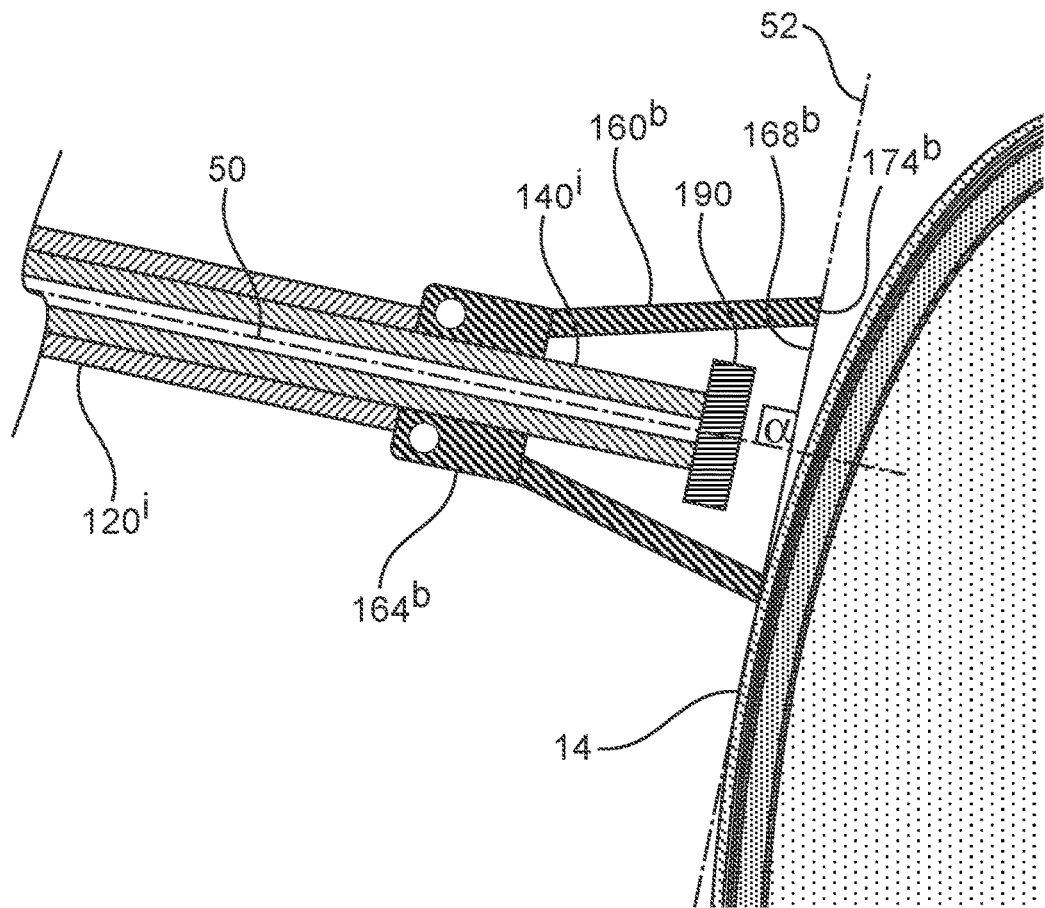
FIG. 29A constitutes a cross-sectional side view of a distal portion of the non-penetrating tissue separator equipped with a tiltable cone head in an un-tilted cone state, according to some embodiments.
Figure 29B:
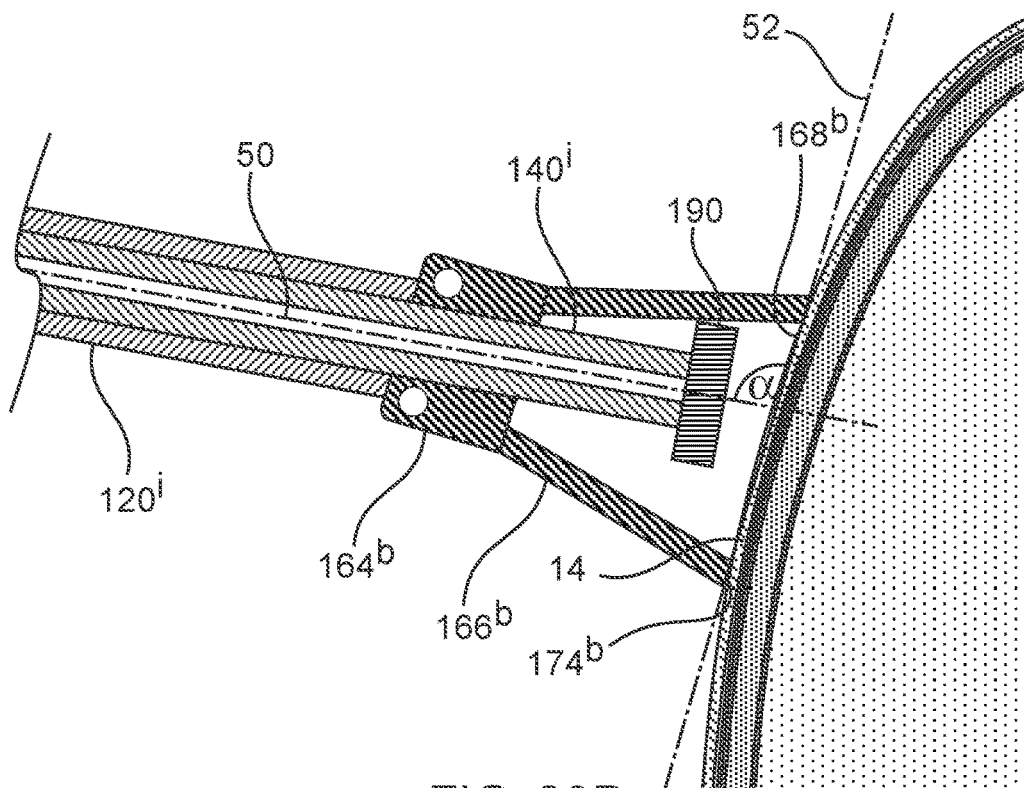
FIG. 29B constitutes a cross-sectional side view of a distal portion of the non-penetrating tissue separator equipped with a tiltable cone head in a tilted cone state, according to some embodiments.

Reference is now made to FIGS. 29A-29B. FIGS. 29A-29B constitute cross-sectional side views of a distal portion of the non-penetrating tissue separator 100$^i$ equipped with a tiltable cone head 160$^b$ in un-tilted and tilted cone states, respectively, according to some embodiments. The non-penetrating tissue separator 100$^i$ is positioned in FIG. 29A in the vicinity of the heart 10, wherein the centerline of the cone head 160$^b$ coincides with the centerline 50 of the outer shaft 120$^i$. The un-tilted cone state of the cone head 160$^b$ shown in FIG. 29A is a state wherein the centerline 50 of the outer shaft 120$^i$ is also common with the centerline of the centerline of the cone head 160$^b$, and is normal to the cone head front plane 52 defined by the cone distal lip 174$^b$.

In some cases, as shown in FIG. 29A, the cone head front plane 52 is angled relative to the plane of the pericardium 14 adjacent the cone opening 168$^b$ when the cone head 160 approaches the heart 10, such that the cone head 160$^b$ contacts the pericardium 14 along a relatively limited portion of the circumference of the cone distal lip 174$^b$, for example—along less than 50% of the circumferential length of the cone distal lip 174$^b$.

According to some embodiments, the cone head 160 is configured to tilt or bend relative to the outer shaft 120, such that the centerline of the cone head 160 can be angled relative to the centerline of the outer shaft 120. In a tilted or bent cone state (such as shown in FIG. 29B), the centerline of the cone head 160 is angled relative to the centerline 50 of the outer shaft 120. The bent or tilted cone state can be achieved, by way of example, by further approximating the cone head 160 towards the heart wall, thereby applying pressure against the cone distal lip 174.

According to some embodiments, the cone head 160 is pivotably attached to the outer shaft 120 (see FIGS. 29A-B). According to some embodiments, the cone proximal portion 164 is pivotably attached to the outer shaft distal portion 124.

FIG. 29B shows an embodiment of the cone head 160$^b$ tilted relative to the outer shaft distal portion 124$^i$ such that the cone head front plane 52, now angled at an angle α relative to the centerline 50 of the outer shaft 120$^i$, is substantially congruent to the adjacent plane of the pericardium 14, such that the cone head 160$^b$ contacts the pericardium substantially along the entire circumference of the cone distal lip 174$^b$.

According to some embodiments, at least a portion of the cone head 160, such as the cone proximal portion 164, comprises a flexible material, enabling it to bend relative to the outer shaft distal portion 124 (embodiments not shown). According to some embodiments, at least a portion of the cone head 160, such as the cone proximal portion 164, comprises a shape-memory material, such as Nitinol.

According to some embodiments, the non-penetrating tissue separator 100 further comprises at least one spring at the attachment between the cone proximal portion 164 and the outer shaft distal portion 124 (embodiments not shown).

A tilted cone state or a bent cone state, as used herein, are interchangeable, and refer to a state wherein the centerline of the cone head 160 is angled relative to the centerline of the outer shaft 120.

According to some embodiments, the cone head 160 is configured to transition between an un-tilted or an un-bent cone state when no external force is acting there against, and a respective tilted or bent cone state when subjected to an external force, such as being pressed against a distal surface.

While the cone head 160$^b$ is shown in the exemplary embodiment of FIGS. 29A-B in conjunction with the non-penetrating tissue separator 100$^i$, it will be clear that the cone head 160$^b$ can be used in conjunction with any other embodiment or configuration of the non-penetrating tissue separator 100 disclosed throughout the specification.

Figure 30:
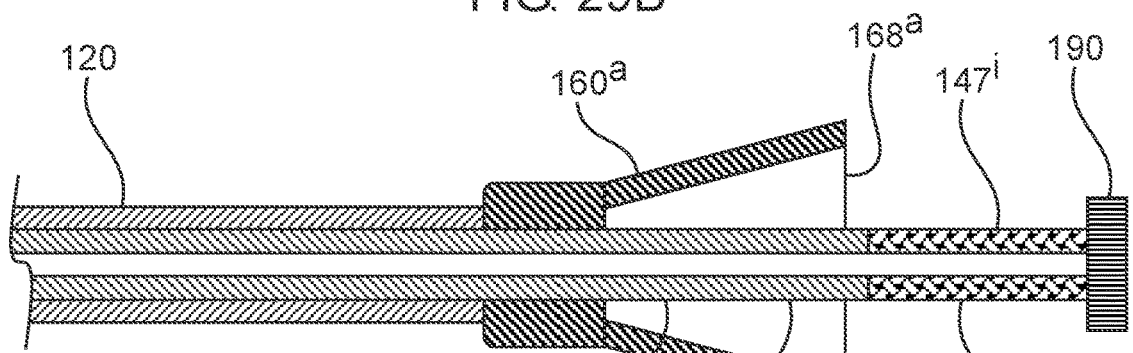
FIG. 30 constitutes a cross-sectional side view of a distal portion of the non-penetrating to tissue separator equipped with a bendable inner shaft, according to some embodiments.
Figure 31:
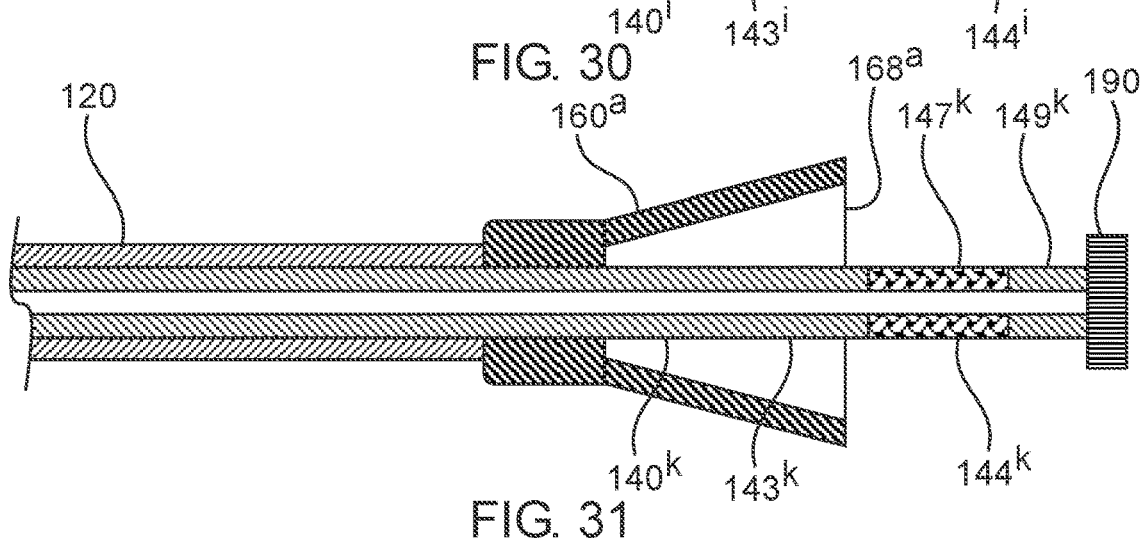
FIG. 31 constitutes a cross-sectional side view of a distal portion of the non-penetrating tissue separator equipped with a bendable inner shaft, according to some embodiments.
Figure 32:
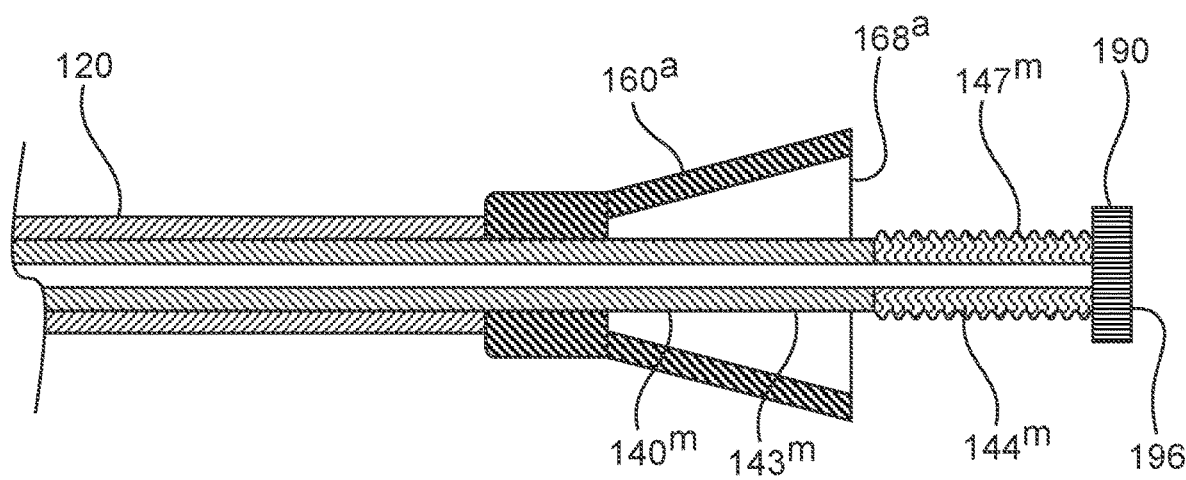
FIG. 32 constitutes a cross-sectional side view of a distal portion of the non-penetrating tissue separator equipped with a bendable inner shaft, according to some embodiments.
Figure 33A:
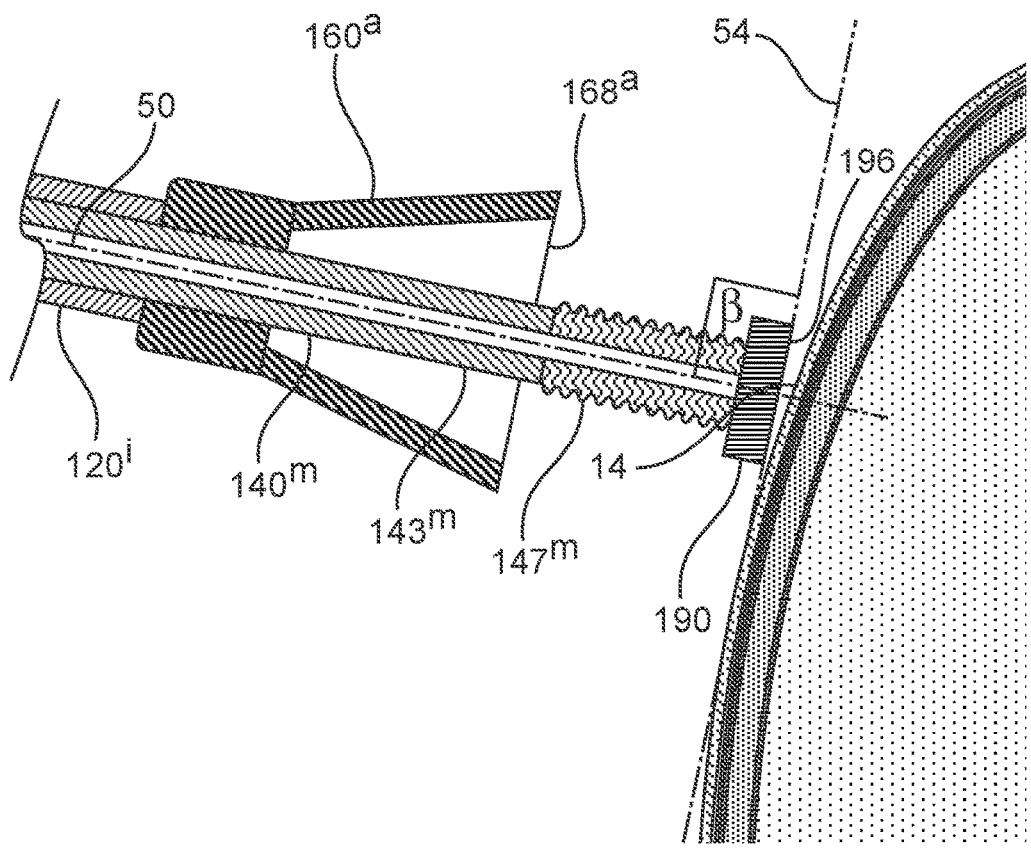
FIG. 33A constitutes a cross-sectional side view of a distal portion of the non-penetrating tissue separator equipped with a bendable inner shaft in an unbent shaft state, according to some embodiments.
Figure 33B:
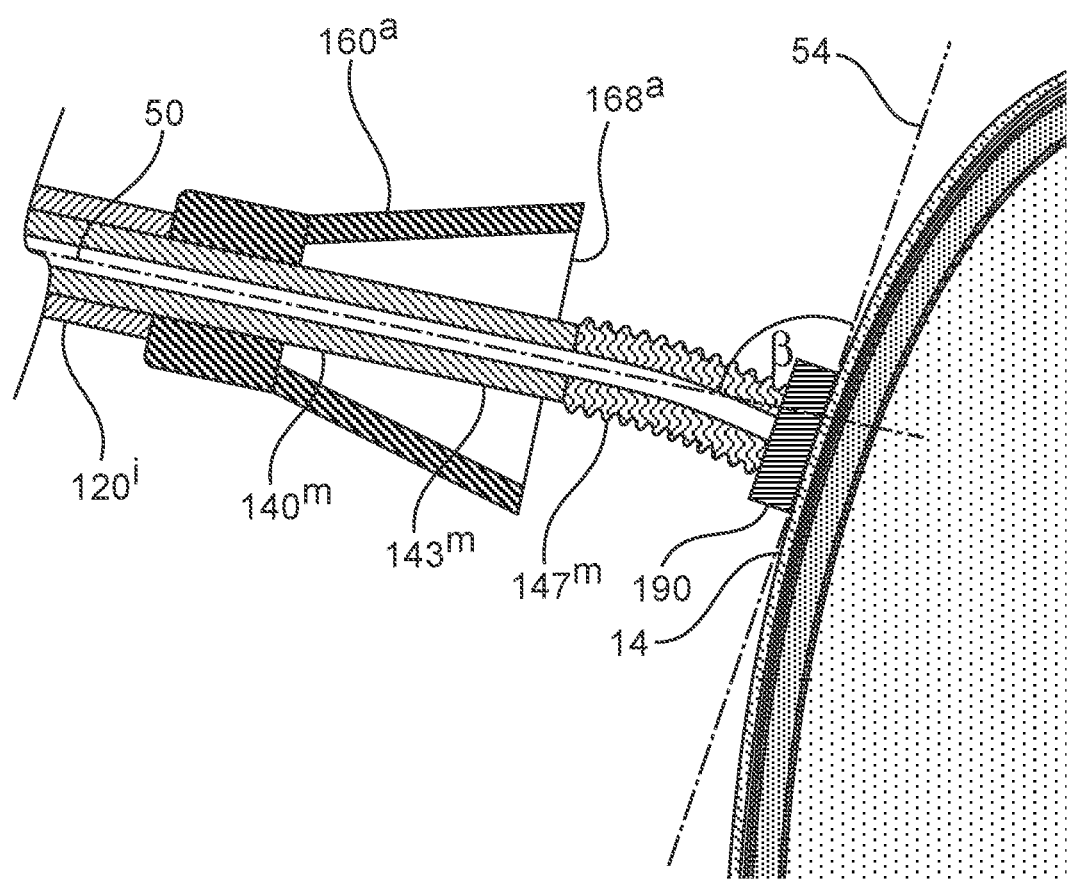
FIG. 33B constitutes a cross-sectional side view of a distal portion of the non-penetrating tissue separator equipped with a bendable inner shaft in a bent shaft state, according to some embodiments.

Reference is now made to FIGS. 30-33B. FIGS. 30-32 constitute cross sectional side views of a distal portion of the non-penetrating tissue separator 100 equipped with a bendable inner shaft 140$^j$, 140$^k$ and 140$^m$, respectively, according to some embodiments. FIGS. 33A-33B constitute cross-sectional side views of a distal portion of the non-penetrating tissue separator 100$^i$ equipped with the bendable inner shaft 140$^m$ in unbent and bent shaft states, respectively, according to some embodiments.

The non-penetrating tissue separator 100$^i$ is positioned in FIG. 33A in the vicinity of the heart 10 in the second state, wherein the centerline of the grabbing element 190 coincides with the centerline 50 of the outer shaft 120$^i$. The unbent shaft state of the inner shaft 140$^m$ shown in FIG. 33A is a state wherein the centerline 50 of the outer shaft 120$^i$ is also common with the centerline of the grabbing element 190, and is normal to the grabbing element front plane 54 defined by the grabbing element distal surface 196.

In some cases, as shown in FIG. 33A, the grabbing element front plane 54 is angled relative to the plane of the pericardium 14 adjacent the grabbing element 190 when approached the heart 10, such that the grabbing element 190 contacts the pericardium 14 along a relatively limited portion of the circumference of the grabbing element distal surface 196, for example—along less than 50% of the circumferential length of the grabbing element distal surface 196.

According to some embodiments, the distal end of the inner shaft 140 is configured to bend relative to the outer shaft 120, such that the centerline of the grabbing element 190 attached thereto can be angled relative to the centerline of the outer shaft 120. In a bent shaft state (such as shown in FIG. 33B), the centerline of the grabbing element 190 is angled relative to the centerline 50 of the outer shaft 120. The bent shaft state can be achieved, by way of example, by further approximating the grabbing element 190 towards the heart wall, thereby applying pressure against the grabbing element distal surface 196.

According to some embodiments, the inner shaft 140 comprises a bendable inner shaft portion 147 and a rigid inner shaft portion 143. The bendable region 147 is a portion of the inner shaft 140 which bends when a force higher than a first threshold F1 is applied thereto. According to some embodiments, the rigid inner shaft portion 143 does not bend when a force higher than a first threshold F1 is applied thereto. According to some embodiments, the rigid inner shaft portion 143 does not bend when a force higher than a first threshold F1 but lower than a second threshold F2 is applied thereto, yet might bend when a force higher than a second threshold F2 is applied thereto.

According to some embodiments, the bendable inner shaft portion 147 extends along at least a portion of the inner shaft 140 bound within the cone head 160 and/or extending distally from the cone opening 168 in the second state. According to some embodiments, the bendable inner shaft portion 147 extends along at least a portion of the inner shaft 140 extending distally from the cone proximal portion 164 in the second state. According to some embodiments, the rigid inner shaft portion 143 extends along the entire length of the inner shaft 140 proximal to the bendable inner shaft portion 147.

According to some embodiments, the bendable inner shaft portion 147 comprises a material which is more flexible than the material of the rigid inner shaft portion 143. According to tome embodiments, the bendable inner shaft portion 147 comprises a spring (embodiment not shown). According to tome embodiments, the bendable inner shaft portion 147 comprises a plurality of slots or bellows that impart flexibility thereof.

FIG. 30 shows an embodiment of an inner shaft 140$^j$ comprising a bendable inner shaft portion 147$^j$ extending proximally from the grabbing element proximal surface 194, and a rigid inner shaft portion 143$^j$ extending proximally from the proximal end of the bendable inner shaft portion 147$^j$. The bendable inner shaft portion 147$^j$ in the exemplary embodiment illustrated in FIG. 30 comprises a material which is more flexible than the material of the rigid inner shaft portion 143$^j$.

FIG. 30 shows an embodiment of an inner shaft 140$^j$ comprising a rigid inner shaft portion 143$^k$, a bendable inner shaft portion 147$^k$ and a distal rigid shaft portion 149$^k$. The distal rigid shaft portion 149$^k$ extends proximally from the grabbing element proximal surface 194, and the bendable inner shaft portion 147$^k$ extends between the distal rigid shaft portion 149$^k$ and the rigid inner shaft portion 143$^k$. The bendable inner shaft portion 147$^k$ in the exemplary embodiment illustrated in FIG. 31 comprises a material which is more flexible than the material of the rigid inner shaft portion 143$^k$ and the material of the distal rigid shaft portion 149$^k$. According to some embodiments, the rigid inner shaft portion 143$^k$ and the distal rigid shaft portion 149$^k$ comprise the same materials.

FIG. 32 shows an embodiment of an inner shaft 140$^m$ comprising a bendable inner shaft portion 147$^m$ extending proximally from the grabbing element proximal surface 194, and a rigid inner shaft portion 143$^m$ extending proximally from the proximal end of the bendable inner shaft portion 147$^m$. The bendable inner shaft portion 147$^m$ in the exemplary embodiment illustrated in FIG. 32 comprises a plurality of bellows that impart flexibility thereof.

FIG. 33B shows an embodiment of the bendable inner shaft portion 147$^m$ bent relative to the outer shaft 120$^i$ such that the grabbing element front plane 54, now angled at an angle β relative to the centerline 50 of the outer shaft 120$^i$, is substantially congruent to the adjacent plane of the pericardium 14, such that the grabbing element 190 contacts the pericardium substantially along the entire circumference of the grabbing element distal surface 196.

According to some embodiments, the bendable inner shaft portion 147 is configured to transition between an unbent shaft state, when no external force is acting thereon, and a bent shaft state when subjected to an external force, for example when the grabbing element 190 is pressed against a distal surface.

While the grabbing element 190 shown in the exemplary embodiment of FIGS. 33A-B is attached to the inner shaft 140$^m$, disposed within an outer shaft 120$^i$ connected to a cone head, it will be clear that any inner shaft 140 having a bendable inner shaft portion 147, any outer shaft 120 and any cone head 160 disclosed throughout the specification, can be combined together.

Figure 34A:
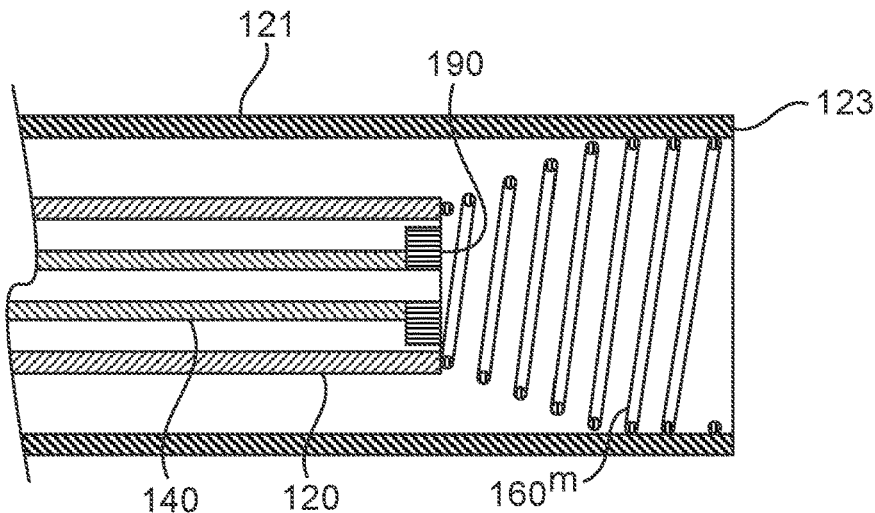
FIG. 34A constitutes a cross-sectional side view of a distal portion of the non-penetrating tissue separator equipped with a spring-coiled cone head retained within a delivery shaft, according to some embodiments.
Figure 34B:
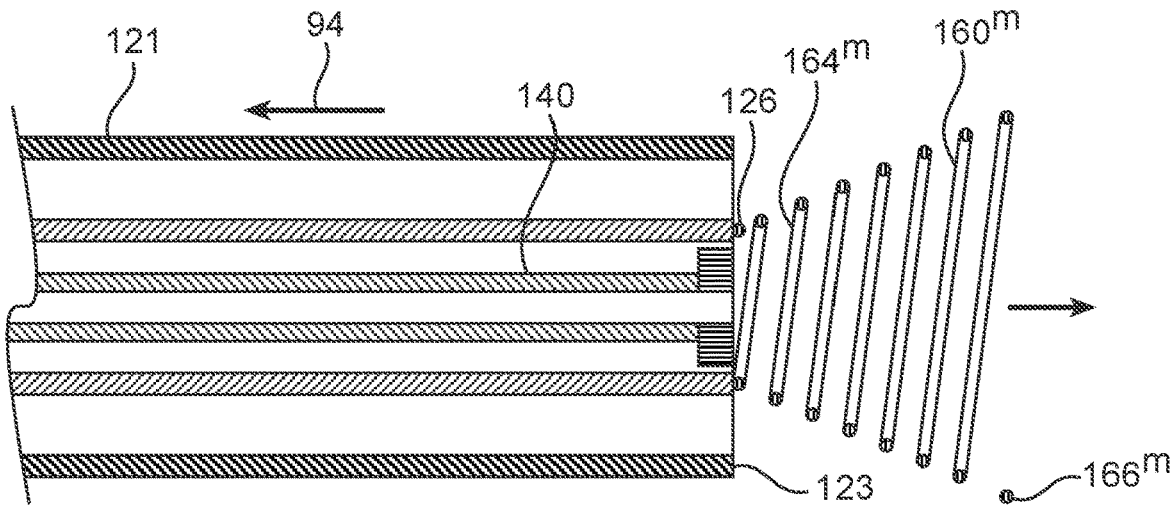
FIG. 34B constitutes a cross-sectional side view of a distal portion of the non-penetrating tissue separator equipped with a spring-coiled cone head extending distally from a delivery shaft, while being in a first state, according to some embodiments.
Figure 34C:
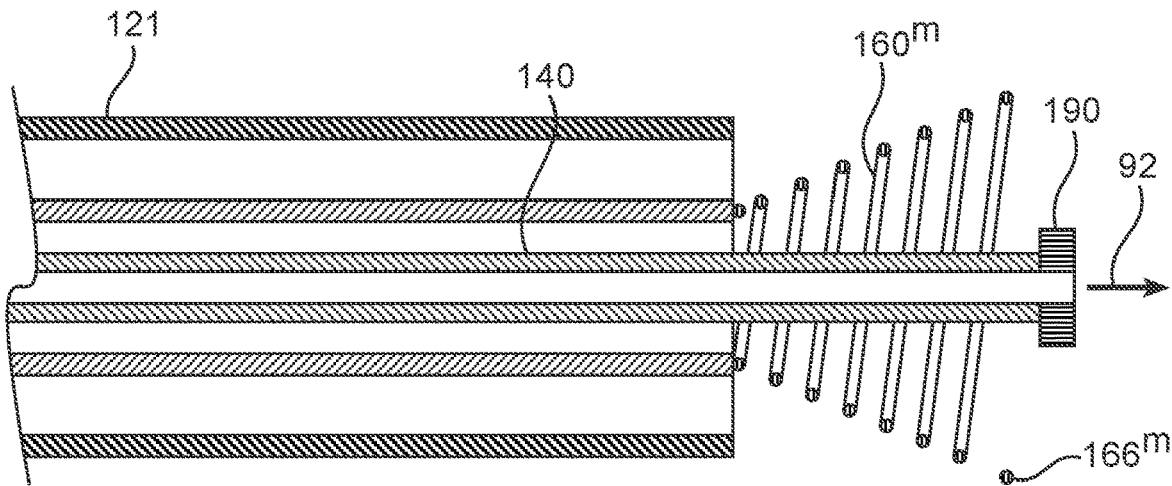
FIG. 34C constitutes a cross-sectional side view of a distal portion of the non-penetrating tissue separator equipped with a spring-coiled cone head extending distally from a delivery shaft, while being in a second state, according to some embodiments.
Figure 34D:
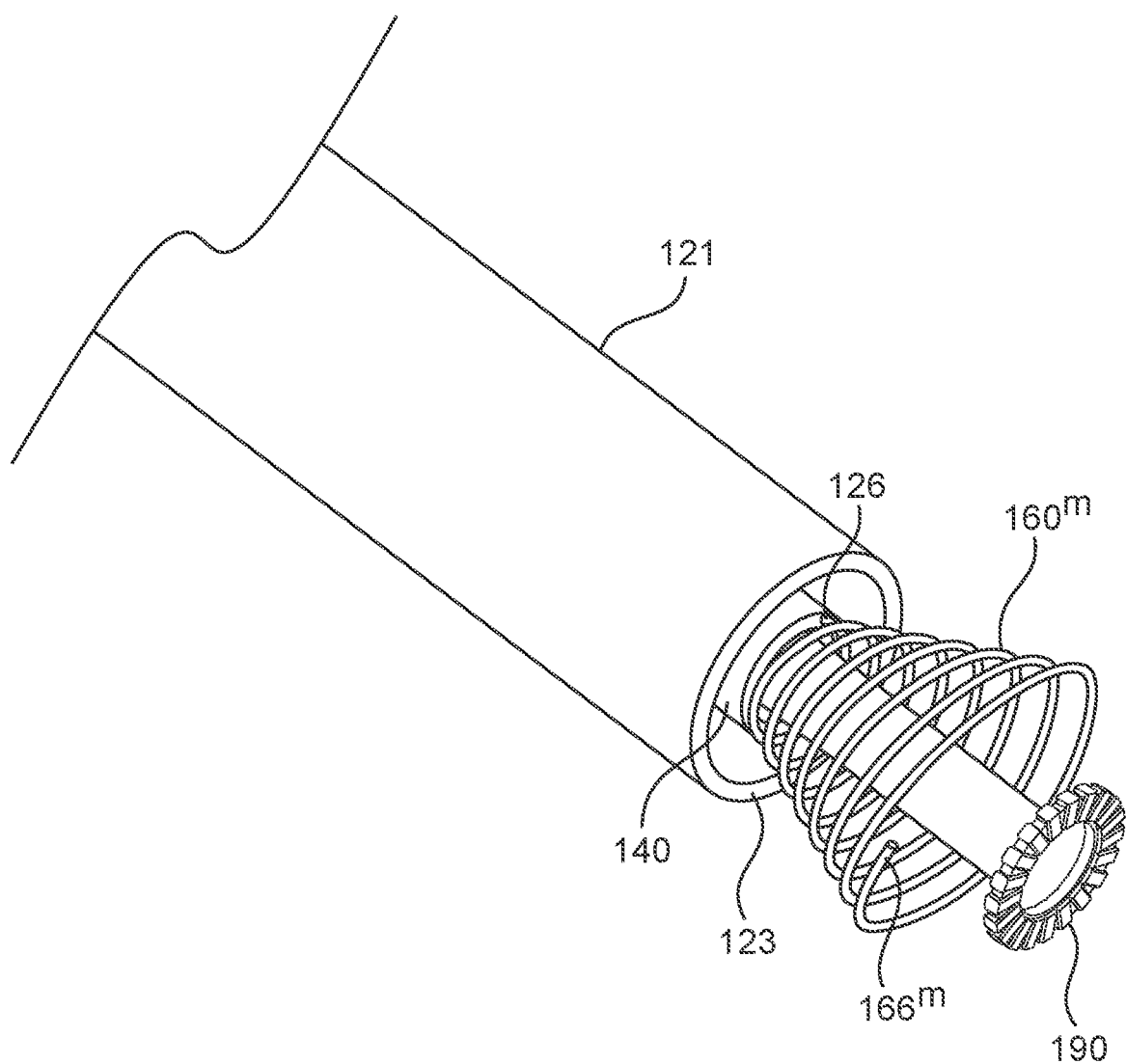
FIG. 34D constitutes a view in perspective of the distal portion of the non-penetrating tissue separator equipped with a spring-coiled cone head of FIG. 33C.

Reference is now made to FIGS. 34A-34D. FIGS. 34A-C constitute cross sectional side views of a distal portion of the non-penetrating tissue separator 100 equipped with a spring-coiled cone head 160$^m$ at different states, according to some embodiments. FIG. 34D constitutes a view in perspective of the distal portion of the non-penetrating tissue separator 100 equipped with a spring cone head 160$^m$ at the second state of FIG. 34C.

According to some embodiments, the non-penetrating tissue separator 100 of any of the embodiments disclosed throughout the specification comprises s spring-coiled cone head 160$^m$, formed as at least one helical coil having a plurality of spaced windings. The cone proximal portion 164$^m$ is attached to the outer shaft distal lip 126. According to some embodiments, the most proximal winding of the spring-coiled cone head 160$^m$ is provided with a diameter substantially equal to that of the outer shaft distal lip 126.

The most distal winding of the spring-coiled cone head 160$^m$, which may define the cone opening 168$^m$, is provided with an outer diameter which is larger than the diameter of the outer shaft distal lip 126. According to some embodiments, each adjacent winding from the proximal end of the spring-coiled cone head 160$^m$ to its distal end increases in diameter in the free-spring state, defined as the state in which the spring-coiled cone head 160$^m$ is not subjected to any external force.

According to some embodiments, the non-penetrating tissue separator 100 further comprises a delivery shaft 121, coaxial with and disposed around at least a portion of the outer shaft 120, so as to enable relative axial movement between the outer shaft 120 and the delivery shaft 121. Specifically, at least one of the outer shaft 120 or the delivery shaft 121 is axially movable relative to the delivery shaft 121 or the outer shaft 120, respectively, for example in a telescoping manner.

According to some embodiments, the outer shaft 120 can be moved distally while the delivery shaft 121 is stationary, thereby causing the spring-coiled cone head 160$^m$ attached to its distal end to move distally relative to the delivery shaft distal lip 123. According to some embodiments, the delivery shaft 121 can be moved proximally while the outer shaft 120 is stationary, thereby causing the delivery shaft distal lip 123 to move proximally relative to the cone distal portion 166$^m$.

According to some embodiments, the outer shaft 120 can slide freely within the lumen of the delivery shaft 121. According to some embodiments, the delivery shaft 121 can slide freely over the outer shaft 120.

According to some embodiments, the spring-coiled cone head 160$^m$ can be completely retained within the lumen of the delivery shaft 121. According to some embodiments, the diameter of the cone opening 168$^m$ is larger than the diameter of the delivery shaft distal lip 123.

FIG. 34A shows the spring-coiled cone head 160$^m$ retained along its entire length within the delivery shaft 121, such that the cone distal portion 166$^m$ is flush with or proximal to the delivery shaft distal lip 123.

According to some embodiments, the diameter of at least some of the windings of the spring-coiled cone head 160$^m$, mainly the distal windings, can be reduced, along with appropriate readjustment of the spaces between such adjacent coils, in order to accommodate the spring-coiled cone head 160$^m$ within the delivery shaft 121.

FIG. 34B shows the spring-coiled cone head 160$^m$ completely extending beyond the delivery shaft distal lip 123, allowing its windings to expand to their spring-free state. This can be achievable by either retracting the delivery shaft 121 in the proximal direction 94 relative to the outer shaft 120, or by advancing the outer shaft 120 in a distal direction 92 relative to the delivery shaft 121.

According to some embodiments, only a portion of the spring-coiled cone head 160$^m$ extends beyond the delivery shaft distal lip 123, at a length sufficient to expand all of its windings to the spring-free state, such that none of the windings that remain enclosed by the delivery shaft 121 contact or are pressed by the inner walls of the delivery shaft 121.

When the spring-coiled cone head 160$^m$ extends wholly or partially beyond the delivery shaft distal lip 123, its most distal edge, defined by the most distal winding, serves as the distal end of the non-penetrating tissue separator 100.

The grabbing element 190 in FIG. 34B is shown in a first state, proximal to the distal end of the non-penetrating tissue separator 100, or in other words, proximal to the distal edge of the spring-coiled cone head 160$^m$.

FIGS. 34C-D show the grabbing element 190 in a second end, distal to the distal end of the non-penetrating tissue separator 100, or in other words, distal to the distal edge of the spring-coiled cone head 160$^m$. This can be achieved, for example, by advancing the outer shaft 140 along with the grabbing element 190 in the distal direction 92.

According to some embodiments, the spring-coiled cone head 160$^m$ comprises a single helical coil as shown in FIGS. 34A-D. According to some embodiments, the spring-coiled cone head 160 comprises two concentric helical coils (embodiments not shown). According to some embodiments, both coils of the spring-coiled cone head 160 are wound in the same direction.

According to some embodiments, there is provided a non-penetrating tissue separator 100 comprising a delivery shaft 121 and a cone head 160$^o$ comprises a plurality of wings 170$^o$ oriented in a distal axial direction, separated by notches there between (embodiments not shown). Each wing 170° comprises a wing distal lip 172°, wherein the plurality wing distal lips 172°, together form the cone distal lip 174°.

Unlike the wings 170 of FIGS. 1C-1E, which are provided with an internal flexibility such that they are spring-biased radially inwards, the wings 170° are provided with internal flexibility such that they are spring-biased radially outwards, and can be pushed radially inwards by a force exerted thereon. When no external force is exerted on the wings 170°, their distal lips 172° expand radially away from each other, to form a wider cone opening 168° relative to an unexpanded (or contracted) position.

According to some embodiments, the cone head 160° is configured to switch between an unexpanded (or contracted) state of its wings 170° when retained within the lumen of the delivery shaft 121, and an expanded state when the wings 170° extend distal to the delivery shaft distal lip 123.

According to some embodiments, the outer shaft 120 can be moved distally while the delivery shaft 121 is stationary, thereby causing the cone head 160° attached to its distal end to move distally relative to the delivery shaft distal lip 123, having its wings 170° expanding radially outwards to their expanded state. According to some embodiments, the delivery shaft 121 can be moved proximally while the outer shaft 120 is stationary, thereby causing the delivery shaft distal lip 123 to move proximally relative to the cone distal portion 166°, while the wings 170° expand to their expanded state.

According to some embodiments, the cone head 160° can be completely retained within the lumen of the delivery shaft 121. According to some embodiments, the diameter of the cone opening 168°, when the wings 170° are expanded, is larger than the diameter of the delivery shaft distal lip 123.

According to some embodiments, the cone head 160° is designed such that it is sufficient for a portion thereof to extend beyond the delivery shaft distal lip 123, to completely expand the wings 170°.

When the cone head 160° extends wholly or partially beyond the delivery shaft distal lip 123, its cone distal lip 174° serves as the distal end of the non-penetrating tissue separator 100.

According to some embodiments, the outer shaft 120 can be retracted proximally while the delivery shaft 121 is stationary, thereby causing the wings 170° to contract radially inwards inside the lumen of the delivery shaft 121. According to some embodiments, the delivery shaft 121 can be moved proximally while the outer shaft 120 is stationary, thereby causing the wings 170° to contract radially inwards inside the lumen of the delivery shaft 121.

According to some embodiments, there is provided a non-penetrating tissue separator 100 comprising a cone head 160° attached to the inner shaft 140 instead of to the outer shaft 120 (embodiments not shown). In such embodiments, the cone head 160° is configured to switch between an unexpanded (or contracted) state of its wings 170° when retained within the lumen of outer shaft lumen 132, and an expanded state when the wings 170° extend distal to the relative to the outer shaft distal lip 126.

According to some embodiments, the inner shaft 140 can be moved distally while the outer shaft 120 is stationary, thereby causing the cone head 160° attached to the inner shaft distal portion 144 to move distally relative to the outer shaft distal lip 126, having its wings 170° expanding radially outwards to their expanded state. According to some embodiments, the outer shaft 120 can be moved proximally while the inner shaft 140 is stationary, thereby causing the outer shaft distal lip 126 to move proximally relative to the cone distal portion 166°, while the wings 170° expand to their expanded state.

According to some embodiments, the cone head 160° can be completely retained within the outer shaft lumen 132. According to some embodiments, the diameter of the cone opening 168°, when the wings 170° are expanded, is larger than the diameter of the outer shaft distal lip 126.

According to some embodiments, the cone head 160° is designed such that it is sufficient for a portion thereof to extend beyond the outer shaft distal lip 126, to completely expand the wings 170°.

When the cone head 160° extends wholly or partially beyond the outer shaft distal lip 126, its cone distal lip 174° serves as the distal end of the non-penetrating tissue separator 100.

According to some embodiments, the inner shaft 140 can be retracted proximally while the outer shaft 120 is stationary, thereby causing the wings 170° to contract radially inwards inside the outer shaft lumen 132. According to some embodiments, the outer shaft 120 can be moved proximally while the inner shaft 140 is stationary, thereby causing the wings 170° to contract radially inwards inside the outer shaft lumen 132.

Advantageously, an expandable cone head 160, such as but not limited to the embodiments of cone heads 160″, 160°, enable advancing the distal end of the non-penetrating tissue separator 100 through the patient's organs or tissue, up to the vicinity of the thoracic cavity or the vicinity of the heart 10 in an unexpanded or contracted state of the cone head 160, thereby reducing the front surface area contacting such tissues and reducing resistance to the advancement of the device 100, while the cone head 160 can be expanded to assume its conical profile only upon reaching the vicinity of the heart 10, such as the vicinity of the pericardial tissue 14.

According to some embodiments, some of the components of the non-penetrating tissue separator 100 are reusable, and some of its components are disposable. According to some embodiment, the handle 102 is reusable. According to some embodiments, at least one of the inner shaft 140, the outer shaft 120, the grabbing element 190 and the cone head 160 is disposable, and can be replaced for each procedure.

According to some embodiments, some of the components of the non-penetrating tissue separator 100 are replaceable. According to some embodiments, the shaft spring 116, $116^a a$, $116^a b$ is replaceable. The spring constant k of the shaft spring 116, $116^a a$, $116^a b$ can be chosen so as to enable sufficient desired range of expansion/contraction thereof, and avoiding high stiffness that may result in high pressure application by the non-penetrating tissue separator 100 on the heart 10 during the procedure.

According to some embodiments, different shaft springs 116, $116^a a$, $116^a b$ can be configured for use with patients presenting different characteristics, anatomies or pathologies, such that the appropriate shaft spring 116, $116^a a$, $116^a b$ can be mounted in the non-penetrating tissue separator 100 according to a patient's characteristics.

According to some embodiments, the grabbing element 190 is replaceable. According to some embodiments, different grabbing elements 190 can be configured for use with patients presenting different characteristics, anatomies or pathologies, such that the appropriate grabbing element 190 can be mounted in the non-penetrating tissue separator 100 according to a patient's characteristics.

According to some embodiments, the cone head 160 is replaceable. According to some embodiments, different cone heads 160 can be configured for use with patients presenting different characteristics, anatomies or pathologies, such that the appropriate cone head 160 can be mounted in the non-penetrating tissue separator 100 according to a patient's characteristics.

According to some embodiments, the non-penetrating tissue separator 100 further comprises a rotation limiting mechanism, configured to limit the maximal rotation of the grabbing element 190. According to some embodiments, the rotation limiting mechanism configured to limit the rotation of the grabbing element 190 within a predefined range. According to some embodiments, the rotation limiting mechanism configured to limit the rotation of the grabbing element 190 within a range of 0-270 degrees. According to some embodiments, the rotation limiting mechanism configured to limit the rotation of the grabbing element 190 within a range of 0-180 degrees.

According to some embodiments, the rotation limiting mechanism configured to limit the rotation of the grabbing element 190 to a limited amount of rotations in at least one direction.

Advantageously, a rotation limiting mechanism can be designed to allow a maximal degree of rotation, or alternatively, a maximal amount of rotations, that will refrain from inflicting damage by the grabbing element 190 to the wrapped tissue, such as the pericardium 14.

According to some embodiments, the grabbing element 190 comprises a ferromagnetic material, and the non-penetrating tissue separator 100 further comprises magnetic attraction component proximal to the grabbing element 190, configured to apply a magnetic force for either attracting or repelling the grabbing element 190 (embodiments not shown).

According to some embodiments, the magnetic attraction component is attached to the inner shaft 140. According to some embodiments, the magnetic attraction component is attached to the outer shaft 120. According to some embodiments, the magnetic attraction component is disposed within the inner shaft lumen 152. According to some embodiments, the magnetic attraction component is disposed within the outer shaft lumen 132. According to some embodiments, the magnetic attraction component is disposed over the outer shaft external surface 128.

According to some embodiments, the magnetic attraction component can be axially maneuvered in the distal and proximal directions, for example via the handle 102. According to some embodiments, the magnetic attraction component can be rotated around its axis of symmetry, for example via the handle 102.

According to some embodiments, the magnetic attraction component can be displaced from a non-attracting state in which the grabbing element 190 is not attracted thereto, and an attracting state in which the grabbing element 190 is attracted thereto. According to some embodiments, the position of the magnetic attraction component, such as its distance from the grabbing element 190, can be controlled by an operator of the non-penetrating tissue separator 100 to switch between the non-attracting and attracting states.

In use, the magnetic attraction component can be switched to or retained in a non-attracting state when the grabbing element 190 moves from a first state to a second state, and it can switch to the attracting state after the pericardium 14 is sufficiently wrapped around the grabbing element 190, in order to facilitate proximal retraction of the grabbing element 190.

According to some embodiments, the inner shaft 140 comprises inner shaft surface features disposed along at least a portion of the inner shaft external surface 148, extending proximally from the grabbing element 190.

According to some embodiments, the inner shaft 140 comprises inner shaft surface features disposed along at least a portion of the inner shaft distal portion 144.

The inner shaft surface features can be in any form disclosed for the surface features 188 of the grabbing element 190, and may be either similarly shaped or different from surface features 188 disposed along at least one surface of the grabbing element 190.

Advantageously, inner shaft surface features support further wrapping and retention of a tissue, when the tissue is wrapped around the grabbing element 190 and propagates proximally to further wrap around the inner shaft distal portion 144.

According to some embodiments, the methods and devices of the current disclosure are utilized during treatment procedures of at least one of: laparoscopic surgery, AV fistula access, bone biopsy, Arthroscopic surgery, Pleuracentesis, Thoracoscopic surgery, Thoracentesis, Amniocentesis, Abscess Drainage, Hemodialysis or Peritoneum.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A non-penetrating tissue separator comprising:
an outer shaft having an outer shaft lumen, an outer shaft distal portion, and an outer shaft distal lip;
an inner shaft having an inner shaft lumen and an inner shaft external surface;
a grabbing element attached to a distal edge of the inner shaft and having a grabbing element distal surface, a grabbing element proximal surface, a grabbing element circumferential surface, a grabbing element inner opening, and surface features disposed along at least one of the grabbing element distal surface, the grabbing element proximal surface, or the grabbing element circumferential surface,
wherein at least a portion of the outer shaft is disposed around at least a portion of the inner shaft, so as to enable relative axial movement between the inner shaft and the outer shaft, thereby facilitating positioning of the grabbing element between a first state and a second state;
wherein the grabbing element is rotatable about a central axis thereof,
wherein the central axis of the grabbing element is directed in a distally oriented direction, orthogonal to the grabbing element distal surface, and wherein the surface features are atraumatic surface features, configured to releasably engage and grasp a tissue via the surface features, without cutting, dissecting or penetrating it, during rotational movement of the grabbing element around its central axis, and to retain the tissue engaged therewith after rotational movement is halted.

2. The non-penetrating tissue separator of claim 1, further comprising a handle attached to at least one of the inner shaft and the outer shaft, wherein the handle is configured to facilitate relative axial movement between the inner shaft and the outer shaft, and wherein the handle is configured to facilitate rotation of the grabbing element.

3. The non-penetrating tissue separator of claim 2, wherein the handle further comprises a steering knob engaged with the inner shaft and configured to facilitate at least one of axial movement or rotational movement of the inner shaft.

4. The non-penetrating tissue separator of claim 2, wherein the handle further comprises a second handle niche, configured to enable visual exposure of at least a portion of the inner shaft extending there-through.

5. The non-penetrating tissue separator of claim 4, further comprising a first shaft spring disposed between the inner shaft and the handle, configured to provide resistance to a proximal displacement of the inner shaft.

6. The non-penetrating tissue separator of claim 5, further comprising a second shaft spring disposed between the inner shaft and the handle, configured to provide resistance to a distal displacement of the inner shaft.

7. The non-penetrating tissue separator of claim 6, further comprising indicia for indicating at least one of: the position of the grabbing element, the force applied by the grabbing element when pressed against an external surface, whether the tissue provides resistance to a proximal pull of the grabbing element, or whether the tissue has been grabbed by the grabbing element.

8. The non-penetrating tissue separator of claim 7, wherein the inner shaft comprises a structural feature or a marking that can be compared against the indicia.

9. The non-penetrating tissue separator of claim 1, further comprising a cone head attached to the outer shaft distal portion and having a cone head distal lip defining a cone head opening.

10. The non-penetrating tissue separator of claim 9, wherein the cone head further comprising a plurality of wings, configured to switch between a non-expanded state and an expanded state.

11. The non-penetrating tissue separator of claim 9, wherein the cone head is formed as at least one helical coil having a plurality of spaced windings.

12. The non-penetrating tissue separator of claim 9, wherein the cone head is configured to tilt relative to the outer shaft, thereby transitioning between an un-tilted cone state and a tilted cone state.

13. The non-penetrating tissue separator of claim 1, further comprising a delivery shaft disposed around at least a portion of the outer shaft, so as to enable relative axial movement between the outer shaft and the delivery shaft.

14. The non-penetrating tissue separator of claim 1, wherein the grabbing element is disc shaped, such that its axial length is shorter than its outer diameter.

15. The non-penetrating tissue separator of claim 1, wherein the grabbing element is elongated, such that its axial length is equal to or longer than its outer diameter.

16. The non-penetrating tissue separator of claim 1, wherein the inner shaft comprises a bendable inner shaft portion and a rigid inner shaft portion, such that a distal end of the inner shaft is configured to bend relative to the outer shaft.

17. The non-penetrating tissue separator of claim 1, wherein the inner shaft further comprises inner shaft surface features disposed along at least a portion of the inner shaft external surface.

18. The non-penetrating tissue separator of claim 1, further comprising an access device passable through the inner shaft lumen and through the grabbing element inner opening, and configured to either puncture, cut or penetrate the pericardium.

19. The non-penetrating tissue separator of claim 18, wherein the access device is a needle comprising a distal needle portion.

20. The non-penetrating tissue separator of claim 19, further comprising a cone head attached to the outer shaft distal portion and having a cone head distal lip defining a cone head opening, wherein the distal needle portion is proximal to the cone head distal lip both in the first state and in the second state.

* * * * *